(12) United States Patent
Li et al.

(10) Patent No.: US 8,699,009 B2
(45) Date of Patent: Apr. 15, 2014

(54) DISTRIBUTED OPTICAL FIBER SENSOR

(75) Inventors: Che-Hsien Li, Kobe (JP); Kinzo Kishida, Kobe (JP); Kenichi Nishiguchi, Kobe (JP); Artur Guzik, Kobe (JP); Atsushi Makita, Kobe (JP); Yoshiaki Yamauchi, Kobe (JP)

(73) Assignee: Neubrex Co., Ltd. (JP)

( * ) Notice: Subject to any disclaimer, the term of this patent is extended or adjusted under 35 U.S.C. 154(b) by 341 days.

(21) Appl. No.: 13/130,779

(22) PCT Filed: Nov. 6, 2009

(86) PCT No.: PCT/JP2009/068965
§ 371 (c)(1),
(2), (4) Date: May 24, 2011

(87) PCT Pub. No.: WO2010/061718
PCT Pub. Date: Jun. 3, 2010

(65) Prior Publication Data
US 2011/0228255 A1 Sep. 22, 2011

(30) Foreign Application Priority Data

Nov. 27, 2008 (JP) .................................. 2008-302878
Aug. 3, 2009 (JP) .................................. 2009-180615

(51) Int. Cl.
*G01B 11/16* (2006.01)
*G01L 1/24* (2006.01)
*G01N 21/21* (2006.01)

(52) U.S. Cl.
CPC .............. *G01L 1/242* (2013.01); *G01B 11/168* (2013.01); *G01N 21/21* (2013.01)
USPC .......................................................... 356/33

(58) Field of Classification Search
None
See application file for complete search history.

(56) References Cited

U.S. PATENT DOCUMENTS

| 6,380,534 B1 | 4/2002 | Farhadiroushan et al. |
| 7,719,666 B2 | 5/2010 | Kishida et al. |

(Continued)

FOREIGN PATENT DOCUMENTS

| CN | 201104243 | 8/2008 |
| GB | 2436142 A * | 9/2007 |

(Continued)

OTHER PUBLICATIONS

Rathod et al, Distributed temperature-change sensor based on Rayleigh backscattering in an optical fiber, Apr. 15, 1994, Optics Letters, vol. 19, No. 8, pp. 593-595.*

(Continued)

*Primary Examiner* — Gregory J. Toatley, Jr.
*Assistant Examiner* — Juan D Valentin, II
(74) *Attorney, Agent, or Firm* — Gerald E. Hespos; Michael J. Porco; Matthew T. Hespos

(57) ABSTRACT

The present invention provides a distributed optical fiber sensor capable of measuring the strain and temperature of an object to be measured simultaneously and independently with high spatial resolution. A distributed optical fiber sensor FS is a distributed optical fiber sensor which uses an optical fiber 15 as a sensor, and a strain and temperature detector 14 measures a Brillouin frequency shift amount caused by a strain and a temperature generated in the optical fiber 15 by using a Brillouin scattering phenomenon, measures a Rayleigh frequency shift amount caused by the strain and temperature generated in the optical fiber 15 by using a Rayleigh scattering phenomenon, and calculates the strain and temperature generated in the optical fiber 15 from the measured Brillouin frequency shift amount and Rayleigh frequency shift amount.

13 Claims, 29 Drawing Sheets

(56) References Cited

U.S. PATENT DOCUMENTS

| | | | |
|---|---|---|---|
| 2001/0050768 A1* | 12/2001 | Uchiyama et al. | 356/73.1 |
| 2006/0153274 A1* | 7/2006 | Seebacher | 374/130 |
| 2007/0171402 A1* | 7/2007 | Watley et al. | 356/73.1 |
| 2007/0242262 A1* | 10/2007 | MacDougall | 356/73.1 |
| 2008/0068586 A1 | 3/2008 | Kishida et al. | |
| 2008/0180681 A1* | 7/2008 | Digonnet | 356/477 |
| 2008/0204703 A1* | 8/2008 | Hernandezs-Solis et al. | 356/6 |
| 2009/0008536 A1* | 1/2009 | Hartog et al. | 356/483 |
| 2009/0079967 A1* | 3/2009 | Radic | 356/73.1 |
| 2009/0132183 A1 | 5/2009 | Hartog et al. | |
| 2010/0014071 A1* | 1/2010 | Hartog | 356/73.1 |
| 2011/0194107 A1 | 8/2011 | Hartog et al. | |

FOREIGN PATENT DOCUMENTS

| | | |
|---|---|---|
| JP | 2001-507446 | 6/2001 |
| JP | 2006-145465 | 6/2006 |
| KR | 100803377 | 2/2008 |
| WO | 2006/001071 | 1/2006 |

OTHER PUBLICATIONS

Study on optical communications—May 2008 (Sum. No. 149).

* cited by examiner

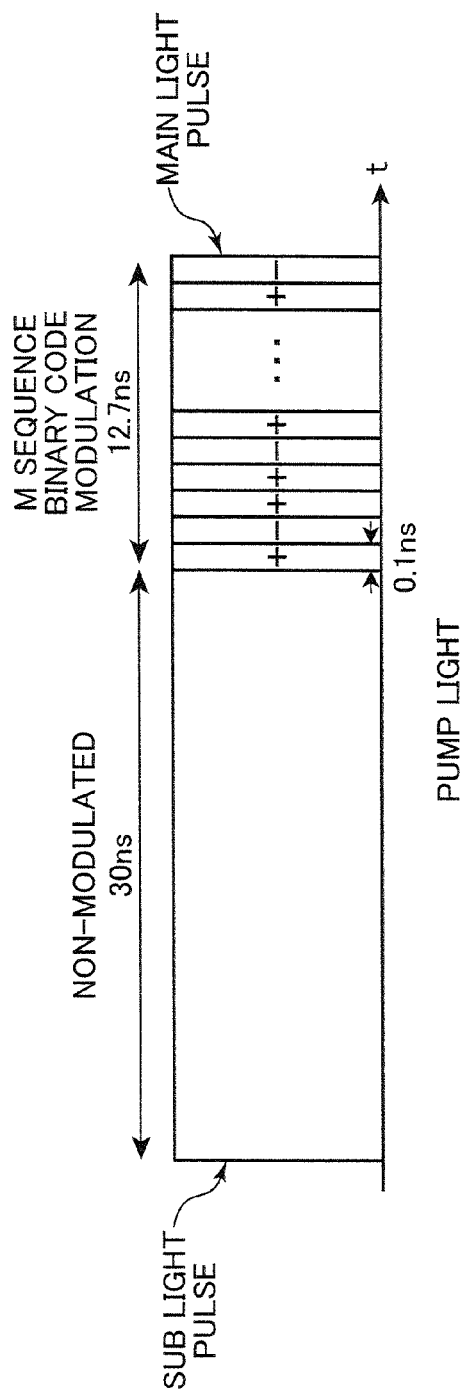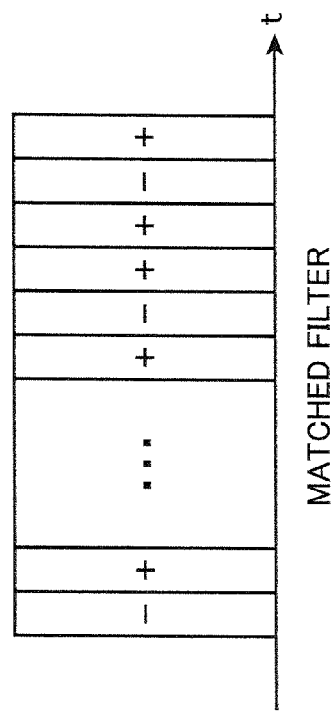

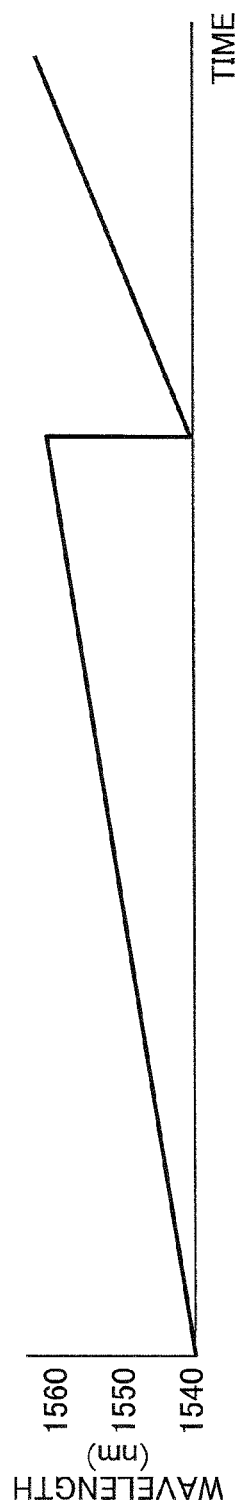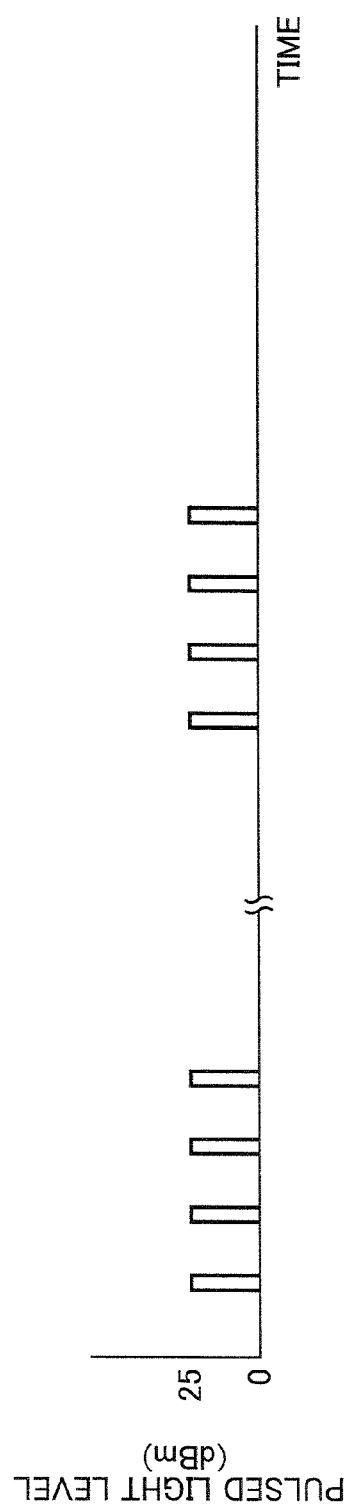

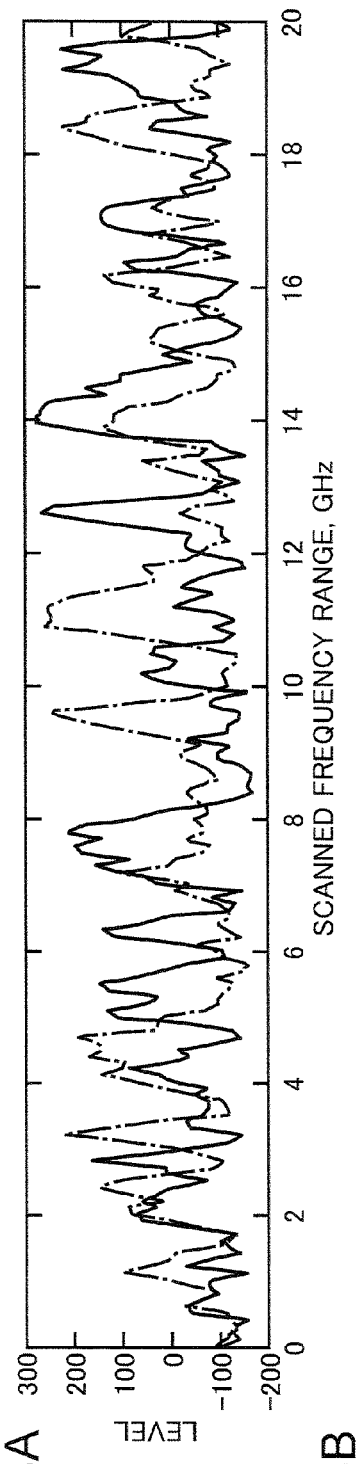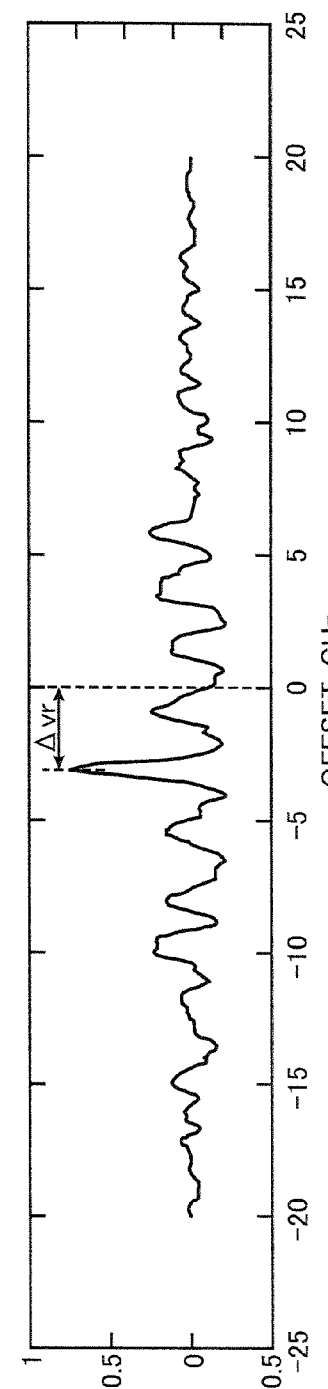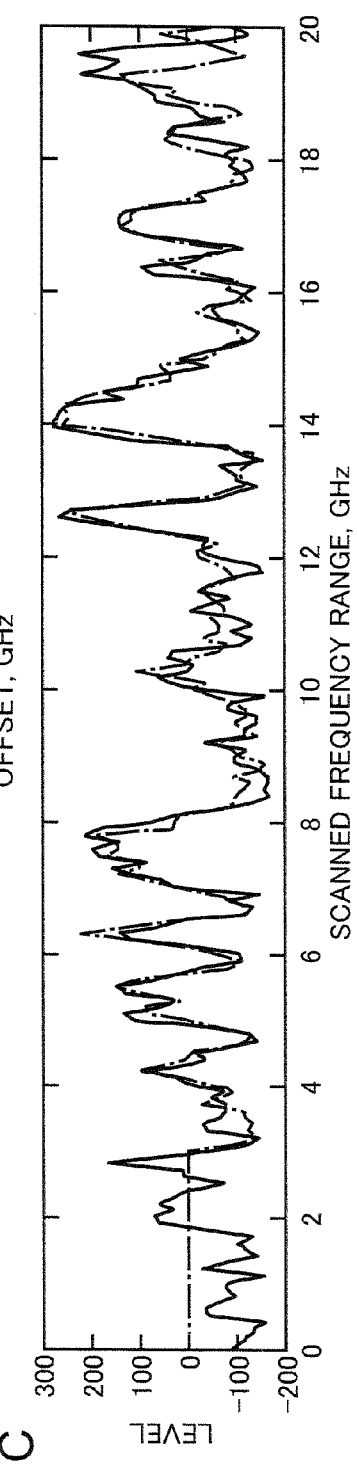

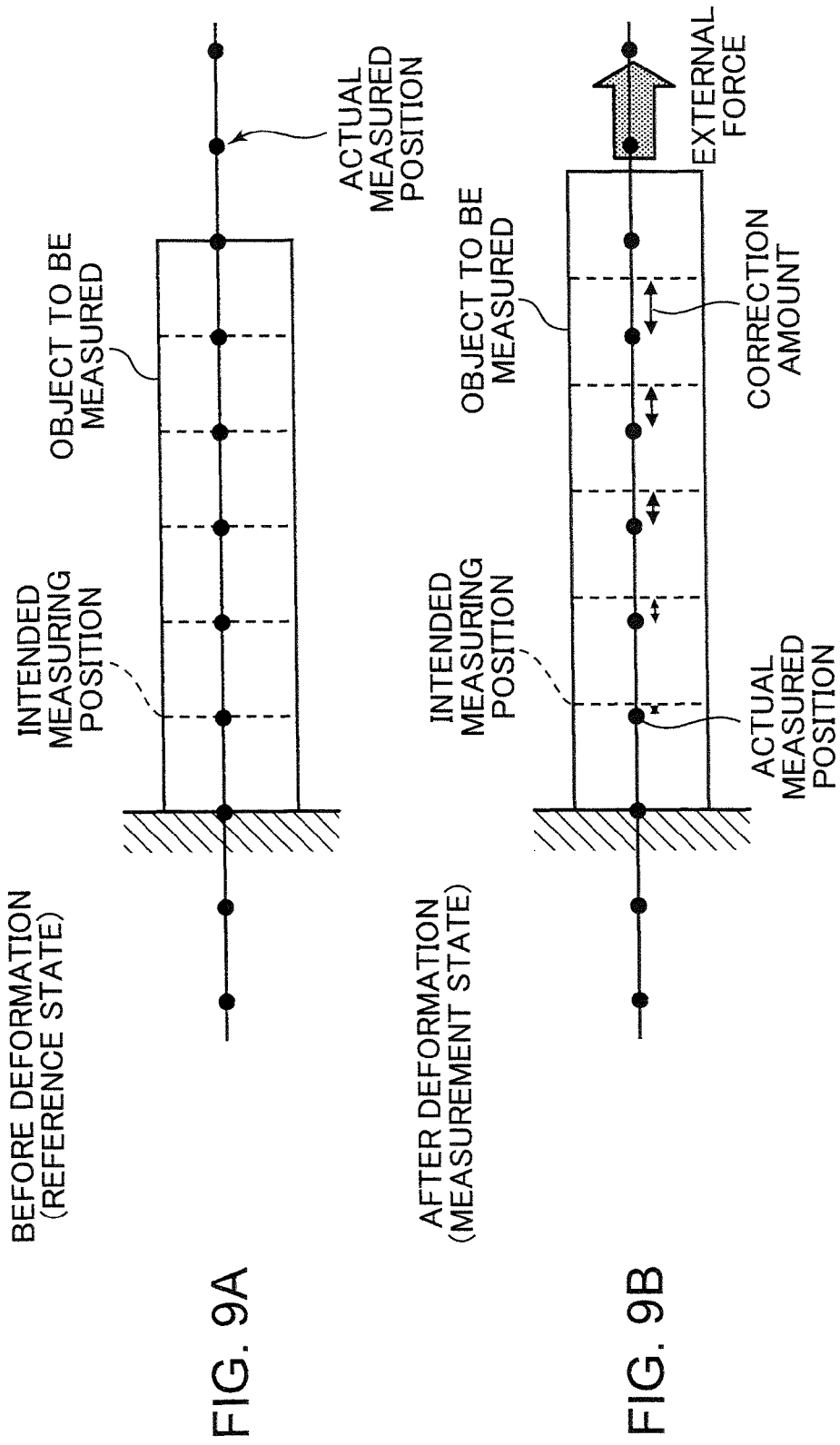

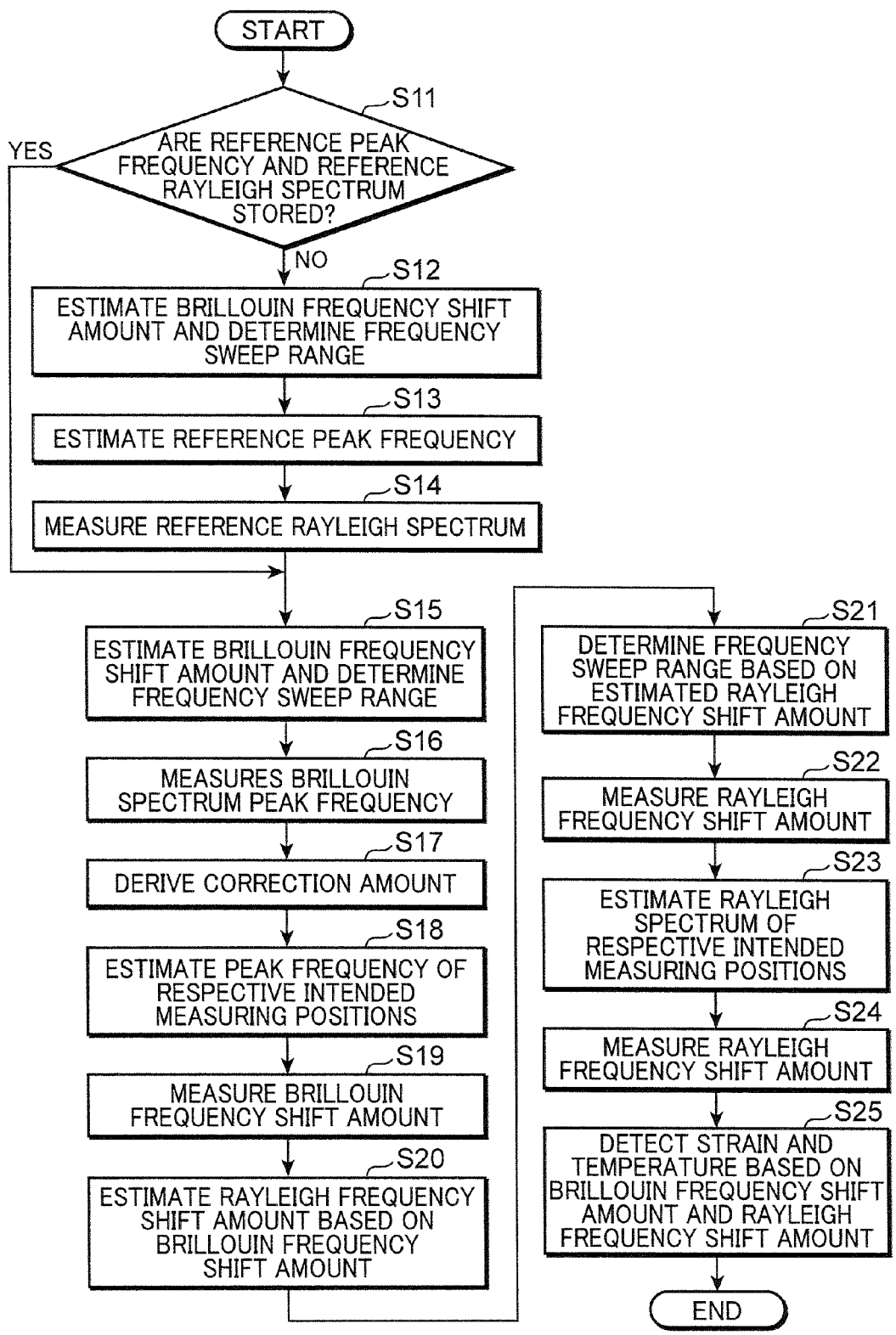

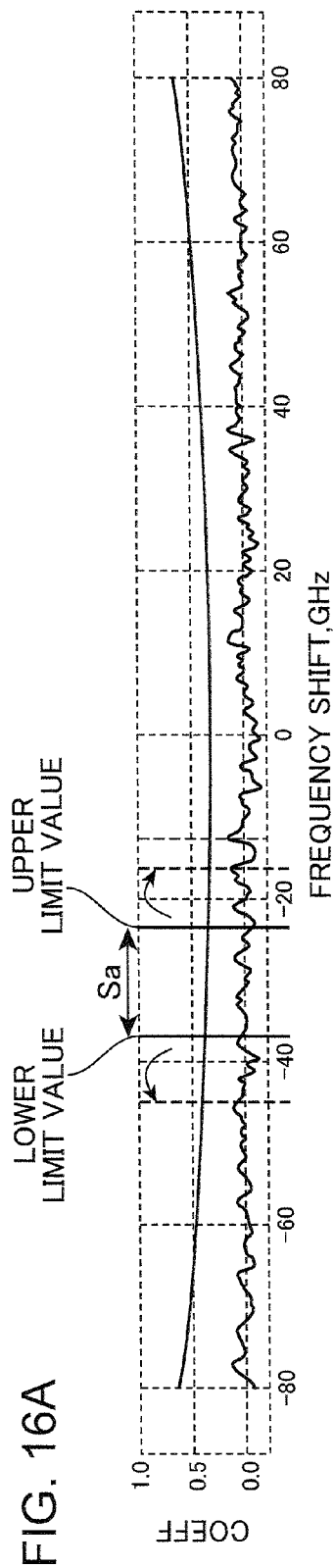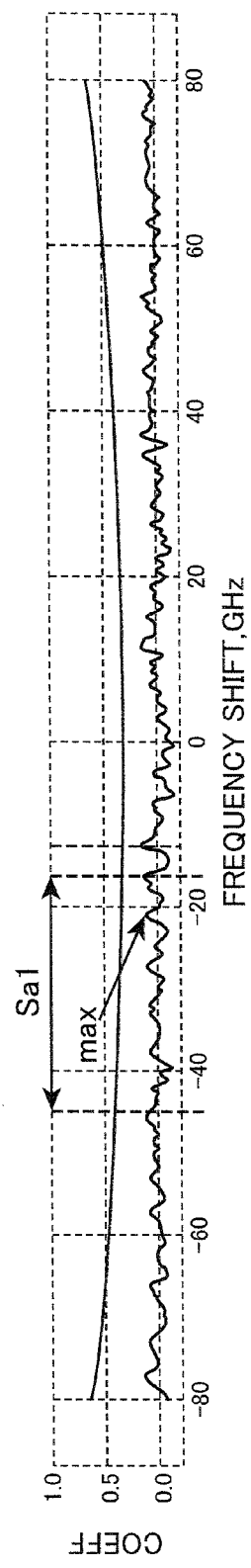

BRILLOUIN GAIN SPECTRUM

BRILLOUIN GAIN SPECTRUM

ESTIMATED VALUE OF FREQUENCY SHIFT

BRILLOUIN GAIN SPECTRUM

ESTIMATED VALUE OF FREQUENCY SHIFT

PUMP LIGHT

MATCHED FILTER

DISTRIBUTED OPTICAL FIBER SENSOR

BACKGROUND OF THE INVENTION

1. Field of the Invention

The present invention relates to a distributed optical fiber sensor which uses an optical fiber as a sensor, and which is capable of measuring the strain and temperature in the longitudinal direction thereof with high precision.

2. Description of the Related Art

Conventionally, as technology of measuring the strain and temperature, there is a method based on the Brillouin scattering phenomenon which occurs in the optical fiber. In this method, the optical fiber is used as the medium from which the strain and/or temperature is to be detected in the environment (object to be measured) where such optical fiber is to be installed.

The Brillouin scattering phenomenon is a phenomenon where power travels via the acoustic phonon in the optical fiber when light enters the optical fiber, and there are the stimulated Brillouin scattering phenomenon which occurs as a result of two lights with mutually different frequencies entering the optical fiber and based on the interaction of the two lights, and the natural Brillouin scattering phenomenon which occurs as a result of light entering the optical fiber and based on the interaction of the foregoing light and the acoustic phonon that is generated by the thermal noise in the optical fiber. The Brillouin frequency shift that is observed during the Brillouin scattering phenomenon is proportional to the sonic velocity in the optical fiber, and the sonic velocity is dependent on the strain and temperature of the optical fiber. Thus, the strain and/or temperature can be measured by measuring the Brillouin frequency shift.

As representative systems for measuring the distribution of strain and temperature using the Brillouin scattering phenomenon, there are BOTDA (Brillouin Optical Time Domain Analysis) and BOTDR (Brillouin Optical Time Domain Reflectometer).

Foremost, with the BOTDA, the stimulated Brillouin scattering phenomenon is used, two laser beams with mutually different frequencies enter the detection optical fiber in an opposing manner as pump light and probe light, and the optical intensity of the light pertaining to the stimulated Brillouin scattering phenomenon output from the end, of the detection optical fiber, into which the pump light entered is measured in the time domain. With the BOTDA, the acoustic phonon is excited based on the interaction of the pump light and the probe light.

Meanwhile, with the BOTDR, once laser beam enters as pump light from one end of the detection optical fiber, light pertaining to the natural Brillouin scattering phenomenon output from the one end is detected by an optical band pass filter, and the optical intensity of the detected light pertaining to the natural Brillouin scattering phenomenon is measured in the time domain. With the BOTDR, the acoustic phonon generated by the thermal noise is used.

Subsequently, with the BOTDA and the BOTDR described above, this kind of measurement is performed for each frequency while sequentially changing the frequency of the pump light or, in the case of the BOTDA, the frequency of the probe light, the Brillouin gain spectrums (or Brillouin loss spectrums in the BOTDA) of the respective portions along the longitudinal direction of the detection optical fiber are respectively obtained, and the strain distribution and/or temperature distribution along the longitudinal direction of the detection optical fiber is measured based on the foregoing measurement result. As the foregoing pump light, under normal circumstances, a light pulse with a rectangular optical intensity is used, and, as the probe light in the BOTDA, continuous light (CW light) is used.

Here, with the BOTDA, while the Brillouin gain spectrum is detected by causing the frequency of the pump light to be higher than the frequency of the probe light with the probe light as the reference on the one hand, the Brillouin loss spectrum is detected by causing the frequency of the probe light to be higher than the frequency of the pump light. Moreover, with the BOTDR, the Brillouin gain spectrum is detected. With the BOTDA, the strain and/or temperature can be obtained by using either the Brillouin gain spectrum or the Brillouin loss spectrum. In this specification, the Brillouin gain spectrum and the Brillouin loss spectrum are simply referred to as the "Brillouin spectrum" as appropriate when referring to the BOTDA.

The spatial resolution of the BOTDA and the BOTDR is restricted by the pulse width of the light pulse of the pump light that is used for the measurement. Although the speed of light in the optical fiber will differ slightly depending on the material of the optical fiber, with a standard optical fiber that is generally used, it takes approximately 28 ns for the complete rise of the acoustic phonon. Thus, the Brillouin spectrum is a Lorentzain curve up to where the pulse width of the light pulse is approximately 28 ns or more, and, if the light pulse width is made shorter than the above, it becomes a wide band curve, and takes on a smooth shape that lost its steepness in the vicinity of the center frequency. Thus, it becomes difficult to seek the center frequency, and the spatial resolution thereof is usually said to be approximately 2 to 3 m.

Thus, the present inventors proposed, in Brochure of International Publication No. 2006/001071, a method of measuring the distribution of the strain and/or temperature with high precision (for example, 200µε or less) and high spatial resolution (for example, 1 m or less) by configuring the foregoing light pulse from two components. The present inventors refer to this system as the PPP-BOTDA/BOTDR (Pulse Pre-Pumped BOTDA/BOTDR). Note that 100µε corresponds to 0.01% (100µε=0.01%). Moreover, the Brillouin frequency shift is approximately 500 MHz/% relative to the strain.

Nevertheless, since the Brillouin frequency shift amount that is measured using the Brillouin scattering phenomenon changes depending on the two parameters of strain and temperature of the optical fiber, the parameter that can be measured using the Brillouin scattering phenomenon is basically one of either the strain or temperature, and it is not possible to separately and simultaneously measure the strain and temperature.

SUMMARY OF THE INVENTION

An object of this invention is to provide a distributed optical fiber sensor capable of measuring the strain and temperature of an object to be measured simultaneously and independently with high spatial resolution.

In order to achieve the foregoing object, the distributed optical fiber sensor according to the present invention is a distributed optical fiber sensor which uses an optical fiber as a sensor, comprising a Brillouin measuring unit for measuring a Brillouin frequency shift amount caused by a strain and a temperature generated in the optical fiber by using a Brillouin scattering phenomenon, a Rayleigh measuring unit for measuring a Rayleigh frequency shift amount caused by the strain and temperature generated in the optical fiber by using a Rayleigh scattering phenomenon, and a calculation unit for calculating the strain and temperature generated in the optical fiber based on the Brillouin frequency shift amount measured by the Brillouin measuring unit and the Rayleigh frequency shift amount measured by the Rayleigh measuring unit.

According to this distributed optical fiber sensor, since the Brillouin frequency shift amount caused by the strain and temperature generated in the optical fiber is measured by using the Brillouin scattering phenomenon, and the Rayleigh frequency shift amount caused by the strain and temperature generated in the optical fiber is measured by using the Rayleigh scattering phenomenon, the strain and temperature generated in the optical fiber can be simultaneously and independently calculated by using two frequency shift amounts, and the strain and temperature of the object to be measured appended with an optical fiber can be measured simultaneously and independently with high spatial resolution.

Thus, the distributed optical fiber sensor according to the present invention can measure the strain and temperature of a test object simultaneously and independently with high spatial resolution.

BRIEF DESCRIPTION OF THE DRAWINGS

FIGS. 6A and 6B are diagrams explaining the configuration of pump light (sub light pulse and main light pulse) and the matched filter.

FIGS. 7A and 7B are diagram showing an example of the pulsed light that is output from the light pulse generation unit shown in FIG. 1.

FIGS. 8A, 8B and 8C are diagrams showing an example of the Rayleigh frequency shift amount measured by the distributed optical fiber sensor shown in FIG. 1.

FIGS. 9A and 9B are diagrams explaining the relation of the actual measured position and the intended measuring position.

FIG. 10 is a flowchart explaining the operation of measuring the strain and temperature performed by the distributed optical fiber sensor according to the second embodiment of the present invention.

FIGS. 16A and 16B are diagrams explaining the method of determining the scanning range for obtaining the Rayleigh frequency shift amount from the relation of the shift amount and cross-correlation coefficient of the measured Rayleigh spectrum relative to the reference Rayleigh spectrum.

DETAILED DESCRIPTION OF THE PREFERRED EMBODIMENTS

Figure 1:
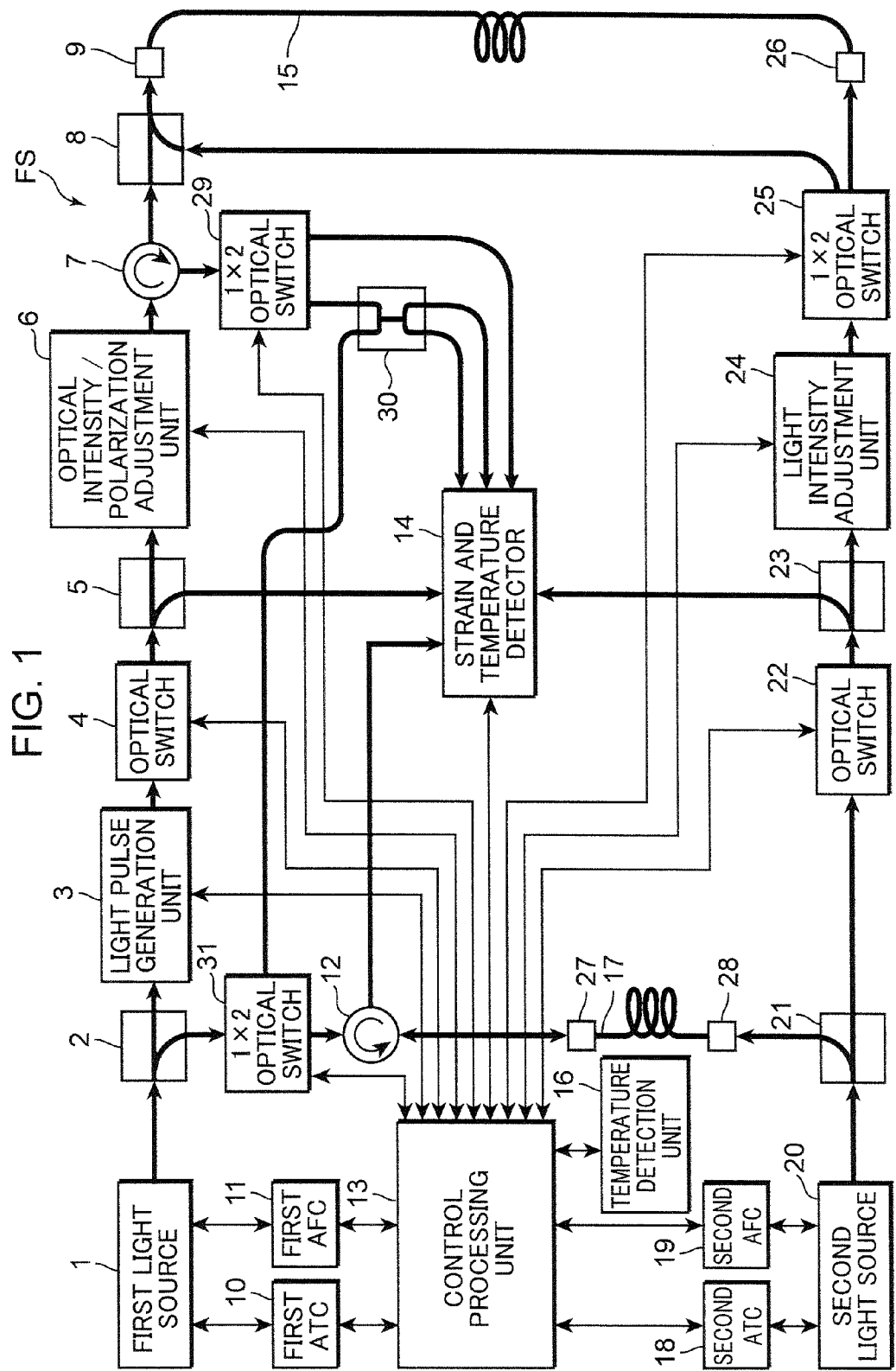
FIG. 1 is a block diagram showing the configuration of the distributed optical fiber sensor according to the first embodiment of the present invention.

The first embodiment of the distributed optical fiber sensor according to the present invention is now explained with reference to the appended drawings. Note that the configuration given the same reference numeral in the respective drawings shows that it is the same configuration, and the explanation thereof is omitted. FIG. 1 is a block diagram showing the configuration of the distributed optical fiber sensor in the first embodiment.

A distributed optical fiber sensor FS shown in FIG. 1 includes a first light source 1, optical couplers 2, 5, 8, 21, 23, 30, a light pulse generation unit 3, optical switches 4, 22, an optical intensity/polarization adjustment unit 6, optical circulators 7, 12, optical connectors 9, 26, 27, 28, a first automatic temperature control unit (hereinafter referred to as the "first ATC") 10, a first automatic frequency control unit (hereinafter referred to as the "first AFC") 11, a control processing unit 13, a strain and temperature detector 14, a detection optical fiber 15, a temperature detection unit 16, a reference optical fiber 17, a second automatic temperature control unit (hereinafter referred to as the "second ATC") 18, a second automatic frequency control unit (hereinafter referred to as the "second AFC") 19, a second light source 20, an optical intensity adjustment unit 24, and 1×2 optical switches 25, 29, 31.

The first and second light sources 1, 20 are respectively light source devices that generate and output continuous light of a predetermined frequency by being maintained approximately constant at a predetermined temperature which is set in advance by the first and second ATCs 10, 18, and by being maintained approximately constant at a predetermined frequency which is set in advance by the first and second AFCs 11, 19. An output terminal (outgoing terminal) of the first light source 1 is optically coupled to an input terminal (incoming terminal) of the optical coupler 2. An output terminal (outgoing terminal) of the second light source 20 is optically coupled to an input terminal (incoming terminal) of the optical coupler 21.

The first and second light sources 1, 20 are respectively configured by including, for example, a light-emitting element, a temperature detection element (for example, a thermistor or the like) disposed in the vicinity of the light-emitting element and which detects the temperature of the light-emitting element, a first light-receiving element which receives one of the lights branched with an optical coupler (for example, a half mirror or the like), which branches a back light output from the rear of the light-emitting element into two, via a Fabry-perotetalon Filter as a periodic filter, a second light-receiving element which receives the other light branched with the optical coupler, a temperature adjustment element, and a substrate on which the foregoing light-emitting element, temperature detection element, optical coupler, first and second light-receiving element, Fabry-perotetalon Filter and temperature adjustment element are disposed.

The light-emitting element is an element capable of emitting light of a predetermined frequency with a narrow line width, and changing the oscillation wavelength (oscillation frequency) by changing the element temperature or drive current, and, for example, it is a wavelength variable semiconductor laser (frequency variable semiconductor laser) such as a multi-quantum well structure DFB laser or a variable wavelength distribution Bragg reflector laser. Accordingly, the first light source 1 also functions as a frequency variable light source.

The respective temperature detection elements in the first and second light sources 1, 20 respectively output the respective detected temperatures to the first and second ATCs 10, 18. The first and second light-receiving elements in the first and second light sources 1, 20 include, for example, a photoelectric conversion element such as a photodiode, and respectively output the respective light reception outputs according to the respective light reception optical intensities to the first and second AFCs 11, 19. The temperature adjustment element is a component for adjusting the temperature of the substrate by generating heat or absorbing heat, and, for example, is configured by including a thermoelectric conversion element such as a Peltier element or a Seebeck element.

The first and second ATCs 10, 18 are respectively circuits which automatically maintain the temperature of the respective substrates approximately constant at a predetermined temperature by controlling the respective temperature adjustment elements based on the respective detected temperatures of the respective temperature detection elements in the first and second light sources 1, 20 according to the control of the control processing unit 13. The temperature of the respective light-emitting elements in the first and second light sources 1, 20 is thereby maintained approximately constant at a predetermined temperature. Thus, if the frequency of the light emitted by the light-emitting element has temperature dependency, such temperature dependency is suppressed.

The first and second AFCs 11, 19 are respectively circuits which automatically maintain the frequency of the light emitted by the respective light-emitting elements approximately constant at a predetermined frequency and sweep the frequency of the light in a predetermined frequency range by controlling the respective light-emitting elements based on the respective light reception outputs of the first and second light-receiving elements in the first and second light sources 1, 20 according to the control of the control processing unit 13.

The optical coupler, the Fabry-perotetalon Filter, and the first and second light-receiving element in the first and second light sources 1, 20, and the first and second AFCs 11, 19 respectively configure a so-called wavelength locker which approximately fixes the wavelength (frequency) of the light emitted by the light-emitting element in the first and second light sources 1, 20.

The optical couplers 2, 5, 21, 23 are optical components which respectively distribute the incident light that entered from one input terminal into two lights and respectively output such two lights to two output terminals. The optical coupler 8 is an optical component which outputs the incident light that entered from one input terminal of the two input terminals to one output terminal, and outputs the incident light that entered from the other input terminal to the foregoing output terminal. The optical coupler 30 is an optical component which couples the two incident lights that entered from the two input terminals and outputs the coupled light from the two output terminals. As the optical couplers 2, 5, 21, 23, 8, 30, for example, a micro-optical element-type optical branch coupler such as a half mirror, or an optical fiber-type optical branch coupler or optical waveguide-type optical branch coupler of a fused fiber can be used.

One output terminal of the optical coupler 2 is optically coupled to the input terminal of the light pulse generation unit 3, and the other output terminal is optically coupled to the input terminal of the 1×2 optical switch 31. One output terminal of the optical coupler 5 is optically coupled to the input terminal of the optical intensity/polarization adjustment unit 6, and the other output terminal is optically coupled to the input terminal of the strain and temperature detector 14. One output terminal of the optical coupler 21 is optically coupled to the input terminal of the optical switch 22, and the other output terminal is optically coupled to the other end of the reference optical fiber 17 via the optical connector 28. One output terminal of the optical coupler 23 is optically coupled to the input terminal of the optical intensity adjustment unit 24, and the other output terminal is optically coupled to the input terminal of the strain and temperature detector 14. One input terminal of the optical coupler 8 is optically coupled to the second terminal of the optical circulator 7, the other input terminal is optically coupled to the other output terminal of the 1×2 optical switch 25, and the output terminal is optically connected to one end of the detection optical fiber 15 via the optical connector 9. One input terminal of the optical coupler 30 is optically coupled to the other output terminal of the 1×2 optical switch 31, the other input terminal is optically coupled to one output terminal of the 1×2 optical switch 29, and the two output terminals are optically coupled to the input terminal of the strain and temperature detector 14.

The light pulse generation unit 3 is a device into which the continuous light output from the first light source 1 enters, and which generates a main light pulse and a sub light pulse as the pump light from the foregoing continuous light. The main light pulse is a light pulse using a spread spectrum system. As the spread spectrum system, used may be, for example, a frequency chirp system which changes the frequency, a phase modulation system which modulates the phase, or a hybrid system which combines the foregoing frequency chirp system and the phase modulation system.

As the frequency chirp system, for example, a system of changing the frequency monotonously; for instance, changing the frequency linearly may be used. As the phase modulation system, for example, a system of modulating the phase using a PN sequence may be used. The PN sequence is a pseudo-random number sequence, and, as the PN sequence, for example, an M sequence (maximal-length sequences), a Gold sequence or the like may be used. The M sequence can be generated with a circuit configured by including a multi-step shift register, and a logic circuit that feeds back to the shift register the logical connection of the respective states in the respective steps of such multiple steps. Moreover, if Mi represents a sequence in which 0 of the M sequence generated with the nth primitive polynomials $F1(x)$ and $F2(x)$ is corresponded to −1 and Mj represents a sequence in which 1 of the M sequence is corresponded to +1, the Gold sequence can be generated based on the product Mi·Mj of the two. Moreover, a Golay code sequence can be used as the pseudo-random number sequence of the phase modulation system. The Golay code sequence possesses superior characteristics where the side lobe of the autocorrelation function becomes exactly 0. The sub light pulse is a non-modulated light pulse that has not been modulated, and the maximum optical intensity thereof is lower than the optical intensity of the main light pulse, and the pulse width is sufficiently longer than the life duration of the acoustic phonon.

The light pulse generation unit 3 generates the sub light pulse and the main light pulse such that the main light pulse does not enter the detection optical fiber 15 temporally before the sub light pulse in the Brillouin optical time domain analysis (BOTDA) of this embodiment according to the control of the control processing unit 13. The sub light pulse and the main light pulse as the pump light generated by the light pulse generation unit 3 are described later.

The optical switches 4, 22 are optical components which turn ON/OFF the light between the input terminal and the output terminal according to the control of the control processing unit 13. Light is transmitted when it is ON and light is blocked when it is OFF. As the optical switches 4, 22 in this embodiment, for example, an optical intensity modular such as an MZ optical modulator or a semiconductor electroabsorption-type optical modulator which modulates the optical intensity of the incident light is used. The optical switches 4, 22 include a driver circuit which is controlled by the control processing unit 13 and which drives the optical intensity modulator. The driver circuit is configured by including a DC power source which generates a DC voltage signal for turning OFF the optical intensity modulator in a normal state, a pulse generator which generates a voltage pulse for turning ON the optical intensity modulator that is normally turned OFF, and a timing generator which controls the timing of generating the voltage pulse. The output terminal of the optical switch 4 is optically coupled to the input terminal of the optical coupler 5. The output terminal of the optical switch 22 is optically coupled to the input terminal of the optical coupler 23.

The optical intensity/polarization adjustment unit 6 is a component that is controlled by the control processing unit 13, which adjusts the optical intensity of the incident light, and randomly changes and outputs the polarization plane of the incident light. The output terminal of the optical intensity/polarization adjustment unit 6 is optically coupled to the first terminal of the optical circulator 7. The optical intensity/polarization adjustment unit 6 is configured by including, for example, a variable optical attenuator capable of attenuating and outputting the optical intensity of the incident light and changing the attenuation amount thereof, and a polarization controller capable of randomly changing and outputting the polarization plane of the incident light. The optical intensity/polarization adjustment unit 6 is shared in the measurement of the stimulated Brillouin scattered light and the Rayleigh backscattered light, and randomly changes the polarization plane of the light.

The optical circulators 7, 12 are irreversible optical components in which the incident light and the outgoing light have a recurrence relation in their terminal numbers. Specifically, light that enters the first terminal is output from the second terminal and is not output from the third terminal, light that enters the second terminal is output from the third terminal and is not output from the first terminal, and light that enters the third terminal is output from the first terminal and not output from the second terminal. The first terminal of the optical circulator 7 is optically coupled to the output terminal of the optical intensity/polarization adjustment unit 6, the second terminal is optically coupled to one input terminal of the optical coupler 8, and the third terminal is optically coupled to the input terminal of the 1×2 optical switch 29. The first terminal of the optical circulator 12 is optically coupled to one output terminal of the 1×2 optical switch 31, the second terminal is optically coupled to one end of the reference optical fiber 17 via the optical connector 27, and the third terminal is optically coupled to the input terminal of the strain and temperature detector 14.

The optical connectors 9, 26, 27, 28 are optical components for optically coupling the optical fibers, or the optical component and the optical fiber.

The optical intensity adjustment unit 24 is a component which is controlled by the control processing unit 13 and which adjusts and outputs the optical intensity of the incident light. The output terminal of the optical intensity adjustment unit 24 is optically coupled to the input terminal of the optical switch 25. The optical intensity adjustment unit 24 is configured by including, for example, a variable optical attenuator which attenuates and outputs the optical intensity of the incident light, and an optical isolator which transmits light only in one direction from the input terminal to the output terminal. The incident light that enters the optical intensity adjustment unit 24 is output via the optical isolator upon its optical intensity being adjusted to a predetermined optical intensity by the variable optical attenuator. The optical isolator plays the role of preventing the propagation of the reflected light generated in the connections and the like of the respective optical components in the distributed optical fiber sensor FS and the propagation of the sub light pulse and the main light pulse to the second light source 20.

The 1×2 optical switches 25, 29, 31 are optical switches with 1 input and 2 outputs which output, from one of two output terminals, the light that entered from the input terminal by switching the optical path, and, for example, a mechanical optical switch or an optical waveguide switch can be used.

One output terminal of the 1×2 optical switch 25 is optically coupled to the other input terminal of the optical coupler 8, and the other output terminal is optically coupled to the other end of the detection optical fiber 15 via the optical connector 26. When performing the operation with the first mode (measurement of both ends) of the Brillouin optical time domain analysis (BOTDA) according to the control (or manual operation) of the control processing unit 13, the 1×2 optical switch 25 is switched so that the light that entered from the input terminal enters the other end of the detection optical fiber 15 via the optical connector 26, and, when performing the operation with the second mode (measurement of one end) of the Brillouin optical time domain analysis (BOTDA), the 1×2 optical switch 25 is switched so that the light that entered from the input terminal enters one end of the detection optical fiber 15 via the optical coupler 8 and the optical connector 9.

One output terminal of the 1×2 optical switch 29 is optically coupled to the other input terminal of the optical coupler 30, and the other output terminal is optically coupled to the strain and temperature detector 14. When performing the operation with the first mode of the Brillouin optical time domain analysis (BOTDA) or the second mode of the Brillouin optical time domain analysis (BOTDA) according to the control (or manual operation) of the control processing unit 13, the 1×2 optical switch 29 is switched so that the light that entered from the input terminal enters the strain and temperature detector 14, and, when performing the operation as a coherent optical time domain reflectometer (COTDR) using the Rayleigh scattering phenomenon, the 1×2 optical switch 29 is switched so that the light that entered from the input terminal enters the other input terminal of the optical coupler 30.

One output terminal of the 1×2 optical switch 31 is optically coupled to the first terminal of the optical circulator 12, and the other output terminal is optically coupled to one input terminal of the optical coupler 30. When performing the operation with the first mode of the Brillouin optical time domain analysis (BOTDA) or the second mode of the Brillouin optical time domain analysis (BOTDA) according to the control (or manual operation) of the control processing unit 13, the 1×2 optical switch 31 is switched so that the light that entered from the input terminal enters the optical circulator 12, and, when performing the operation as a coherent optical time domain reflectometer (COTDR) using the Rayleigh scattering phenomenon, the 1×2 optical switch 31 is switched so that the light that entered from the input terminal enters one input terminal of the optical coupler 30.

The detection optical fiber 15 is an optical fiber for use as a sensor which detects the strain and temperature, and, with the BOTDA, the sub light pulse and the main light pulse and the continuous light enter the detection optical fiber 15, and light that is subject to the action of the stimulated Brillouin scattering phenomenon is output therefrom. Moreover, when using the Rayleigh scattering phenomenon, pulsed light enters the detection optical fiber 15, and light that is subject to the action of the Rayleigh scattering phenomenon is output therefrom. Here, when measuring the strain and temperature generated in an object to be measured such as piping, oil field tubulars, bridge, tunnel, dam, building or other structures or the ground, the detection optical fiber 15 is fixed to the object to be measured with an adhesive, a fixing member or the like.

The reference optical fiber 17 is an optical fiber that is used for adjusting the frequency of the respective lights that are respectively output from the first and second light sources 1, 20, and is an optical fiber in which the relation of the frequency difference in the first and second lights that cause the stimulated Brillouin scattering phenomenon and the optical intensity of the light pertaining to the stimulated Brillouin scattering phenomenon is known in advance. Moreover, the reference optical fiber 17 may also be used for adjusting the light that is used for measuring the Rayleigh backscattered light.

The temperature detection unit 16 is a circuit for detecting the temperature of the reference optical fiber 17, and outputs the detected temperature to the control processing unit 13.

The strain and temperature detector 14 is configured by including a light-receiving element, an optical switch, an amplification circuit, an A/D converter, a signal processing circuit, a spectrum analyzer, a computer and the like. The strain and temperature detector 14 controls the respective components of the distributed optical fiber sensor FS by inputting and outputting signals to and from the control processing unit 13. The strain and temperature detector 14 obtains the optical intensity of the light pertaining to the stimulated Brillouin scattering phenomenon that entered the input terminal via the optical connector 27 and the optical circulator 12 and which was output from the reference optical fiber 17, and outputs the obtained optical intensity to the control processing unit 13.

Moreover, the strain and temperature detector 14 controls the respective components of the distributed optical fiber sensor FS by inputting and outputting signals to and from the control processing unit 13, the 1×2 optical switch 29 couples the optical circulator 7 and the strain and temperature detector 14, and the light pertaining to the stimulated Brillouin scattering phenomenon enters the light-receiving element with one input terminal for the stimulated Brillouin scattered light in the strain and temperature detector 14. The strain and temperature detector 14 obtains the Brillouin spectrum of the respective area portions of the detection optical fiber 15 in the longitudinal direction of the detection optical fiber 15 by connecting the light-receiving element for the stimulated Brillouin scattered light and the amplification circuit with an internal switch, and detecting the light pertaining to the stimulated Brillouin scattering phenomenon received in predetermined sampling intervals, and obtains the Brillouin frequency shift amount of the respective area portions based on the Brillouin spectrum of each of the obtained area portions.

Moreover, the strain and temperature detector 14 controls the respective components of the distributed optical fiber sensor FS by inputting and outputting signals to and from the control processing unit 13, the 1×2 optical switch 29 connects the optical circulator 7 and the optical coupler 30, and the light pertaining to the Rayleigh backscattering phenomenon enters the light-receiving element with two input terminals for the Rayleigh backscattered light in the strain and temperature detector 14 via the optical coupler 30. The strain and temperature detector 14 obtains the Rayleigh spectrum of the respective area portions of the detection optical fiber 15 in the longitudinal direction of the detection optical fiber 15 by connecting the light-receiving element for the Rayleigh backscattered light and the amplification circuit with an internal switch, and detecting the light pertaining to the Rayleigh backscattering phenomenon received in predetermined sampling intervals, and obtains the Rayleigh frequency shift amount of the respective area portions based on the Rayleigh spectrum of each of the obtained area portions.

In addition, the strain and temperature detector 14 simultaneously and independently detects the strain distribution and the temperature distribution of the detection optical fiber 15 from the Brillouin frequency shift amount and the Rayleigh frequency shift amount obtained as described above.

The respective incident lights that entered from the respective input terminals of the strain and temperature detector 14 are respectively converted into an electric signal according to the amount of received light by the light-receiving element which performs photoelectric conversion. The incident light that entered as light pertaining to the stimulated Brillouin scattering phenomenon is directly detected as a result of being converted into an electric signal by the light-receiving element, filtered with a matched filter, converted into a digital electric signal by an A/D converter, and used for obtaining the Brillouin spectrum. The incident light that entered as light pertaining to the Rayleigh backscattering phenomenon is directly detected as a result of being converted into an electric signal by the light-receiving circuit, filtered with a matched filter, converted into a digital electric signal by an A/D converter, and used for obtaining the Rayleigh spectrum. Moreover, as needed, the electric signal is amplified by an amplification circuit prior to being digitally converted.

The control processing unit 13 includes, for example, a microprocessor, a working memory, and a memory for storing various data required for measuring the distribution of the strain and temperature of the detection optical fiber 15 with high spatial resolution. The control processing unit 13 is an electronic circuit which controls the first and second light sources 1, 20, the first and second ATCs 10, 18, the first and second AFCs 11, 19, the light pulse generation unit 3, the optical switches 4, 22, the optical intensity/polarization adjustment unit 6, the 1×2 optical switches 25, 29, 31, and the optical intensity adjustment unit 24 so as to measure the distribution of the strain and temperature of the detection optical fiber 15 in the longitudinal direction of the detection optical fiber 15 with high spatial resolution and at a great distance by inputting and outputting signals to and from the strain and temperature detector 14.

The control processing unit 13 functionally includes a storage unit which stores in advance the relation of the frequency difference in the first and second lights that cause the stimulated Brillouin scattering phenomenon and the optical intensity of the light pertaining to the stimulated Brillouin scattering phenomenon in the reference optical fiber 17, and a frequency setting unit for controlling the first AFC 11 and/or the second AFC 19 so that the frequency difference of the respective lights emitted by the first and second light-emitting elements in the first and second light sources 1, 20 based on the optical intensity of the light pertaining to the stimulated Brillouin scattering phenomenon obtained by the strain and temperature detector 14 and the foregoing known relation in the reference optical fiber 17 becomes a predetermined frequency difference that is set in advance. Moreover, the control processing unit 13 functionally includes a frequency setting unit for controlling the first AFC 11 so as to output light that causes the Rayleigh backscattering phenomenon in the reference optical fiber 17.

Note that the first and second light sources 1, 20, the first and second ATCs 10, 18, the first and second AFCs 11, 19, the optical intensity/polarization adjustment unit 6, the optical intensity adjustment unit 24 and the optical intensity modulator are described in the Brochure of International Publication No. 2006/001071.

The Brillouin frequency shift in the case of using the spread spectrum system for the light that enters the detection optical fiber is now explained.

The spread spectrum system or the pulse compression system is used for extending the measurable distance in the so-called radar field. These systems detect the distance to the target object by scattering the spectrum of the pulse by using frequency modulation or phase modulation within the pulse that is radiated into open space for detecting the target object, and performing demodulation referred to as pulse compression to the reflected wave that was reflected off the target object. It is thereby possible to increase the energy of the pulse and extend the measurable distance. A spectral spread is to intentionally broaden the bandwidth to be broader than the bandwidth that is fundamentally required for sending signals.

When applying this spread spectrum system to the BOTDA or the BOTDR, since the Brillouin frequency shift will occur via a nonlinear process, if the spectrum of the light pulse is broadened (scattered), this foremost causes the spectrum of the excited acoustic phonon to broaden, and second causes the spectrum in the time-series signal of the reflected wave for each frequency to broaden, thereby causing the double broadening of the spectrum. Thus, it is not possible to simply apply the spectral spread code to the BOTDA or the BOTDR. Thus, the present inventors discovered that, as analyzed below, the spread spectrum system can be applied to the BOTDA or the BOTDR by configuring the light pulse from a main light pulse and a sub light pulse, and using the spread spectrum system for the main light pulse.

Although the case of applying this to the BOTDA is explained below, similar analysis can be performed for the BOTDR.

With the BOTDA, pump light enters from one end (z=0) of the detection optical fiber, probe light of a frequency that is different from the frequency of the pump light enters from the other end, and backscattering of the excited acoustic phonon is observed at the end point of z=0. The Brillouin gain spectrum (BGS) is the increment of power of the probe light.

Foremost, the pump light $A_p(0, t)$ is made to be a light pulse in which the complex envelope has a shape as represented by Formula (1).

$$A_p(0,t) = \sqrt{P_p} f(t) \tag{1}$$

Here, $P_p$ represents the power of the pump light, and $f(t)$ is a function representing the amplitude of the pump light at time t, and is normalized so that its maximum absolute value becomes 1.

Moreover, when defining the function with Formula (2), the Fourier transformation thereof is represented by Formula (3). In the foregoing case, the Brillouin gain spectrum $V(t, \nu)$ is a two-dimensional convolution, and represented by Formula (4). The first term on the right-hand side of Formula (4) is the time-varying Lorentz spectrum.

$$r(t, \tau) = \begin{cases} f(t)f*(t-\tau), & \tau \geq 0 \\ f*(t)f(t+\tau), & \tau < 0 \end{cases} \tag{2}$$

$$\psi(t, \nu) = \int_{-\infty}^{\infty} r(t, \tau) e^{-2\pi i \nu \tau} d\tau \tag{3}$$

$$V(t, \nu) = \gamma G\left(\nu - \nu_B\left(\frac{v_g t}{2}\right)\right) \overset{t,\nu}{*} \psi(t, \nu) \tag{4}$$

Here, the superscript * represents that it is complex conjugate, and i is a complex unit ($i^2 = -1$). Moreover, $\gamma$ is a gain coefficient, and $\nu_B(z)$ is the Brillouin frequency shift at position z. In addition, $G(\nu)$ is the Lorentz spectrum, and $v_g$ is the group velocity of the pump light. The operator * represents convulsion, and its superscripts t, $\nu$ represent that it is a two-dimensional convulsion regarding these variables. Note that the indication of the multiplication operator · has been omitted.

Here, ideally, the time-varying Lorentz spectrum of the first term on the right-hand side of Formula (4) itself is observed, but in reality the Brillouin gain spectrum obscured by the convulsion with the point-spread function $\psi(t, \nu)$ is observed. Thus, it is necessary for the point-spread function $\psi(t, \nu)$ to be a two-dimensional delta function or in the vicinity thereof. Thus, preferably, $\psi(t, \nu) \approx \delta(t)\delta(\nu)$.

Here, the pump light is configured from a main light pulse $f_1(t)$ and a sub light pulse $f_2(t)$. Specifically, the amplitude $f(t)$ of the pump light becomes Formula (5).

$$f(t) = f_1(t) + f_2(t) \tag{5}$$

The sub light pulse functions to excite the acoustic phonon for the main light pulse. The pulse width $D_{sub}$ of the sub light pulse is set to be at least sufficiently longer in comparison to the life duration of the acoustic phonon. The life duration of the acoustic phonon is generally around 5 ns.

The main light pulse functions to deliver the energy that was scattered with the acoustic phonon to the probe light. The main light pulse is divided into a plurality of cells for a predetermined duration in the time direction, and is made into a wide band by using the spread spectrum system. A wide band is a reference in comparison to the spectrum line width (approximately 30 to 40 MHz) of the acoustic phonon. The duration of the cells determines the spatial resolution of the BOTDA, and the reciprocal thereof becomes the width of the spectrum. For example, if the cell width (cell duration) is 0.1 ns, the spatial resolution will be 1 cm, and the spectrum width will be 10 GHz. The pulse width D of the main light pulse determines the amount of energy to be given to the pump light for extending the measurable distance. Here, since the spatial resolution of the BOTDA is determined by the cell width of the main light pulse as described above, the pulse width D of the main light pulse can be set independently from the spatial resolution of the BOTDA. Accordingly, the pulse width D of the main light pulse can be set arbitrarily according to the intended measurable distance. Thus, the measurable distance can be extended farther in comparison to conventional technology.

When the pump light is configured with two components as described above, the Brillouin gain spectrum V(t, ν) is configured from three components, and represented by Formula (6) and Formula (7) (Formula (7-1) to Formula (7-3)).

$$V(t, \nu) = V_{1,1}(t, \nu) + V_{1,2}(t, \nu) + V_{2,2}(t, \nu) \quad (6)$$

$$V_{1,1}(t, \nu) = \gamma G\left(\nu - \nu_B\left(\frac{v_g t}{2}\right)\right) \overset{t,\nu}{*} \psi_{1,1}(t, \nu) \quad (7\text{-}1)$$

$$V_{1,2}(t, \nu) = \gamma G\left(\nu - \nu_B\left(\frac{v_g t}{2}\right)\right) \overset{t,\nu}{*} \psi_{1,2}(t, \nu) \quad (7\text{-}2)$$

$$V_{2,2}(t, \nu) = \gamma G\left(\nu - \nu_B\left(\frac{v_g t}{2}\right)\right) \overset{t,\nu}{*} \psi_{2,2}(t, \nu) \quad (7\text{-}3)$$

In addition, the point-spread function ψ(t, ν) is represented by Formula (8), and, since the pump light is configured from the main light pulse and the sub light pulse, the point-spread function ψ(t, ν) is represented by Formula (9) and Formula (10).

$$\psi(t,\nu) = f(t)\int_{-\infty}^{\infty} f(t-|\tau|)e^{-2\pi i \nu \tau} d\tau * h(t) \quad (8)$$

$$\psi(t,\nu) = \psi_{1,1}(t,\nu) + \psi_{1,2}(t,\nu) + \psi_{2,1}(t,\nu) + \psi_{2,2}(t,\nu) \quad (9)$$

$$\psi_{1,1}(t,\nu) = f_1(t)\int_{-\infty}^{\infty} f_1(t-|\tau|)e^{-2\pi i \nu \tau} d\tau * h(t) \quad (10\text{-}1)$$

$$\psi_{1,2}(t,\nu) = f_1(t)\int_{-\infty}^{\infty} f_2(t-|\tau|)e^{-2\pi i \nu \tau} d\tau * h(t) \quad (10\text{-}2)$$

$$\psi_{2,1}(t,\nu) = f_2(t)\int_{-\infty}^{\infty} f_1(t-|\tau|)e^{-2\pi i \nu \tau} d\tau * h(t) \quad (10\text{-}3)$$

$$\psi_{2,2}(t,\nu) = f_2(t)\int_{-\infty}^{\infty} f_1(t-|\tau|)e^{-2\pi i \nu \tau} d\tau * h(t) \quad (10\text{-}4)$$

Here, in the spread spectrum system, a matched filter applied to that spread spectrum system is used for the demodulation thereof, and the impulse response h(t) of the matched filter will be $f_1(D-t)(h(t)=f_1(D-t))$. The matched filter is used for acquiring the convulsion with the input of the matched filter by temporally inverting the signal (when using a code sequence for the spectral spread, then that code) that was used for the spectral spread.

Since the main light pulse uses the spread spectrum system, and the sub light pulse is non-modulated and its pulse width is sufficiently long, the component $\psi_{1,2}(t, \nu)$ of the point-spread function ψ(t, ν) can be approximated as shown in Formula (11), and becomes the favorable the form described above.

$$\psi_{1,2}(t,\nu) \sim D_{sub} C_p \delta(\nu) f_1(t) * h(t) \sim DD_{sub} C_p \delta(t)\delta(\nu) \quad (11)$$

Here, $C_p$ is the amplitude ratio of the main light pulse and the sub light pulse.

Accordingly, the corresponding Brillouin gain spectrum is represented by Formula (12).

$$V_{1,2}(t, \nu) = \gamma G\left(\nu - \nu_B\left(\frac{v_g t}{2}\right)\right) \overset{t,\nu}{*} \psi_{1,2}(t, \nu) \sim \gamma DD_{sub} C_P G\left(\nu - \nu_B\left(\frac{v_g t}{2}\right)\right) \quad (12)$$

Note that the other components $V_{1,1}(t, \nu)$ and $V_{2,1}(t, \nu)$ in the Brillouin gain spectrum V(t, ν) become a flat spectrum when the main light pulse is subject to a spectral spread with a pseudo-random number. Moreover, the other component $V_{2,2}(t, \nu)$ is suppressed by the matched filter during demodulation.

Moreover, the components $V_{1,1}(t, \nu)$ and $V_{2,2}(t, \nu)$ in the Brillouin gain spectrum V(t, ν) can be extracted by measuring the Brillouin gain spectrum by configuring the pump light only with the main light pulse or configuring it only with the sub light pulse.

Based on the foregoing analysis, the distributed optical fiber sensor can independently set the spatial resolution and the measurable distance by configuring the light pulse to enter the detection optical fiber from two components; namely, the main light pulse using the spread spectrum system and the non-modulated sub light pulse. Thus, the distributed optical fiber sensor can extend the measurable distance and measure up to a farther distance while enabling the measurement of the strain and temperature with high spatial resolution.

Figure 2:
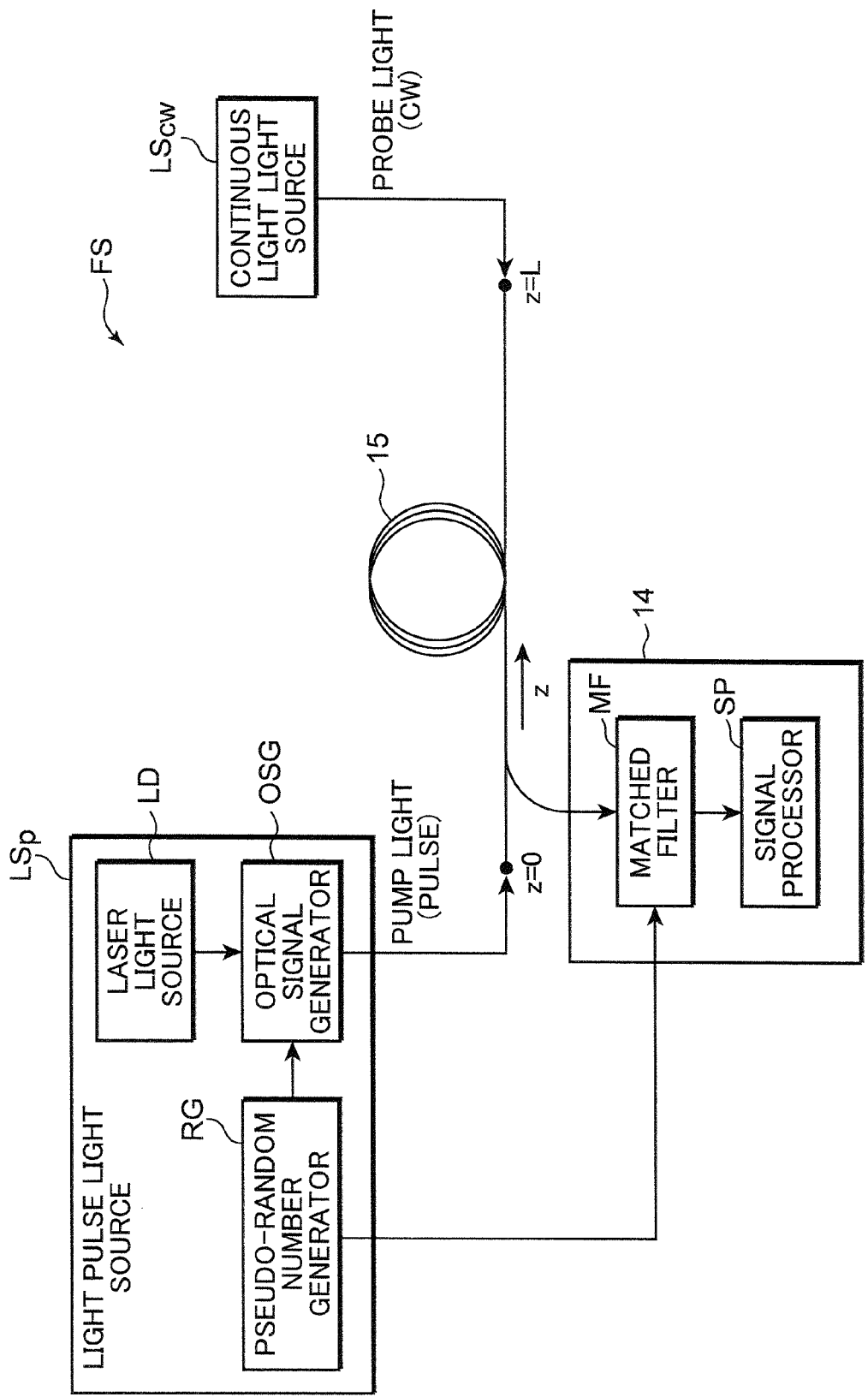
FIG. 2 is a block diagram showing the schematic configuration of the distributed optical fiber sensor in the case of operating the distributed optical fiber sensor shown in FIG. 1 based on the first mode.

The distributed optical fiber sensor FS shown in FIG. 1 functions as the BOTDA when measuring the Brillouin frequency shift amount, and operates as the first mode (measurement of both ends) by switching the 1×2 optical switches 25, 29, 31. FIG. 2 is a block diagram showing the schematic configuration of the distributed optical fiber sensor in the case of operating the distributed optical fiber sensor shown in FIG. 1 based on the first mode.

As shown in FIG. 2, during the measurement of both ends, the distributed optical fiber sensor FS causes the sub light pulse and the main light pulse generated by the light pulse light source $LS_p$ as the pump light to enter from one end of the detection optical fiber 15 for detecting the strain and temperature, and causes the continuous light generated by the continuous light light source $LS_{CW}$ as the probe light to enter from the other end of the detection optical fiber 15.

The distributed optical fiber sensor FS measures the Brillouin frequency shift amount by receiving the light pertaining to the stimulated Brillouin scattering phenomenon generated in the detection optical fiber 15 with the strain and temperature detector 14, and performing the Brillouin gain spectrum time domain analysis ($B^{Gain}$-OTDA) or the Brillouin loss spectrum time domain analysis ($B^{Loss}$-OTDA) with the strain and temperature detector 14.

In the light pulse light source $LS_p$, the main light pulse using the spread spectrum system is generated as a result of the laser beam output from the laser light source LD being subject to phase modulation with a pseudo-random number from the pseudo-random number generator RG in the optical signal generator OSG. The pseudo-random number generated by the pseudo-random number generator RG is notified to the strain and temperature detector 14 for demodulation. In the strain and temperature detector 14, the Brillouin frequency shift amount is measured as a result of the light pertaining to the stimulated Brillouin scattering phenomenon output from the detection optical fiber 15 being filtered with the matched filter MF according to the pseudo-random number from the pseudo-random number generator RG, and the signal processing of the BOTDA being performed by the signal processor SP.

Note that, in the ensuing explanation, the Brillouin gain spectrum time domain analysis or the Brillouin loss spectrum time domain analysis is abbreviated as the Brillouin optical time domain analysis as appropriate. In the Brillouin optical time domain analysis, the light pertaining to the stimulated Brillouin scattering phenomenon is light that was subject to the Brillouin amplification or attenuation.

Figure 3:
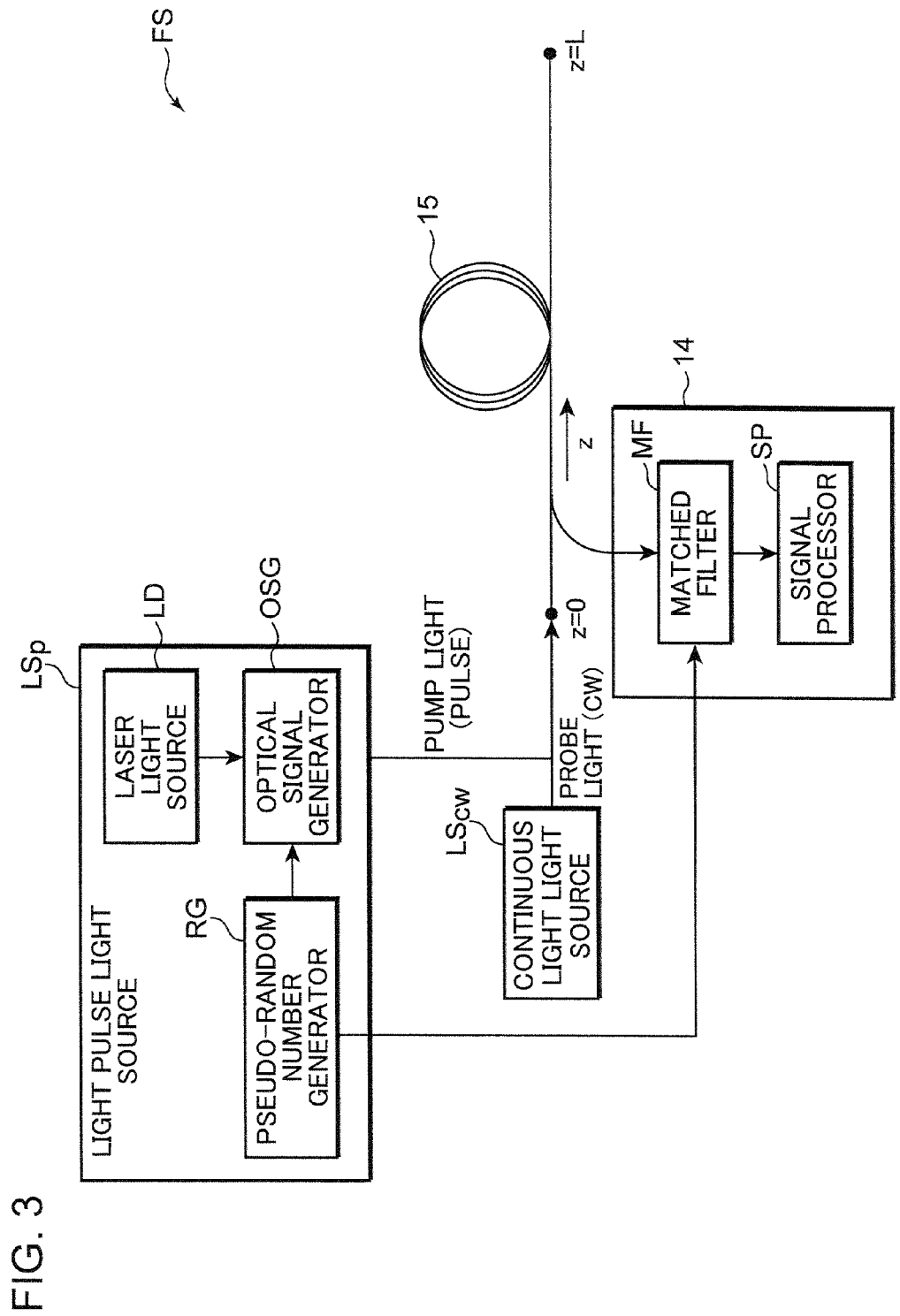
FIG. 3 is a block diagram showing the schematic configuration of the distributed optical fiber sensor in the case of operating the distributed optical fiber sensor shown in FIG. 1 based on the second mode.

Moreover, the distributed optical fiber sensor FS shown in FIG. 1 functions as the BOTDA when measuring the Brillouin frequency shift amount, and operates as the second mode (measurement of one end) by switching the optical switches 25, 29, 31. FIG. 3 is a block diagram showing the schematic configuration of the distributed optical fiber sensor in the case of operating the distributed optical fiber sensor shown in FIG. 1 based on the second mode.

As shown in FIG. 3, during the measurement of one end, the distributed optical fiber sensor FS causes the sub light pulse and the main light pulse generated by the light pulse light source $LS_p$ as the pump light and the continuous light generated by the continuous light light source $LS_{CW}$ as the probe light to enter from one end of the detection optical fiber 15. Note that the spread spectrum system is used for the main light pulse.

The distributed optical fiber sensor FS measures the Brillouin frequency shift amount by receiving the light pertaining to the stimulated Brillouin scattering phenomenon generated in the detection optical fiber 15 with the strain and temperature detector 14, and performing the Brillouin gain spectrum time domain analysis ($B^{Gain}$-OTDA) or the Brillouin loss spectrum time domain analysis ($B^{Loss}$-OTDA) with the strain and temperature detector 14.

The operation of the distributed optical fiber sensor FS is now explained. Foremost, upon starting the measurement, the respective frequencies of the respective continuous lights output from the first and second light sources 1, 20 are respective adjusted (calibrated) by using the reference optical fiber 17.

More specifically, the control processing unit 13 causes the first and second light sources 1, 20 to respectively emit the respective continuous lights at respective predetermined frequencies by respectively controlling the first ATC 10 and the first AFC 11, and the second ATC 18 and the second AFC 19, and causes the respective continuous lights to enter the reference optical fiber 17 in a mutually opposing manner. The continuous light from the first light source 1 and the continuous light from the second light source 20 generate a stimulated Brillouin scattering phenomenon in the reference optical fiber 17, and the light pertaining to the stimulated Brillouin scattering phenomenon enters the strain and temperature detector 14 from the reference optical fiber 17 via the optical circulator 12.

The strain and temperature detector 14 receives the light pertaining to the stimulated Brillouin scattering phenomenon, detects the optical intensity of the received light pertaining to the stimulated Brillouin scattering phenomenon, and notifies the detected optical intensity to the control processing unit 13. In the control processing unit 13, the relation of the frequency difference in the first and second lights that cause the stimulated Brillouin scattering phenomenon in the reference optical fiber 17 and the optical intensity of the light pertaining to the stimulated Brillouin scattering phenomenon is stored in advance in its storage unit. When the control processing unit 13 receives the foregoing notification, it obtains, from the foregoing relation, the reference optical intensity Pa corresponding to the predetermined frequency difference fa to be set by the frequency setting unit for the respective lights that are emitted by the first and second light-emitting elements in the first and second light sources 1, 20, and controls the first AFC 11 and the second AFC 19 so that the measured optical intensity Pd detected by the strain and temperature detector 14 coincided with the reference optical intensity Pa. The frequency difference of the respective lights that are emitted by the first and second light-emitting elements in the first and second light sources 1, 20 is thereby adjusted to the predetermined frequency difference fa to be set. Note that, in this embodiment, the optical intensity Pd is given as a voltage value that was subject to photoelectric conversion by the light-receiving element, and the reference optical intensity Pa becomes a voltage value corresponding to the reference optical intensity Pa.

Here, the relation of the frequency difference in the first and second lights that cause the stimulated Brillouin scattering phenomenon in the reference optical fiber 17 and the optical intensity of the light pertaining to the stimulated Brillouin scattering phenomenon generally has temperature dependency. In this embodiment, upon adjustment, the control processing unit 13 uses the temperature detection unit 16 to detect the temperature of the reference optical fiber 17, and corrects the foregoing relation in the reference optical fiber 17 according to the detected temperature. Thus, the adjustment can be performed with higher precision.

As a result of performing the foregoing operation, the respective frequencies of the respective continuous lights emitted from the first and second light sources 1, 20 are adjusted. This kind of adjustment may be performed each time the frequency is changed for the sweep upon obtaining the Brillouin spectrum from the perspective of further improving the measurement accuracy, or performed each time the strain and temperature are measured from the perspective of shortening the measurement time, or performed for each lapse of a predetermined period, or performed for each start-up of the distributed optical fiber sensor FS.

Figure 4:
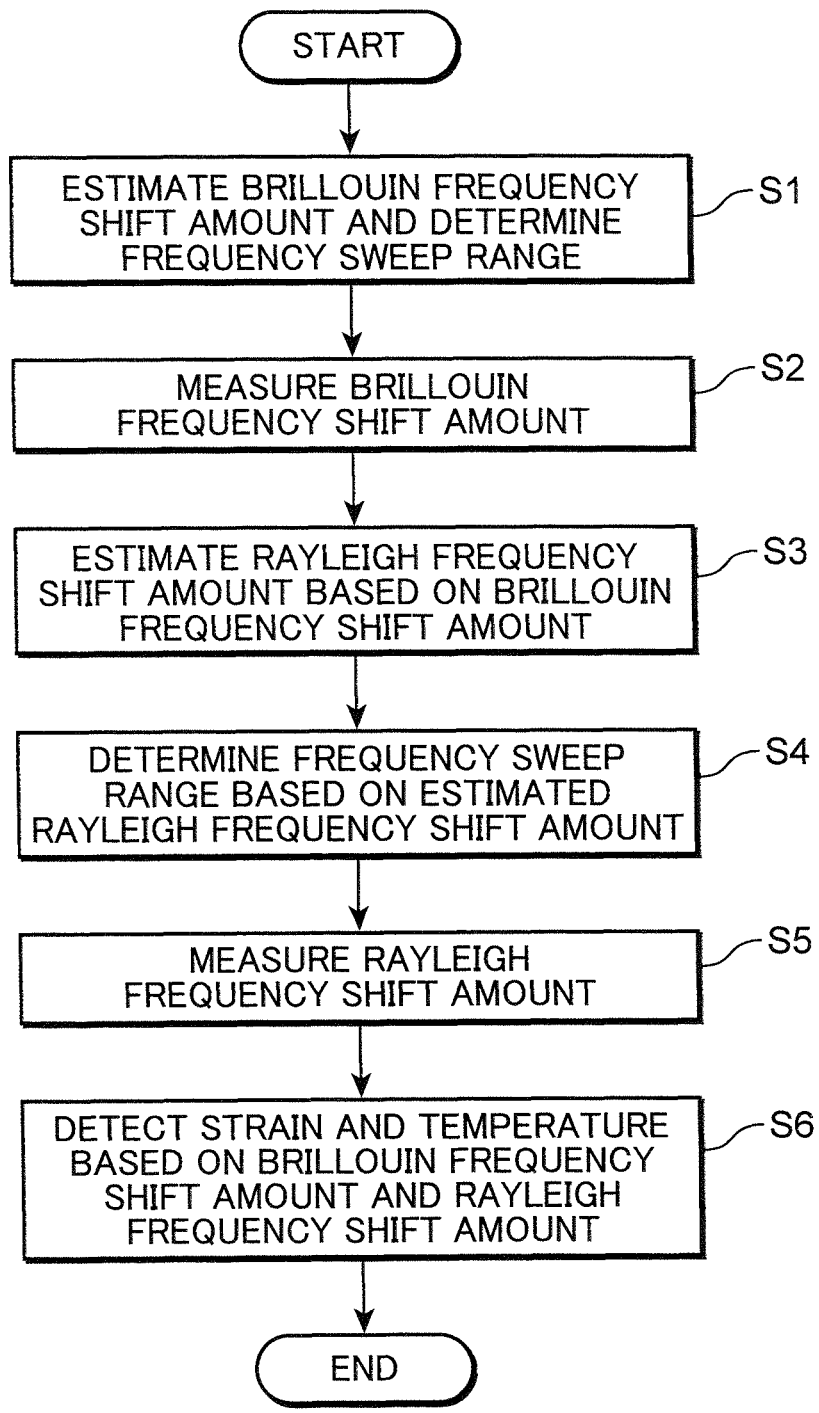
FIG. 4 is a flowchart explaining the operation of measuring the strain and temperature performed by the distributed optical fiber sensor shown in FIG. 1.

The operation of measuring the strain and temperature is now explained. FIG. 4 is a flowchart explaining the operation of measuring the strain and temperature performed by the distributed optical fiber sensor FS shown in FIG. 1.

Foremost, in step S1, the strain and temperature detector 14 estimates the Brillouin frequency shift amount Δvb, determines the frequency sweep range for measuring the Brillouin frequency shift amount Δvb, and commands the control processing unit 13 for emitting the respective continuous lights from the first and second light sources 1, 20 in the determined sweep range. The estimation of the Brillouin frequency shift amount Δvb in this case is performed, for example, based on the predicted maximum temperature variation and the maximum strain variation. Note that, since the frequency sweep range for measuring the Brillouin frequency shift amount is narrow, this frequency sweep range can be estimated easily.

Subsequently, in step S2, the strain and temperature detector 14 measures the Brillouin frequency shift amount Δvb. For example, the Brillouin frequency shift amount Δvb can be obtained based on the following processing.

Foremost, the control processing unit 13 causes the first and second light sources 1, 20 to respectively emit the respective continuous lights at respective predetermined frequencies by controlling the first ATC 10 and the first AFC 11, and the second ATC 18 and the second AFC 19. The continuous light output from the first light source 1 enters the light pulse generation unit 3 via the optical coupler 2, and the continuous light output from the second light source 20 enters the optical switch 22 via the optical coupler 21.

Subsequently, the control processing unit 13 generates a predetermined pump light (sub light pulse and main light pulse) by controlling the light pulse generation unit 3. More specifically, the control processing unit 13 generates a pump light, for example, by causing the light pulse generation unit 3 to operate as follows.

Figure 5:
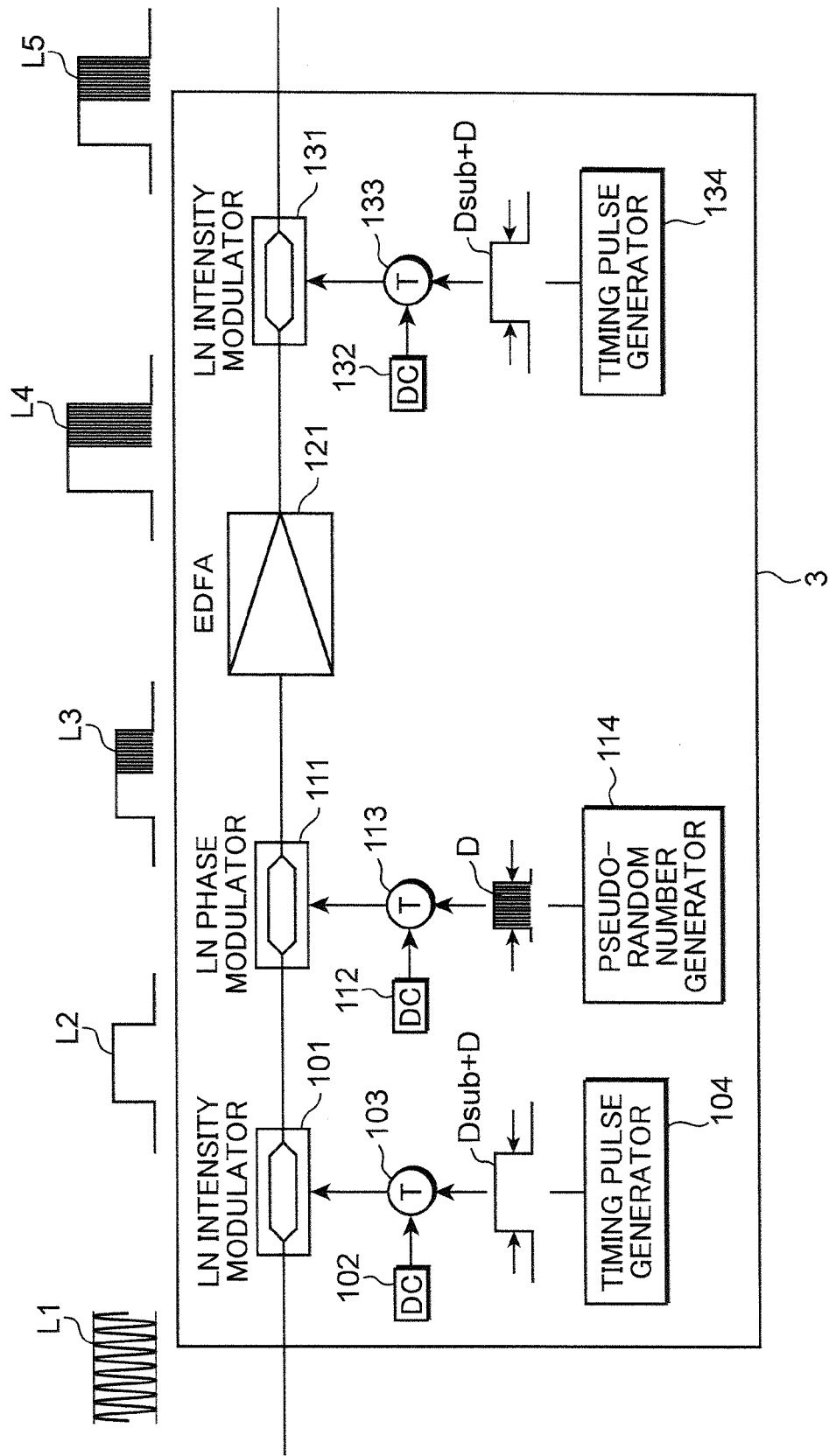
FIG. 5 is a diagram explaining the configuration and operation of the light pulse generation unit shown in FIG. 1.

FIG. 5 is a diagram explaining the configuration and operation of the light pulse generation unit 3 shown in FIG. 1. FIG. 6 is a diagram explaining the configuration of pump light (sub light pulse and main light pulse) and the matched filter, wherein FIG. 6(A) shows the configuration of the pump light and FIG. 6(B) shows the matched filter.

The light pulse generation unit 3 is configured by including, for example, as shown in FIG. 5, a LN intensity modulator 101 for modulating the optical intensity of the incident light, a DC power source 102, a multiplier 103 and a timing pulse generator 104 which configure a first drive circuit for driving the LN intensity modulator 101, a LN phase modulator 111 for modulating the phase of the incident light, a DC power source 112, a multiplier 113 and a pseudo-random number generator 114 which configure a second drive circuit for driving the LN phase modulator 111, an erbium-doped fiber amplifier (EDFA) 121, a LN intensity modulator 131 for modulating the optical intensity of the incident light, and a DC power source 132, a multiplier 133 and a timing pulse generator 134 which configure a third drive circuit for driving the LN intensity modulator 131.

The LN phase modulator 111 is a device that is configured, for example, by an optical waveguide and a signal electrode and a ground electrode being formed on a lithium niobate substrate having an electro-optic effect, and which modulates the phase of the incident light by using, as is, the phase change accompanying the refractive index change caused by the electro-optic effect that occurs as a result of applying a predetermined signal between both electrodes.

The LN intensity modulators 101, 131 are devices for modulating the optical intensity of the incident light by configuring, for example, a Mach-Zehnder interferometer and changing the phase change accompanying the refractive index change caused by the electro-optic effect to an intensity change. Note that, for the LN intensity modulators 101, 131 and the LN phase modulator 111, in substitute for the lithium niobate substrate, for example, other substrates having an electro-optic effect made of a solid solution of lithium tantalate or lithium niobate/lithium tantalate may be used.

In the first drive circuit, the DC power source 102 is a power source circuit which generates a DC voltage to be applied to the signal electrode of the LN intensity modulator 101 for performing intensity modulation, the timing pulse generator 104 is a pulse generation circuit which generates an operation timing pulse for causing the LN intensity modulator 101 to operate, and the multiplier 103 is a circuit which multiplies the DC voltage input from the DC power source 102 and the operation timing pulse input from the timing pulse generator 104, and outputs the DC voltage according to the operation timing pulse to the LN intensity modulator 101.

In the second drive circuit, the DC power source 112 is a power source circuit which generates a DC voltage to be applied to the signal electrode of the LN phase modulator 111 for performing phase modulation, the pseudo-random number generator 114 is a pseudo-random number generation circuit which generates a pseudo-random number at the operation timing for causing the LN phase modulator 111 to operate so as to modulate the incident light with the spread spectrum system, and the multiplier 113 is a circuit which multiplies the DC voltage input from the DC power source 112 and the pseudo-random number input from the pseudo-random number generator 114, and outputs the DC voltage according to the pseudo-random number to the phase modulator 111.

The EDFA 121 is an optical component that is configured by including an optical fiber doped with erbium, and amplifies and outputs the incident light. The EDFA 121 amplifies the incident light at a predetermined amplification ratio that is set in advance to achieve the optical intensity that is suitable for detecting the strain and temperature in the detection optical fiber 15. Consequently, if any loss occurs during the propagation from the first light source 1 to the detection optical fiber 15, such loss is also compensated, and measurement of a predetermined measurement range is thereby enabled.

In the third drive circuit, the DC power source 132 is a power source circuit which generates a DC voltage to be applied to the signal electrode of the LN intensity modulator 131 for causing the LN intensity modulator 131 to perform intensity modulation so as to realize ON/OFF control, the timing pulse generator 134 is a pulse generation circuit which generates an operation timing pulse for causing the LN intensity modulator 131 to operate, and the multiplier 133 is a circuit which multiplies the DC voltage input from the DC power source 132 and the operation timing pulse input from the timing pulse generator 134, and outputs the DC voltage according to the operation timing pulse to the LN intensity modulator 131.

As a result of operating this kind of light pulse generation unit 3, for example, a pump light having the configuration shown in FIG. 6A can be generated.

The pump light shown in FIG. 6A is configured from a main light pulse encoded with the spread spectrum system, and a non-modulated sub light pulse which temporally precedes the main light pulse without overlapping with the main light pulse. The main light pulse is divided into a plurality of cells in a predetermined duration (cell width), and, in this embodiment, the respective cells are modulated (encoded) with the M sequence binary code. The cell width is set according to the intended spatial resolution, and the pulse width of the main light pulse is set according to the intended measurement distance. Moreover, the sub light pulse is set to a pulse width capable of causing the acoustic phonon to completely rise, and, with the example shown in FIG. 6A, it has an optical intensity of the same level as the optical intensity of the main light pulse.

The sub light pulse and the main light pulse are temporally continuous in the example shown in FIG. 6A, but they may also be temporally separated. If they are temporally separated, preferably, the main light pulse is set to a time interval that works on the acoustic phonon before the acoustic phonon that was risen by the sub light pulse disappears. Since the life duration of the acoustic phonon is approximately 5 ns under normal circumstances, the time interval of the sub light pulse and the main light pulse is preferably within approximately 5 ns.

In order to generate the pump light having the configuration shown in FIG. 6A, in FIG. 5, foremost, the continuous light L1 output from the first light source 1 enters the LN intensity modulator 101 of the light pulse generation unit 3 via the optical coupler 2.

In the light pulse generation unit 3, at the generation timing of the pump light, an operation timing pulse of a pulse width ($D_{sub}$+D) corresponding to the pulse width $D_{sub}$ of the sub light pulse and the pulse width D of the main light pulse is output from the timing pulse generator 104 to the multiplier 103, multiplied with the DC voltage input from the DC power source 102, and the DC voltage of the pulse width ($D_{sub}$+D) is applied to the signal electrode of the LN intensity modulator 101. The LN intensity modulator 101 is thereby turned ON during the duration ($D_{sub}$+D) corresponding to its pulse width ($D_{sub}$+D) according to the operation timing pulse, and the continuous light L1 is output as the light pulse L2 of the pulse width ($D_{sub}$+D) by the LN intensity modulator 101.

Subsequently, in the light pulse generation unit 3, at the generation timing of the main light pulse, a pseudo-random number is sequentially output from the pseudo-random number generator 114 to the multiplier 113 at the temporal timing of the cell width during the duration D corresponding to the pulse width D of the main light pulse, multiplied with the DC voltage input from the DC power source 112, and the DC voltage that was modulated with the M sequence binary code is sequentially applied to the signal electrode of the LN phase modulator 111 at the temporal timing of the cell width during the duration D from the generation timing of the main light pulse.

Specifically, the DC voltage that was modulated with the M sequence binary code is a voltage value which causes the phase of the light output from the LN phase modulator 111 when the corresponding DC voltage is supplied to the LN phase modulator 111 in cases where the M sequence binary code is "+" and the phase of the light output from the LN phase modulator 111 when the corresponding DC voltage is supplied to the LN phase modulator 111 in cases where the M sequence binary code is "−" to mutually differ by 180 degrees. The light pulse L2 is thereby output as the light pulse L3 configured from a non-modulated portion (corresponds to the sub light pulse) and the portion that was modulated with the M sequence binary code (corresponds to the main light pulse) based on the LN phase modulator 111.

Subsequently, in the EDFA 121, the light pulse L3 is amplified until it becomes a predetermined optical intensity and then output as the light pulse L4.

In addition, in the light pulse generation unit 3, according to the generation timing of the pump light, the operation timing pulse of the pulse width ($D_{sub}$+D) corresponding to the pulse width $D_{sub}$ of the sub light pulse and the pulse width D of the main light pulse is output from the timing pulse generator 134 to the multiplier 133, multiplied with the DC voltage input from the DC power source 132, and the DC voltage of the pulse width ($D_{sub}$+D) is applied to the signal electrode of the LN intensity modulator 131. The light pulse L4 is thereby output as the pump light L5 configured from a non-modulated sub light pulse having the pulse width $D_{sub}$ and the main light pulse encoded with the spread spectrum system and having the pulse width D after noise such as amplified spontaneous emission (ASE) associated with the light pulse L4 at the EDFA 121 is removed with the LN intensity modulator 131.

Subsequently, the control processing unit 13 turns ON the optical switch 4 and the optical switch 22 according to the generation timing of the pump light (sub light pulse and main light pulse light pulse L4) in the light pulse generation unit 3. The control processing unit 13 notifies the generation timing of the pump light (sub light pulse and main light pulse) to the strain and temperature detector 14.

When the optical switch 4 is turned ON, the pump light (sub light pulse and main light pulse) enters the optical coupler 5 and is branched into two pump lights. One of the branched pump lights enters the optical intensity/polarization adjustment unit 6, the optical intensity thereof is adjusted by the optical intensity/polarization adjustment unit 6, the polarization direction thereof is adjusted randomly, and enters one end of the detection optical fiber 15 via the optical circulator 7, the optical coupler 8 and the optical connector 9. Meanwhile, the other sub light pulse and main light pulse branched by the optical coupler 5 enter the strain and temperature detector 14.

The strain and temperature detector 14 measures the spectrum of the pump light (sub light pulse and main light pulse), and notifies the frequency and optical intensity of the pump light to the control processing unit 13. When the control processing unit 13 receives the foregoing notification, it controls the first ATC 10, the first AFC 11 and the optical intensity/polarization adjustment unit 6 as needed in order to obtain the optimal measurement result.

Meanwhile, when the optical switch 22 is turned ON, the continuous light (probe light) enters the optical coupler 23, and is branched into two probe lights. One of the branched probe lights (continuous light) enters the optical intensity adjustment unit 24, the optical intensity thereof is adjusted by the optical intensity adjustment unit 24, and enters the 1×2 optical switch 25. The 1×2 optical switch 25 is switched so that, when the Brillouin optical time domain analysis (BOTDA) is performed based on the first mode, the light that entered from the input terminal enters the other end of the detection optical fiber 15 via the optical connector 26, and the probe light (continuous light) enters the other end of the detection optical fiber 15 via the optical connector 26.

Meanwhile, the 1×2 optical switch 25 is switched so that, when the Brillouin optical time domain analysis (BOTDA) is performed based on the second mode, the light that entered from the input terminal enters one end of the detection optical fiber 15 via the optical coupler 8 and the optical connector 9, and the probe light (continuous light) enters one end of the detection optical fiber 15 via the optical coupler 8 and the optical connector 9. Meanwhile, the other probe light (continuous light) that was branched by the optical coupler 23 enters the strain and temperature detector 14.

The strain and temperature detector 14 measures the spectrum of the probe light (continuous light), and notifies the frequency and optical intensity of the probe light to the control processing unit 13. When the control processing unit 13 receives the foregoing notification, it controls the second ATC 18, the second AFC 19 and the optical intensity adjustment unit 24 as needed in order to obtain the optimal measurement result.

With the Brillouin optical time domain analysis of the first mode, the pump light (sub light pulse and main light pulse) that entered from one end of the detection optical fiber 15 propagates from one end to the other end of the detection optical fiber 15 while generating the stimulated Brillouin scattering phenomenon with the probe light (continuous light) that entered from the other end of the detection optical fiber 15 and which propagates the detection optical fiber 15. With the Brillouin optical time domain analysis of the second mode, the pump light (sub light pulse and main light pulse) that entered from one end of the detection optical fiber 15 propagates from one end to the other end of the detection optical fiber 15 while generating the stimulated Brillouin scattering phenomenon with the probe light (continuous light) that entered from one end of the detection optical fiber 15 and which propagates the detection optical fiber 15 by reflecting off the other end of the detection optical fiber 15. The ON/OFF timing in the optical switch 4 and the optical switch 22 is adjusted by the control processing unit 13 based on the foregoing interaction of the pump light and the probe light.

The 1×2 optical switch 29 is switched so that, when the Brillouin optical time domain analysis (BOTDA) is performed based on the first mode or the second mode, the light that entered from the input terminal enters the strain and temperature detector 14. Accordingly, the light pertaining to the stimulated Brillouin scattering phenomenon is output from one end of the detection optical fiber 15, and enters the strain and temperature detector 14 via the optical connector 9, the optical coupler 8, the optical circulator 7 and the 1×2 optical switch 29.

In the strain and temperature detector 14, the light pertaining to the stimulated Brillouin scattering phenomenon is directly detected and extracted as described above, converted into an electric signal by the light-receiving element, and filtered by the matched filter. The matched filter is, for example, as shown in FIG. 6B, a filter of a reverse phase modulation pattern ($P_nP_{n-1} \ldots P_3P_2P_1$) obtained by temporally reversing the phase modulation pattern ($P_1P_2P_3 \ldots P_{n-1}P_n$) that was subject to phase modulation based on the M sequence binary code by the LN phase modulator 111 of the light pulse generation unit 3.

For example, if the respective cells of the main light pulse are being modulated in the phase modulation pattern of "+−++−+ . . . +−" based on the M sequence binary code, the matched filter becomes a reverse pattern of "−+ . . . +−++−+" obtained by temporally reversing the foregoing phase modulation pattern. As a result of using this kind of matched filter, it is possible to accurately detect the light pertaining to the stimulated Brillouin scattering phenomenon caused by the main light pulse that was subject to spectral spread encoding. The strain and temperature detector 14 performs time domain analysis to the received light pertaining to the stimulated Brillouin scattering phenomenon based on the generation timing notified from the control processing unit 13, and measures the distribution of the optical intensity of the light pertaining to the stimulated Brillouin scattering phenomenon in the longitudinal direction of the detection optical fiber 15.

Here, the level of interaction between the pump light (sub light pulse and main light pulse) and the probe light (continuous light) pertaining to the stimulated Brillouin scattering phenomenon depends on the relative relationship of the polarization plane of the respective lights. However, with the distributed optical fiber sensor FS of this embodiment, since the polarization plane of the pump light changes randomly by the optical intensity/polarization adjustment unit 6 for each measurement, the foregoing dependency can be substantially eliminated by performing the measurement a plurality of times and adopting the average value thereof. Thus, it is possible to accurately obtain the distribution of the optical intensity of the light pertaining to the stimulated Brillouin scattering phenomenon.

The distribution of the optical intensity of the light pertaining to the stimulated Brillouin scattering phenomenon in the longitudinal direction of the detection optical fiber 15 can be measured in the respective frequencies with high precision and high spatial resolution by sweeping the frequency of the probe light (continuous light) output from the second light source 20 in a predetermined frequency range at a predetermined frequency interval based on the control of the control processing unit 13. Consequently, the Brillouin spectrum in the respective area portions in the longitudinal direction of the detection optical fiber 15 can be obtained with high precision and high spatial resolution.

Subsequently, the strain and temperature detector 14 obtains, with high precision and high spatial resolution, the Brillouin frequency shift amount in the respective portions of the detection optical fiber 15 in the longitudinal direction by respectively obtaining the difference between the frequency corresponding to the peak of the Brillouin spectrum in the respective area portions in the longitudinal direction of the detection optical fiber 15 in a state where no strain is generated, and the frequency corresponding to the peak of the Brillouin spectrum of the area portion corresponding to the respective area portions in a state where no strain is generated in the longitudinal direction of the detection optical fiber 15 in a state where strain is generated.

Returning once again to FIG. 4, the strain and temperature detector 14 subsequently estimates, in step S3, the Rayleigh frequency shift amount $\Delta vr$ from the Brillouin frequency shift amount $\Delta vb$ obtained based on the foregoing processing, and, in step S4, determines the frequency sweep range of the pulsed light for measuring the Rayleigh backscattered light from the estimated Rayleigh frequency shift amount $\Delta vr$.

Here, the Brillouin frequency shift amount $\Delta vb$ and the Rayleigh frequency shift amount $\Delta vr$ are represented with the following formulas when the strain variation is $\Delta \epsilon$, and the temperature variation is $\Delta T$. In the following formulas, $B11 \approx 0.05 \times 10^{-3}$ GHz/µε, $B12 \approx 1.07 \times 10^{-3}$ GHz/° C., $R11 \approx -0.15$ GHz/µε, $R12 \approx -1.25$ GHz/° C.

$$\Delta vb = B11 \times \Delta\epsilon + B12 \times \Delta T \quad (13)$$

$$\Delta vr = R11 \times \Delta\epsilon + R12 \times \Delta T \quad (14)$$

Upon comparing the foregoing formulas, it is evident that the sensitivity of the Rayleigh frequency shift amount $\Delta vr$ is extremely high in comparison to the Brillouin frequency shift amount $\Delta vb$. This is extremely effective for improving the measurement accuracy, but when the frequency sweep range for measuring the Rayleigh frequency shift amount $\Delta vr$ is determined as with the frequency sweep range for measuring the Brillouin frequency shift amount $\Delta vb$, the frequency sweep range for measuring the Rayleigh frequency shift amount $\Delta vr$ will become extremely wide, and much time will be required for the measurement.

Thus, in this embodiment, the Rayleigh frequency shift amount $\Delta vr$ is estimated from the previously measured Brillouin frequency shift amount $\Delta vb$. For example, if the Brillouin frequency shift amount $\Delta vb = 300$ MHz is obtained based on the measurement, foremost, when assuming that all changes are caused by the influence of temperature, $\Delta\epsilon = 0$, and $\Delta T = 300°$ C. is obtained from Formula (13). When this $\Delta T = 300°$ C. is substituted in Formula (14), $\Delta vr = -375$ GHz is obtained.

Next, when assuming that all changes are caused by the influence of strain, $\Delta T = 0$, and $\Delta\epsilon = 6000$µε is obtained from Formula (13). When this $\Delta\epsilon = 6000$µε is substituted in Formula (14), $\Delta vr = -900$ GHz is obtained. In the foregoing case, the range from $-375$ GHz to $-900$ GHz is determined as the frequency sweep range for measuring the Rayleigh frequency shift amount $\Delta vr$. Accordingly, if the vicinity of $-375$ GHz to the vicinity of $-900$ GHz is swept, the Rayleigh frequency shift amount $\Delta vr$ can be measured in a short time. Note that, as the frequency sweep range, the two frequencies obtained as described above may be used as is, or may be variously changed such as by arbitrarily adding a predetermined measurement margin, or narrowing the sweep range in a predetermined amount in order to shorten the measurement time. Moreover, in this example, a case was explained on the assumption that the lower limit of the temperature variation is $0°$ C., and the size of strain is limitless, but the range in the temperature variation or size of strain may be changed according to the applicable target of the device. Even in cases where an upper limit and a lower limit are assumed for the temperature variation, and an upper limit is assumed for the size of strain, the Rayleigh frequency sweep range is determined accordingly.

Subsequently, in step S5, the strain and temperature detector 14 uses the frequency sweep range determined as described above and measures the Rayleigh frequency shift amount Δvr. For example, the Rayleigh frequency shift amount Δvr can be obtained based on the following processing.

Foremost, the control processing unit 13 causes the first light source 1 to emit continuous light at a predetermined frequency by controlling the first ATC 10 and the first AFC 11. The continuous light output from the first light source 1 enters the light pulse generation unit 3 and the 1×2 optical switch 31 via the optical coupler 2, and the 1×2 optical switch 31 outputs the continuous light that was output from the first light source 1 to the optical coupler 30. Note that, during the measurement of the Rayleigh frequency shift amount, the optical switch 22 is turned OFF and light does not enter from the other end of the detection optical fiber 15.

Subsequently, the control processing unit 13 generates pulsed light for using the Rayleigh scattering phenomenon by controlling the light pulse generation unit 3. More specifically, the control processing unit 13 generates the pulsed light by causing the light pulse generation unit 3 to operate as follows.

FIG. 7 is a diagram showing an example of the pulsed light that is output from the light pulse generation unit 3 shown in FIG. 1, wherein FIG. 7A shows the wavelength of the pulsed light, and FIG. 7B shows the waveform of the pulsed light. The pulsed light shown in FIG. 7B is a square wave of a predetermined level, and, as shown in FIG. 7A, the cycle thereof is sequentially increased by a predetermined frequency for every predetermined number of pulses. Note that, in FIG. 7A, although the frequency is schematically shown as increasing linearly to simplify the illustration, strictly speaking, the frequency thereof is increased for every several pulses, and the frequency of the pulsed light increases in steps. Moreover, if the averaging described later is not performed; specifically, if the Rayleigh backscattered light is measured with one pulse, the frequency thereof may increase for each pulse.

Note that the pulsed light is not particularly limited to the foregoing example, and various modes of light may be used so as long as the Rayleigh scattering phenomenon can be utilized. Moreover, various methods such as modulation (encoding) based on the M sequence binary code may also be applied to the light using the Rayleigh scattering phenomenon as with the foregoing light to be used for the stimulated Brillouin scattering phenomenon.

In order to generate the pulsed light shown in FIG. 7, the continuous light output from the first light source 1 enters the LN intensity modulator 101 of the light pulse generation unit 3 via the optical coupler 2. In the light pulse generation unit 3, at the generation timing of the pulsed light, the operation timing pulse corresponding to the pulse width of the pulsed light is output from the timing pulse generator 104 to the multiplier 103, multiplied with the DC voltage input from the DC power source 102, and the DC voltage of the pulse width is applied to the signal electrode of the LN intensity modulator 101. Consequently, the LN intensity modulator 101 is turned ON during the duration corresponding to its pulse width according to the operation timing pulse, and the continuous light is output as the light pulse of the pulse width shown in FIG. 7B. The pulsed light thereafter enters the EDFA 121 via the LN phase modulator 111, amplified until the light pulse becomes a predetermined optical intensity, and output to the optical switch 4 via the LN intensity modulator 131.

Subsequently, the control processing unit 13 turns ON the optical switch 4 according to the generation timing of the pulsed light in the light pulse generation unit 3, and notifies the generation timing of the pulsed light to the strain and temperature detector 14.

When the optical switch 4 is turned ON, the pulsed light enters the optical coupler 5 and is branched into two pulsed lights. One of the branched pulsed lights enters the optical intensity/polarization adjustment unit 6, the optical intensity thereof is adjusted by the optical intensity/polarization adjustment unit 6, the polarization direction thereof is adjusted randomly, and enters one end of the detection optical fiber 15 via the optical circulator 7, the optical coupler 8 and the optical connector 9. Meanwhile, the other pulsed light branched by the optical coupler 5 enters the strain and temperature detector 14.

The strain and temperature detector 14 measures the spectrum of the pulsed light, and notifies the frequency and optical intensity of the pulsed light to the control processing unit 13. When the control processing unit 13 receives the foregoing notification, it controls the first ATC 10, the first AFC 11 and the optical intensity/polarization adjustment unit 6 as needed in order to obtain the optimal measurement result.

The pulsed light that entered one end of the detection optical fiber 15 is scattered within the detection optical fiber 15 and generates the Rayleigh scattering phenomenon, the light pertaining to the Rayleigh scattering phenomenon is output from one end of the detection optical fiber 15, and enters the optical coupler 30 via the optical connector 9, the optical coupler 8, the optical circulator 7 and the 1×2 optical switch 29. Consequently, the two lights mixed by the optical coupler 30 enter the strain and temperature detector 14.

As described above, the first light source 1 functions as the wavelength variable light source and changes the wavelength of the pulsed light with time, the light pulse generation unit 3 functions as the optical intensity modulator, the optical amplifier and the optical intensity modulator and creates a pulse of a predetermined pulse width, and the optical intensity/polarization adjustment unit 6 functions as the high-speed polarization scrambler and applies a random polarization plane to the respective pulsed lights. The optical coupler 30 mixes the continuous wave from the first light source 1 and the Rayleigh backscattered light from the detection optical fiber 15, and the light-receiving element of the strain and temperature detector 14 receives the foregoing lights in homodyne.

Here, since a random polarization plane is applied to the respective pulsed lights by the optical intensity/polarization adjustment unit 6 for each measurement, the strain and temperature detector 14 can obtain a smooth Rayleigh backscattered light by adding the Rayleigh backscattered light in the amount of the wavelength change and taking the average thereof, and the loss of the respective distances can be converted from the level of the Rayleigh backscattered light.

The distribution of the optical intensity of the light pertaining to the Rayleigh scattering phenomenon in the longitudinal direction of the detection optical fiber 15 can be measured in the respective frequencies with high precision and high spatial resolution by sweeping the frequency of the pulsed light in a predetermined frequency range based on the control of the control processing unit 13. Consequently, the Rayleigh spectrum in the respective area portions in the longitudinal direction of the detection optical fiber 15 can be obtained with high precision and high spatial resolution.

Subsequently, the strain and temperature detector 14 obtains, with high precision and high spatial resolution, the Rayleigh frequency shift amount in the respective portions of the detection optical fiber 15 in the longitudinal direction by respectively calculating the cross-correlation coefficient of the Rayleigh spectrum in the respective area portions in the longitudinal direction of the detection optical fiber 15 in a state where no strain is generated, and the Rayleigh spectrum of the area portion corresponding to the respective area portions in a state where no strain is generated in the longitudinal direction of the detection optical fiber 15 in a state where strain is generated.

FIG. 8 is a diagram showing an example of the Rayleigh frequency shift amount measured by the distributed optical fiber sensor FS shown in FIG. 1. FIG. 8A shows the Rayleigh spectrum in a case where there is strain and in a case where there is no strain, and FIG. 8B shows the cross-correlation coefficient in a case where there is strain and in a case where there is no strain. As shown in FIG. 8A, the Rayleigh spectrum in a case with strain is shown with a solid line in FIG. 8, and the Rayleigh spectrum in a case with no strain is shown with a broken line in FIG. 8, and, upon calculating the cross-correlation coefficient of the two, it becomes as shown in FIG. 8B, and the offset amount $\Delta vr$ of the peak of the cross-correlation coefficients of the two becomes the Rayleigh frequency shift amount.

If the Rayleigh spectrum (solid line) in the case with strain is moved in the amount of $\Delta vr$, it becomes as shown in FIG. 8C, and the Rayleigh spectrum (solid line) in the case with strain and the Rayleigh spectrum (broken line) in the case with no strain approximately coincide, and it is evident that the Rayleigh frequency shift amount was obtained with high precision and high spatial resolution.

Finally, in step S6, the strain and temperature detector 14 detects the strain and temperature in the respective portions of the detection optical fiber 15 in the longitudinal direction from the Brillouin frequency shift amount $\Delta vb$ and the Rayleigh frequency shift amount $\Delta vr$ obtained as described above.

Specifically, upon solving the strain variation $\Delta \epsilon$ and the temperature variation $\Delta T$ from foregoing Formula (13) and Formula (14), it will be as follows. In the following formulas, $C11 \approx -12755.102 \mu\epsilon/GHz$, $C12 \approx -10.918 \times \mu\epsilon/GHz$, $C21 \approx 1530.612° C./GHz$, $C22 \approx 0.510° C./GHz$.

$$\Delta \epsilon = C11 \times \Delta vb + C12 \times \Delta vr \quad (15)$$

$$\Delta T = C21 \times \Delta vb + C22 \times \Delta vr \quad (16)$$

The strain and temperature detector 14 substitutes the Brillouin frequency shift amount $\Delta vb$ and the Rayleigh frequency shift amount $\Delta vr$ of the respective area portions in the foregoing formulas, obtains the strain variation $\Delta \epsilon$ and the temperature variation $\Delta T$ in the respective area portions in the longitudinal direction of the detection optical fiber 15, and adds the obtained strain variation $\Delta \epsilon$ and the temperature variation $\Delta T$ to a predetermined reference strain and reference temperature in order to ultimately obtain the strain and temperature with high precision and high spatial resolution. The obtained distribution of the strain and temperature in the respective area portions in the longitudinal direction of the detection optical fiber 15 is present to an output unit not shown such as a CRT display device or an XY plotter or a printer.

According to the foregoing configuration, with the distributed optical fiber sensor FS of this embodiment, since the Brillouin frequency shift amount caused by the strain and temperature generated in the optical fiber 15 is measured by using the Brillouin scattering phenomenon, and the Rayleigh frequency shift amount caused by the strain and temperature generated in the detection optical fiber 15 is measured by using the Rayleigh scattering phenomenon, the strain and temperature generated in the detection optical fiber 15 can be simultaneously and independently calculated by using two frequency shift amounts, and the strain and temperature of the object to be measured appended with the detection optical fiber 15 can be measured simultaneously and independently with high spatial resolution. Consequently, it was possible to detect the strain and temperature with a spatial resolution of approximately 0.1 m and a precision of approximately $\pm 15 \mu\epsilon$ or less.

The second embodiment of the distributed optical fiber sensor according to the present invention is now explained with reference to the appended drawings. Note that the same reference numeral is used for the same configuration as the foregoing first embodiment and the detailed explanation thereof is omitted, and only the different configurations are explained in detail.

The distributed optical fiber sensor according to the second embodiment includes, as with the first embodiment, a first light source 1, optical couplers 2, 5, 8, 21, 23, 30, a light pulse generation unit 3, optical switches 4, 22, an optical intensity/polarization adjustment unit 6, optical circulators 7, 12, optical connectors 9, 26, 27, 28, a first ATC 10, a first AFC 11, a control processing unit 13, a strain and temperature detector 14, a detection optical fiber 15, a temperature detection unit 16, a reference optical fiber 17, a second ATC 18, a second AFC 19, a second light source 20, an optical intensity adjustment unit 24, and 1×2 optical switches 25, 29, 31 (refer to FIG. 1).

The strain and temperature detector 14 is configured by including a light-receiving element, an optical switch, an amplification circuit, an A/D converter, a signal processing circuit, a spectrum analyzer, a computer (CPU), a memory and the like.

When the light pertaining to the stimulated Brillouin scattering phenomenon from the detection optical fiber 15 appended to an object to be measured and which is in a state (reference state) where no heat or external force is applied from such object to be measured enters the light-receiving element for the stimulated Brillouin scattered light in the strain and temperature detector 14, the strain and temperature detector 14 obtains the Brillouin spectrum of the respective area portions (actual measured positions) of the detection optical fiber 15 in the longitudinal direction of the detection optical fiber 15 by connecting the light-receiving element for the stimulated Brillouin scattered light and the amplification circuit with an internal switch and detecting the light pertaining to the stimulated Brillouin scattering phenomenon that was received in a predetermined sampling interval. Subsequently, the strain and temperature detector 14 obtains the frequency (reference peak frequency) corresponding to the peak thereof from the obtained Brillouin spectrum of the respective area portions (actual measured positions), and stores the obtained reference peak frequency of the respective area portions (actual measured positions) in the memory.

Moreover, when the light pertaining to the Rayleigh backscattering phenomenon from the detection optical fiber 15 of a reference state enters the light-receiving element for the Rayleigh backscattered light in the strain and temperature detector 14, the strain and temperature detector 14 obtains the Rayleigh spectrum (reference Rayleigh spectrum) of the respective area portions (actual measured positions) of the detection optical fiber 15 in the longitudinal direction of the detection optical fiber 15 by connecting the light-receiving element for the Rayleigh backscattered light and the amplification circuit with an internal switch and detecting the light pertaining to the Rayleigh backscattering phenomenon that was received in a predetermined sampling interval. Subsequently, the strain and temperature detector 14 stores the obtained reference Rayleigh spectrum of the respective area portions (actual measured positions) in the memory.

Moreover, the strain and temperature detector 14 derives, with the CPU, the correction amount from the reference peak frequency of the respective actual measured positions stored in the memory, and the peak frequency of the Brillouin spectrum obtained from the Brillouin backscattered light from each of the actual measured positions in the detection optical fiber 15 in a state (measurement state) where the temperature and strain of the object to be measured are being measured.

The correction amount, the actual measured position and the intended measuring position are now explained. FIG. 9 is a diagram explaining the relation of the actual measured position and the intended measuring position. FIG. 9A shows a state where the object to be measured is not deformed due to heat or the like, and FIG. 9B shows a state where the object to be measured is deformed.

The correction amount is used upon correcting the shift between the actual measured position and the intended measuring position, and estimating the peak frequency of the Brillouin spectrum obtained from the Brillouin backscattered light from the intended measuring position based on the peak frequency of the Brillouin spectrum obtained from the Brillouin backscattered light from the actual measured position. Moreover, the correction amount is used upon estimating the Rayleigh spectrum obtained from the Rayleigh backscattered light from the intended measuring position based on the Rayleigh spectrum obtained from the Rayleigh backscattered light from the actual measured position.

The actual measured position is a position where the Brillouin spectrum and the Rayleigh spectrum are actually measured in the longitudinal direction of the detection optical fiber 15 by the foregoing distributed optical fiber sensor FS (refer to the black circles in FIG. 9A and FIG. 9B). In this embodiment, for example, the actual measured positions are positions that are aligned in 5 cm intervals from one end in the detection optical fiber 15. In the distributed optical fiber sensor FS, the Brillouin backscattered light is measured based on the time that the light propagates through the detection optical fiber 15. However, since the speed of light propagating through the detection optical fiber 15 will not change even if the detection optical fiber 15 expands or contracts, the actual measured position in the detection optical fiber 15 subject to the Brillouin backscattered light measured based on the foregoing time will not change (move) even if the detection optical fiber 15 expands or contracts (refer to the black circles in FIG. 9B). Specifically, the distance from one end of the detection optical fiber 15 appended to the object to be measured to the respective actual measured positions will be constant regardless of the expansion and contraction of the detection optical fiber 15.

Meanwhile, the intended measuring position is a position that is set on the detection optical fiber 15 and which overlaps with the actual measured position in the reference state (refer to the dotted line in FIG. 9A and FIG. 9B). Since the intended measuring position is a position on the detection optical fiber 15, it will shift from the actual measured position pursuant to the strain (expansion and contraction) of the detection optical fiber 15 based on the deformation of the object to be measured (refer to the broken line in FIG. 9B). Specifically, the distance from one end of the detection optical fiber 15 appended to the object to be measured to the respective intended measuring positions will change pursuant to the expansion and contraction of the detection optical fiber 15.

The strain and temperature detector 14 uses the foregoing correction amount and estimates the peak frequency of the Brillouin spectrum of the intended measuring position corresponding to the actual measured position from the peak frequency of the Brillouin spectrum of the respective actual measured positions in the detection optical fiber 15 in the measurement state. Moreover, the strain and temperature detector 14 uses the foregoing correction amount and estimates the Rayleigh spectrum of the intended measuring position corresponding to the actual measured position from the Rayleigh spectrum of the respective actual measured positions in the detection optical fiber 15 in the measurement state.

The strain and temperature detector 14 derives (measures) the Brillouin frequency shift amount $\Delta vb$ based on the reference peak frequency of the respective actual measured positions and the peak frequency of the intended measuring position corresponding to the respective actual measured positions. Moreover, the strain and temperature detector 14 derives (measures) the Rayleigh frequency shift amount $\Delta vr$ based on the reference Rayleigh spectrum of the respective actual measured positions and the Rayleigh spectrum of the intended measuring position corresponding to the respective actual measured positions.

The operation of measuring the stain and temperature of the distributed optical fiber sensor FS according to the second embodiment is now explained. FIG. 10 is a flowchart explaining the operation of measuring the strain and temperature performed by the distributed optical fiber sensor FS according to the second embodiment.

Foremost, prior to starting the measurement (sensing) of the strain and temperature of the object to be measured, in step S11, the strain and temperature detector 14 determines whether the peak frequency (reference peak frequency) of the Brillouin spectrum and the Rayleigh spectrum (reference Rayleigh spectrum) of the actual measured positions when the detection optical fiber 15 is in a reference state (for example, if the detection optical fiber 15 is appended to a plant or the like, a state where the plant is not operating) are stored in the memory.

If the above is not stored in the memory, foremost, in step S12, the strain and temperature detector 14 estimates the Brillouin frequency shift amount $\Delta vb$ as with step S1 of the first embodiment, determines the frequency sweep range for measuring the Brillouin frequency shift amount $\Delta vb$, and commands the control processing 13 for emitting the respective continuous lights from the first and second light sources 1, 20 in the determined sweep range. Note that, if the reference peak frequency and the reference Rayleigh spectrum of the respective actual measured positions are stored in the memory, the routine proceeds to step S15.

In step S13, the strain and temperature detector 14 measures the reference peak frequency of the Brillouin spectrum. For example, as with the process of measuring the distribution of the optical intensity of the light (Brillouin backscattered light) pertaining to the stimulated Brillouin scattering phenomenon in the longitudinal direction of the detection optical fiber 15 performed in step S2 of the first embodiment, the strain and temperature detector 14 measures the distribution of the optical intensity pertaining to the stimulated Brillouin scattering phenomenon, obtains the Brillouin spectrum of the respective area portions in the longitudinal direction of the detection optical fiber 15 from the measurement result thereof, and derives the reference peak frequency from the respective Brillouin spectrums. In this embodiment, the reference peak frequencies of the Brillouin spectrum of the actual measured positions set in 5 cm intervals in the longitudinal direction of the detection optical fiber 15 are respectively measured.

The reference peak frequencies of the Brillouin spectrum in the respective actual measured positions that were measured as described above (in this embodiment, the actual measured positions aligned in 5 cm intervals) are respectively stored in the memory of the strain and temperature detector 14.

Subsequently, in step S14, the strain and temperature detector 14 measures the reference Rayleigh spectrum. For example, the strain and temperature detector 14 measures the Rayleigh spectrum as with the process of measuring the distribution of the optical intensity of the light pertaining to the Rayleigh scattering phenomenon in the longitudinal direction of the detection optical fiber 15 performed in step S5 of the first embodiment. In this embodiment, the reference Rayleigh spectrums of the actual measured positions set in 5 cm intervals in the longitudinal direction of the detection optical fiber 15 are respectively measured. Note that, preferably, the frequency sweep range is set to be as wide as possible in the measurement of the Rayleigh spectrum within a range that is allowed by the capacity of the memory for storing the obtained data (Rayleigh spectrum and the like).

The reference Rayleigh spectrums in the respective actual measured positions that were measured as described above are respectively stored in the memory of the strain and temperature detector 14.

Subsequently, the strain and temperature of the object to be measured are measured in a state where the reference peak frequencies and the reference Rayleigh spectrums in the respective actual measured positions of the detection optical fiber 15 obtained from the detection optical fiber 15 in the reference state are respectively stored in the memory. Here, the detection optical fiber 15 is in a state (measurement state) where the strain of the object to be measured or the external force or heat based on the temperature change could be applied to the detection optical fiber 15.

The strain and temperature detector 14 is switched to the Brillouin measurement mode. Specifically, in step S15, the strain and temperature detector 14 estimates the Brillouin frequency shift amount $\Delta vb$ as in step S11, determines the frequency sweep range for measuring the Brillouin frequency shift amount $\Delta vb$, and commands the control processing unit 13 for causing the first and second light sources 1, 20 to emit the respective continuous lights in the determined sweep range.

Subsequently, in step S16, the strain and temperature detector 14 measures the peak frequency of the Brillouin spectrum in the respective actual measured positions of the detection optical fiber 15 as in step S13.

Figure 11B:
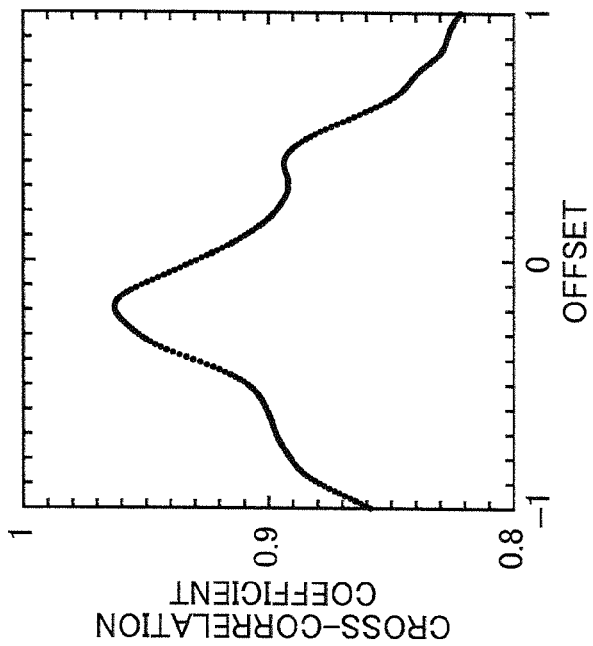
FIGS. 11A and 11B are diagrams explaining the method of deriving the correction amount.
Figure 11A:
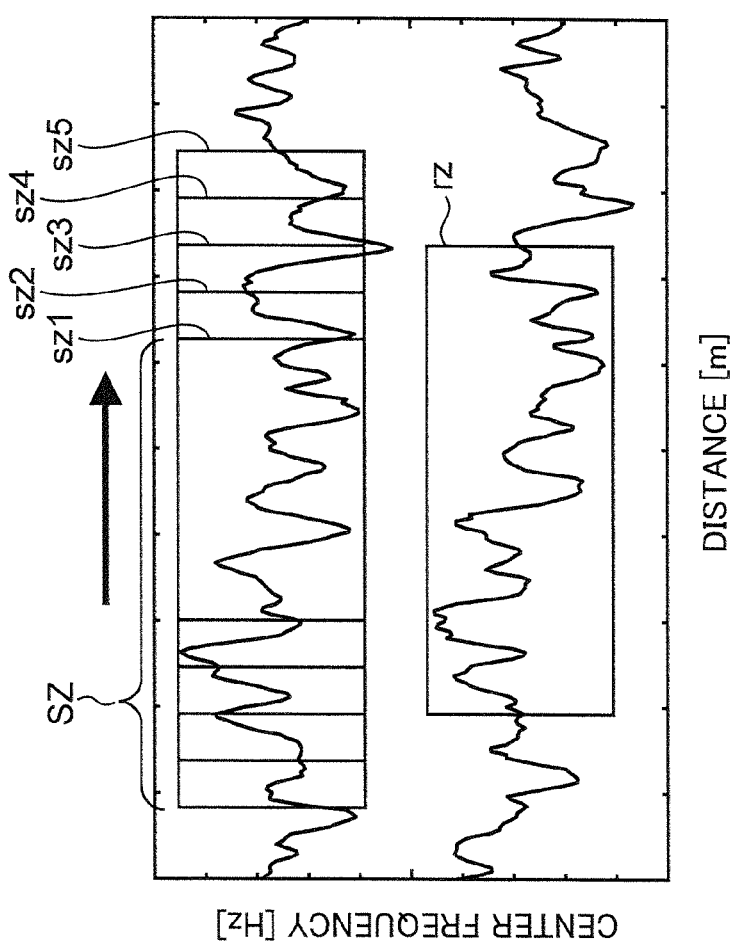

Subsequently, in step S17, the strain and temperature detector 14 elicits the reference peak frequencies stored in the memory, and derives the correction amount to be used for correcting the peak frequency measured from the detection optical fiber 15 in the measurement state based on the foregoing reference peak frequencies and the peak frequencies obtained from the detection optical fiber 15 in the measurement state. The correction amount can be derived, for example, based on the following processing. FIG. 11A and FIG. 11B are diagrams showing an example of the method of deriving the correction amount.

Foremost, the strain and temperature detector 14 divides the detection optical fiber 15 in the reference state into a plurality of areas in the longitudinal direction, and sets one of such areas as the reference area rz, and sets a correction area sz of a length corresponding to the reference area rz at a part of the longitudinal direction of the detection optical fiber 15 in the measurement state. The strain and temperature detector 14 calculates the cross-correlation coefficient of the waveform (refer to the area inside rz in FIG. 11A) in which the values of the reference peak frequencies of the respective actual measured positions included in the reference area rz are aligned in the longitudinal direction, and the waveform (refer to the area inside sz in FIG. 11(A)) in which the values of the peak frequencies of the respective actual measured positions included in the correction area sz are aligned in the longitudinal direction. The strain and temperature detector 14 repeatedly calculates the cross-correlation coefficient while moving the correction area sz at predetermined intervals (sz1, sz2, sz3, . . . in FIG. 11A) along the longitudinal direction, and plots the results thereof (refer to FIG. 11B). The length of movement (offset amount) in which the cross-correlation coefficient becomes maximum is the correction amount.

Figure 12:
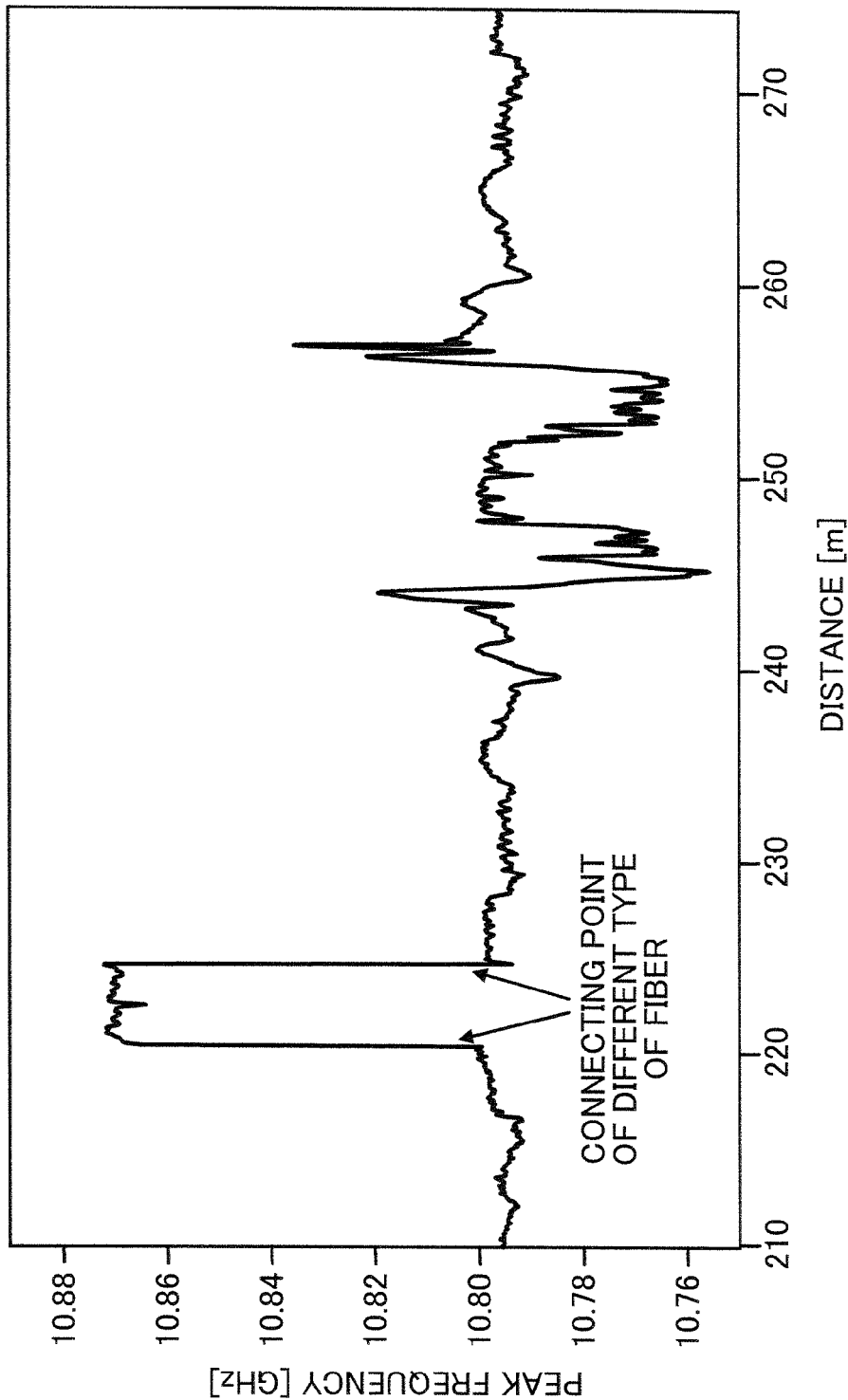
FIG. 12 is a diagram showing the Brillouin spectrum peak frequency at the respective positions in the longitudinal direction of the detection optical fiber in which a different type of fiber is connected at the midpoint thereof.

This utilizes the phenomenon where, as shown in FIG. 12, a unique waveform for each detection optical fiber is obtained due to the residual strain (initial residual strain) in the detection optical fiber 15 as a result of aligning, in order in the longitudinal direction, the peak frequencies of the Brillouin spectrum at the respective actual measured positions in the longitudinal direction of the detection optical fiber 15, and the characteristic of these waveforms is not lost even if the detection optical fiber 15 expands or contracts. Here, FIG. 12 is a diagram showing the Brillouin spectrum peak frequency at the area portions (actual measured positions) in the longitudinal direction of the detection optical fiber in which a different type of fiber is connected at the midpoint thereof.

Note that the method of deriving the correction amount is not limited to the method of deriving the correction amount by using the reference area rz and the correction area sz in which the range in the longitudinal direction is equal as described above. For example, the range in the longitudinal direction of the correction area may be set to be larger or smaller than the reference area rz based on the expansion and contraction of the detection optical fiber 15. It is thereby possible to measure the Brillouin frequency shift amount and the Rayleigh frequency shift amount with even higher precision.

The strain and temperature detector 14 repeats the foregoing derivation of the correction amount with each of the plurality of areas in which the detection optical fiber 15 in the reference state was divided in the longitudinal direction as the reference area rz. The correction amount relative to all actual measured positions of the detection optical fiber 15 is thereby derived.

Subsequently, in step S18, the strain and temperature detector 14 estimates the respective peak frequencies at the intended measuring position corresponding to the respective actual measured values from the peak frequencies obtained with the respective actual measured values. For example, the peak frequencies of the intended measuring position can be obtained based on the following processing.

The strain and temperature detector 14 derives the respective intended measuring positions corresponding to the respective actual measured positions from such actual measured positions based on the correction amount that was derived for each reference area as described above. Meanwhile, the strain and temperature detector 14 interpolates the measured values (peak frequencies) of the mutually adjacent actual measured positions so that the values of the peak frequencies that were obtained discretely in the longitudinal direction (in this embodiment, in 5 cm intervals in the longitudinal direction) become successive in the longitudinal direction. In this embodiment, the foregoing interpolation is performed with the B spline interpolation method, but the method is not limited thereto, and other interpolation methods and a method of least squares or the like may also be used.

The strain and temperature detector 14 estimates the respective peak frequencies obtained from the Brillouin back-scattered light from the intended measuring positions based on such intended measuring positions and the interpolated values obtained as described above.

Subsequently, in step S19, the strain and temperature detector 14 derives (measures) the respective Brillouin frequency shift amounts Δvb from the difference between the reference peak frequencies at the respective measured positions of the detection optical fiber 15 in the reference state stored in the memory, and the peak frequencies at the intended measuring position corresponding to each of the foregoing actual measured positions that were estimated based on the foregoing processing.

When the Brillouin frequency shift amount Δvb is derived as described above, the strain and temperature detector 14 is changed from the Brillouin measurement mode to the Rayleigh measurement mode.

Foremost, as in steps S3 and S4 of the first embodiment, the strain and temperature detector 14 estimates, in step S20, the Rayleigh frequency shift amount Δvr from the Brillouin frequency shift amount Δvb obtained based on the foregoing processing, and, in step S21, determines the frequency sweep range of the pulsed light for measuring the Rayleigh backscattered light from the estimated Rayleigh frequency shift amount Δvr.

Subsequently, in step S22, the strain and temperature detector 14 measures the Rayleigh spectrum in the respective actual measured positions of the detection optical fiber 15 as in step S5 of the first embodiment. Subsequently, in step S23, the strain and temperature detector 14 estimates the respective Rayleigh spectrums at the intended measuring position corresponding to the respective actual measured positions from the Rayleigh spectrum obtained at the respective actual measured positions. For example, the Rayleigh spectrum at the intended measuring position can be obtained based on the following processing.

The strain and temperature detector 14 derives the respective intended measuring positions corresponding to the respective measured positions from such actual measured positions based on the correction amount that was derived for each reference area in step S17. Meanwhile, the strain and temperature detector 14 interpolates the measured values (Rayleigh spectrums) of the mutually adjacent actual measured positions so that the Rayleigh spectrums that were obtained discretely in the longitudinal direction (in this embodiment, in 5 cm intervals in the longitudinal direction) become successive in the longitudinal direction. The strain and temperature detector 14 estimates the respective Rayleigh spectrums obtained from the Rayleigh backscattered light from the respective intended measuring positions based on the respective measuring positions and the interpolated values obtained as described above.

Subsequently, in step S24, the strain and temperature detector 14 derives (measures) the respective Rayleigh frequency shift amount Δvr, as in step S5 of the first embodiment, based on the reference Rayleigh spectrum at the respective actual measured positions stored in the memory, and the Rayleigh spectrums at the intended measuring position corresponding to each of the actual measured positions that were estimated based on the foregoing processing.

Here, if the Rayleigh frequency shift amount Δvr is sufficiently small in comparison to the frequency range (bandwidth) of the measured Rayleigh spectrum, as in step S5 of the first embodiment, the Rayleigh frequency shift amount Δvr can be easily derived based on the cross-correlation coefficient of the reference Rayleigh spectrum at the respective actual measured positions stored in the memory and the Rayleigh spectrum (hereinafter also referred to as the "corresponding Rayleigh spectrum") measured at the intended measuring position corresponding to the respective actual measured positions. Nevertheless, if the Rayleigh frequency shift amount Δvr is not sufficiently small as the foregoing shift amount (that is, if it is sufficiently great) in comparison to the frequency range of the reference Rayleigh spectrum or the frequency range of the corresponding Rayleigh spectrum, the reliability of the derived cross-correlation coefficient will decrease (that is, the error will increase) since the corresponding range (overlapping portion) of the reference Rayleigh spectrum and the corresponding Rayleigh spectrum upon deriving the cross-correlation coefficient will decrease, and, therefore, it becomes difficult to derive the Rayleigh frequency shift amount Δvr.

Specifically, if the Rayleigh frequency shift amount Δvr is sufficiently small in comparison to the frequency range of the reference Rayleigh spectrum and the frequency range of the corresponding Rayleigh spectrum, in the graph (refer to FIG. 8A) with the horizontal axis as the frequency and the vertical axis as the spectrum level, the Rayleigh frequency shift amount Δvr can be easily derived by deriving the cross-correlation coefficient of the waveform of the reference Rayleigh spectrum and the waveform of the corresponding Rayleigh spectrum at the respective relative positions by mutually and relatively moving the waveform of the reference Rayleigh spectrum and the waveform of the corresponding Rayleigh spectrum in the frequency axis direction (left and right direction in FIG. 8) (refer to FIG. 8B). Note that, in this embodiment, the strain and temperature detector 14 derives the cross-correlation coefficient at the respective positions (respective shift amounts) by fixing the waveform of the reference Rayleigh spectrum while laterally moving (shifting) the waveform of the corresponding Rayleigh spectrum.

Figure 13:
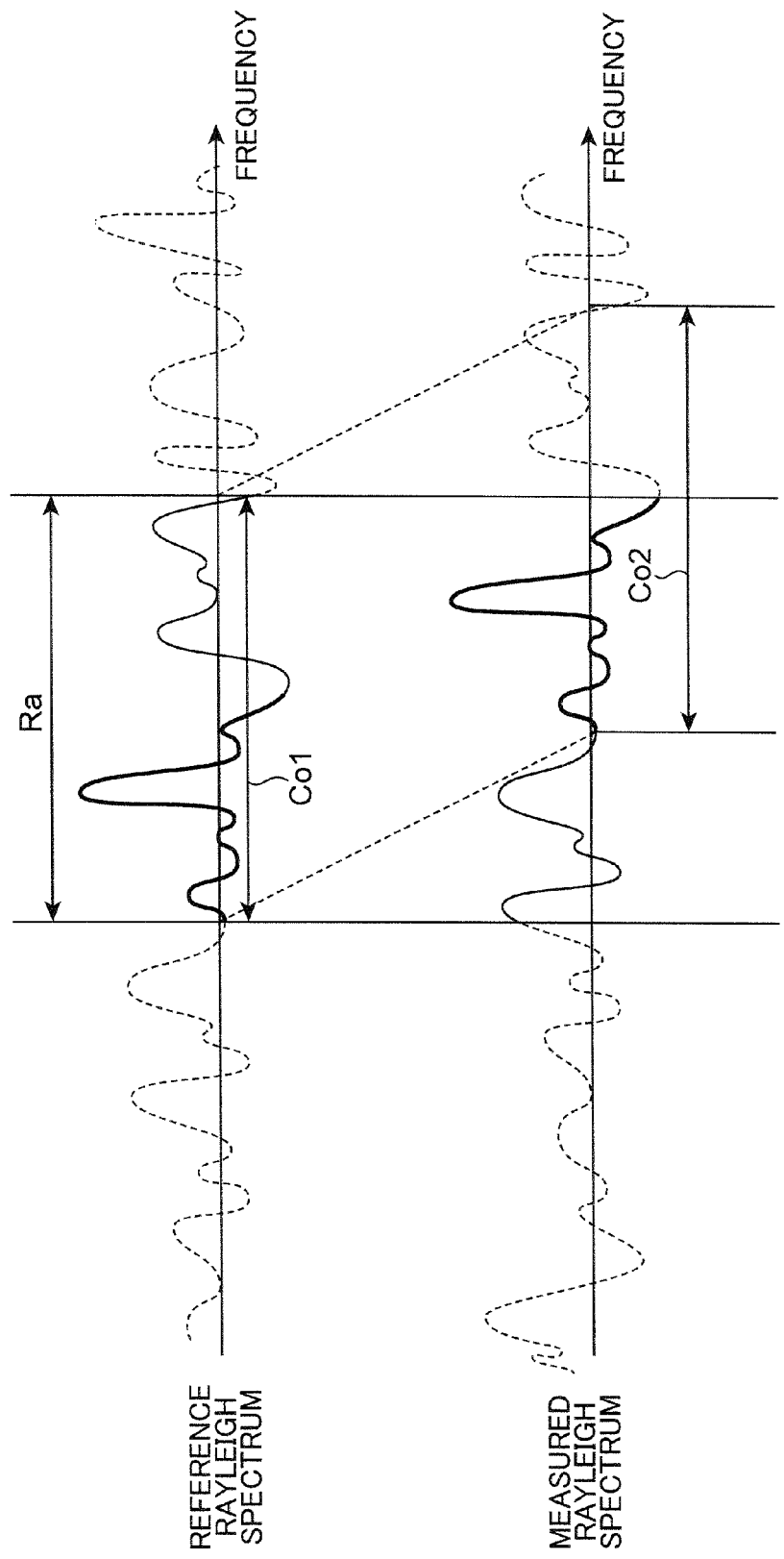
FIG. 13 is a schematic diagram explaining the relation of the reference Rayleigh spectrum and the measured Rayleigh spectrum.

Meanwhile, if the Rayleigh frequency shift amount Δvr as shown in FIG. 13 is relatively great in comparison to the frequency range of the reference Rayleigh spectrum or the frequency range of the corresponding Rayleigh spectrum (range of Ra in FIG. 13) stored in the memory of the strain and temperature detector 14, since the overlapping portion (range in the frequency axis direction shown with a bold line in FIG. 13) is small even if the waveforms of both spectrums within the range Ra of the measured frequencies are relatively moved, the reliability of the cross-correlation coefficient derived at the respective relative positions will decrease.

Specifically, when the shift amount relatively increases relative to the frequency range of both spectrums, in the portion Co2 of the waveform of the corresponding Rayleigh spectrum corresponding to the portion (portion of the upper waveform shown with a solid in FIG. 13) Co1 of the waveform of the reference Rayleigh spectrum in the range Ra of the measured frequency, only a part thereof (overlapping portion: portion of the lower waveform shown with a bold line in FIG. 13) will fall within the frequency range Ra. In addition, since the extension or strain in the detection optical fiber 15 is not uniform (that is, it is uneven) in the respective portions in the longitudinal direction and the direction that is orthogonal thereto, the mutually corresponding portions Co1 and Co2 of the waveform of the reference Rayleigh spectrum and the waveform of the corresponding Rayleigh spectrum will also not be a perfect match. Thus, even if the cross-correlation coefficient at the respective positions is derived while relatively moving the waveform of the reference Rayleigh spectrum within the range Ra of the measured frequency and the waveform of the corresponding Rayleigh spectrum in the frequency axis direction, it does not necessary mean that the cross-correlation coefficient when the overlapping portions are overlapped will become maximum (refer to FIG. 8B), and the derivation of the Rayleigh frequency shift amount Δvr thereby becomes difficult.

Here, it is also possible to eliminate the foregoing difficulty by sufficiently increasing the frequency range of the reference Rayleigh spectrum and the frequency range of the corresponding Rayleigh spectrum relative to the Rayleigh frequency shift amount Δvr. Nevertheless, if the range of frequency to be measured is increased, in addition to the time required for measurement increasing, the time required for deriving the cross-correlation coefficient at the respective positions while relatively moving the waveform of the reference Rayleigh spectrum within the range Ra of the measured frequency and the waveform of the corresponding Rayleigh spectrum in the frequency axis direction will also increase, and there is a problem in that too much time is required.

Thus, if the Rayleigh frequency shift amount Δvr is relatively large in comparison to the frequency range of the reference Rayleigh spectrum or the frequency range of the corresponding Rayleigh spectrum, the strain and temperature detector 14 uses a predetermined threshold for determining the Rayleigh frequency shift amount, and attempts to derive the Rayleigh frequency shift amount Δvr by comparing the foregoing predetermined threshold and the cross-correlation coefficient at the respective positions in the frequency axis direction of the waveform of the reference Rayleigh spectrum and the waveform of the corresponding Rayleigh spectrum. With this strain and temperature detector 14, since the Rayleigh frequency shift amount Δvr is derived based on the comparison of the predetermined threshold and the cross-correlation coefficient at the respective relative positions; that is, based on the size of the numerical value, the Rayleigh frequency shift amount Δvr can be derived easily.

Figure 14:
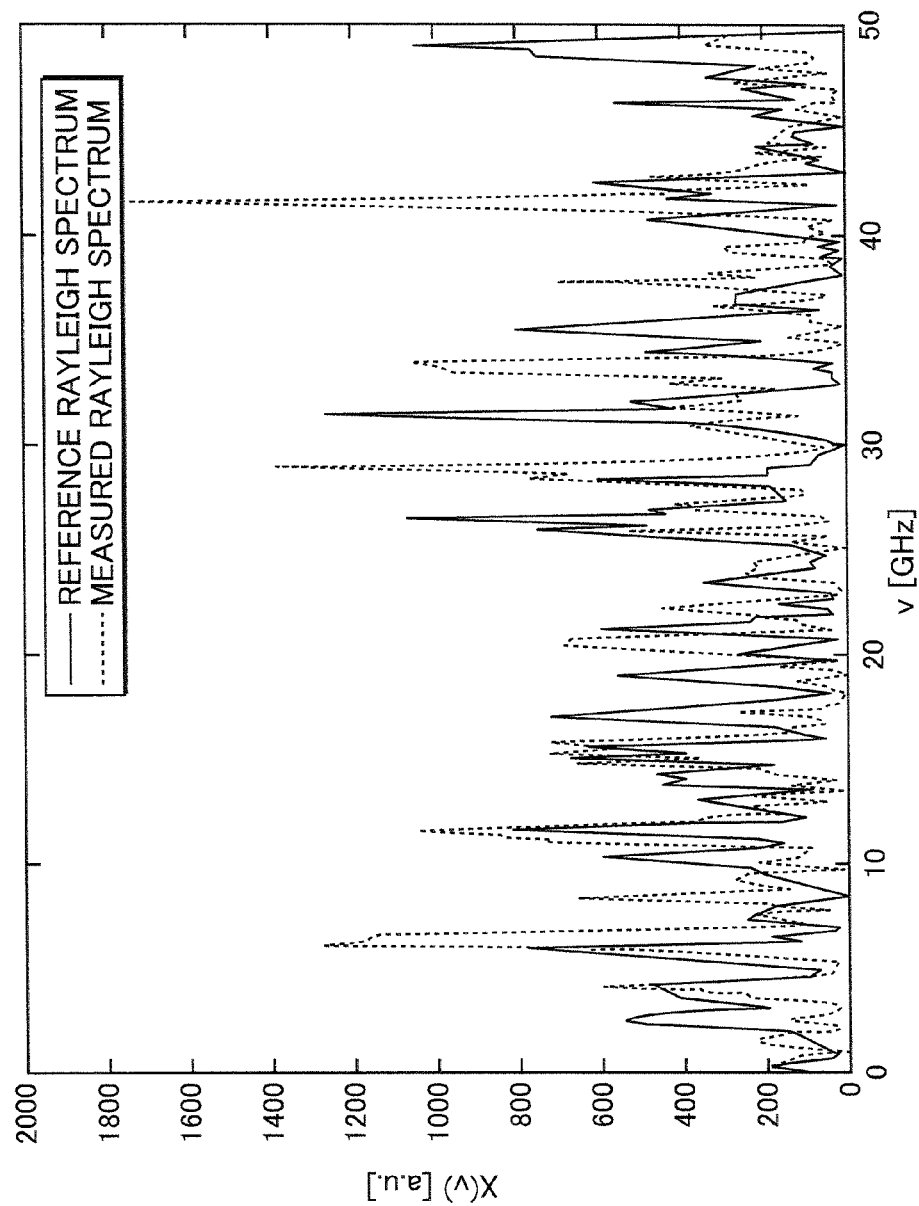
FIG. 14 is a diagram showing the reference Rayleigh spectrum and the measured Rayleigh spectrum.
Figure 15:
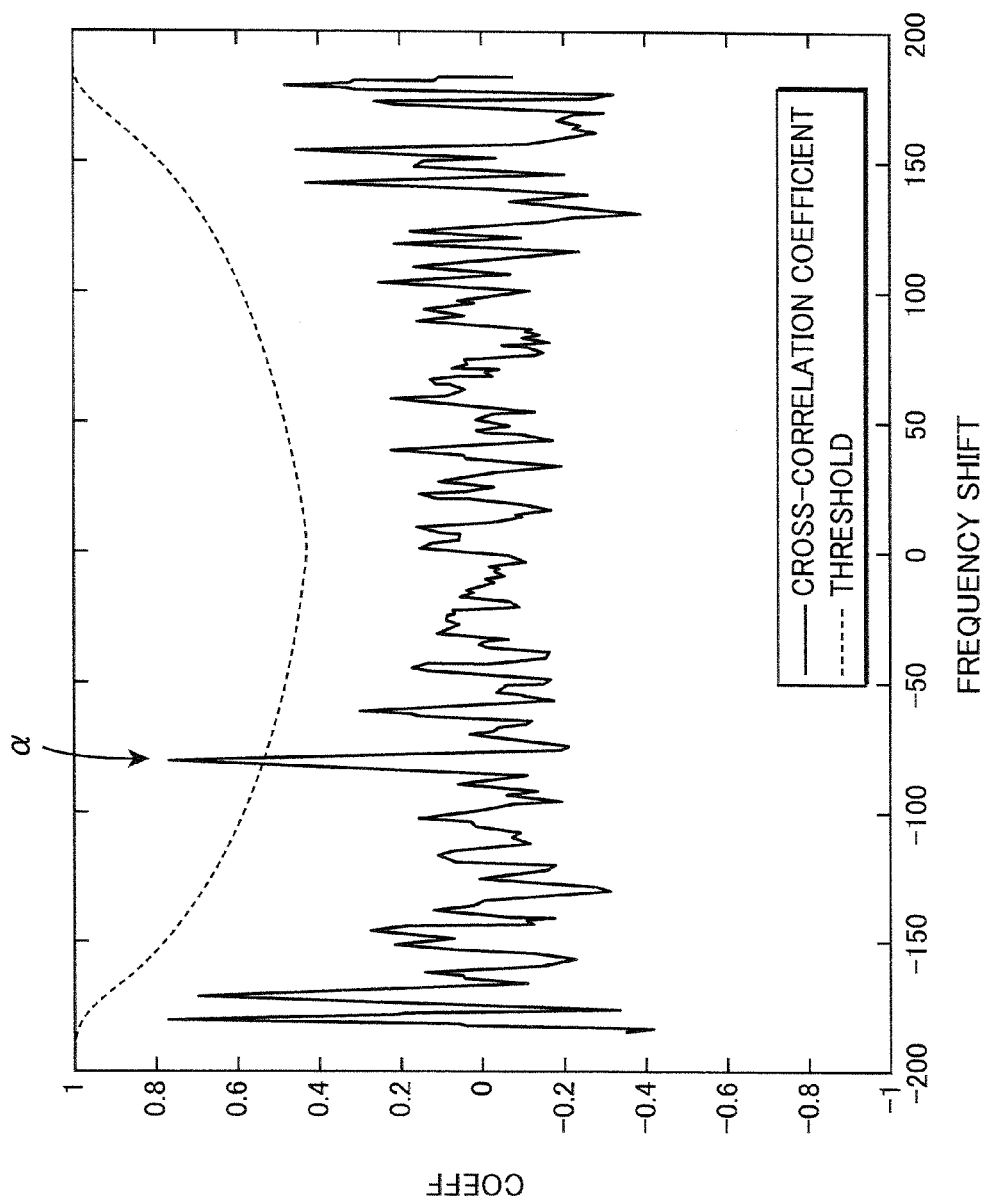
FIG. 15 is a diagram showing the relation of the threshold and the cross-correlation coefficient.

In the longitudinal direction of the detection optical fiber 15, the waveform of the reference Rayleigh spectrum actually measured in a predetermined time interval at a specific actual measured position, and the waveform of the corresponding Rayleigh spectrum at the intended measuring position corresponding to the foregoing specific actual measured position will be, for example, the shape shown in FIG. 14. When the waveform of the reference Rayleigh spectrum and the waveform of the corresponding Rayleigh spectrum in FIG. 14 are relatively moved in the frequency axis direction, and the cross-correlation coefficient at the respective relative positions is derived and plotted, the graph shown in FIG. 15 is obtained. As shown in FIG. 15, in the actual measurement, there are cases where multiple peaks will appear since the extension, strain and the like at the respective portions of the detection optical fiber 15 become uneven.

In the foregoing case, the strain and temperature detector 14 uses the predetermined threshold th as shown in FIG. 15 which is stored in advance in the memory and attempts to derive the Rayleigh frequency shift amount Δvr by comparing the threshold th and the cross-correlation coefficient.

This threshold th becomes the smallest amount when the shift amount of the waveform of the corresponding Rayleigh spectrum in the frequency axis direction relative to the waveform of the reference Rayleigh spectrum upon obtaining the cross-correlation coefficient is 0, and becomes a greater value as the shift amount increases. This is because, since the overlapping portion of the corresponding portion of the waveform of the reference Rayleigh spectrum and the waveform of the corresponding Rayleigh spectrum in the predetermined frequency range becomes larger as the shift amount becomes smaller, the reliability of the derived cross-correlation coefficient is high even if the degree of coincidence of both waveforms (size of the cross-correlation coefficient) is low in comparison to cases when the shift amount is large. Meanwhile, if the shift amount is large, since the overlapping portion in the corresponding portion of the waveforms of both spectrums will decrease, it is not possible to obtain the same level of reliability as when the shift amount is small if the degree of coincidence (cross-correlation coefficient) of both waveforms is not high in comparison to cases when the shift amount is small.

Specifically, the threshold th is based on a probability (false alarm probability) concerning the reliability of the cross-correlation coefficient of the reference Rayleigh spectrum and the corresponding Rayleigh spectrum, and is defined so that the false alarm probability becomes constant for each shift amount of the corresponding Rayleigh spectrum relative to the reference Rayleigh spectrum (or the shift amount of the reference Rayleigh spectrum relative to the corresponding Rayleigh spectrum). Here, the false alarm probability is the probability where the value of the cross-correlation coefficient will exceed the threshold when the shift amount is not a proper value (that is, when the corresponding portions of the waveform of the reference Rayleigh spectrum and the waveform of the corresponding Rayleigh spectrum are not overlapping). The false alarm probability is logically obtained for each threshold in the respective shift amounts by considering a case where the reference Rayleigh spectrum and the corresponding Rayleigh spectrum are uncorrelated. Accordingly, the threshold for each shift amount can be obtained by designating the false alarm probability (refer to the threshold th in FIG. 15).

As a result of using this kind of threshold th, even if multiple peaks appear in the graph of the cross-correlation coefficient at the respective relative positions (respective shift amounts), by comparing the values of the threshold th and the cross-correlation coefficient, if there is a cross-correlation coefficient that exceeds the threshold th (arrow α in FIG. 15), the shift amount of the corresponding Rayleigh spectrum in the frequency axis direction relatively to the waveform of the reference Rayleigh spectrum when the foregoing cross-correlation coefficient was obtained can be easily derived as the Rayleigh frequency shift amount Δvr.

Moreover, in order to derive the Rayleigh frequency shift amount Δvr even more reliably, in substitute for the cross-correlation coefficient of the reference Rayleigh spectrum and the corresponding Rayleigh spectrum, the cross-correlation coefficient of the square root of the reference Rayleigh spectrum and the square root of the corresponding Rayleigh spectrum may also be used. Specifically, the strain and temperature detector 14 may also be configured so that it obtains the cross-correlation coefficient of the square root of the reference Rayleigh spectrum and the square root of the corresponding Rayleigh spectrum for each shift amount, and derives the Rayleigh frequency shift amount Δvr from the peak position of the cross-correlation coefficient which exceeds the threshold th in which the false alarm probably becomes constant in the respective shift amounts. In the foregoing case, the false alarm probability will decrease since the level of the cross-correlation coefficient in cases where the square root of the reference Rayleigh spectrum and the square root of the corresponding Rayleigh spectrum are mutually uncorrelated will decrease, and the threshold th in which the false alarm probably becomes constant in the respective shift amounts will also decrease. Consequently, the certainty of detecting the correct Rayleigh frequency shift amount Δvr can be improved. The reason why the false alarm probability decreases when using the square root of the spectrum rather than the spectrum itself is because, whereas the probability distribution of the spectrum value becomes an index distribution, the probability distribution of the square root value becomes a Rayleigh distribution, and the index distribution becomes longer at the tail of the distribution.

Accordingly, if the Rayleigh frequency shift amount $\Delta vr$ is relatively large in comparison to the frequency range of the reference Rayleigh spectrum or the frequency range of the corresponding Rayleigh spectrum, the strain and temperature detector 14 uses the foregoing threshold th and detects the Rayleigh frequency shift amount $\Delta vr$.

Nevertheless, there are cases where the strain and temperature detector 14 is unable to derive the Rayleigh frequency shift amount $\Delta vr$ even upon using the foregoing threshold th (cases where a plurality of cross-correlation coefficients exceed the threshold th or when none of them exceed the threshold th). In the foregoing case, the strain and temperature detector 14 derives the Rayleigh frequency shift amount $\Delta vr$ by additionally performing the following processing.

When measuring (deriving) the Rayleigh frequency shift amount $\Delta vr$, the Brillouin frequency shift amount $\Delta vb$ has been previously measured (derived) in step S19. Here, since the measurement was performed using the scattered light of the light obtained from the same detection optical fiber 15, there is a predetermined correspondence relation between the Brillouin frequency shift amount $\Delta vb$ and the Rayleigh frequency shift amount $\Delta vr$. Thus, if the strain and temperature detector 14 is unable to derive the Rayleigh frequency shift amount $\Delta vr$ even upon using the threshold th, it attempts to derive the Rayleigh frequency shift amount $\Delta vr$ by using the previously derived Brillouin frequency shift amount $\Delta vb$.

Specifically, the strain and temperature detector 14 uses following Formula (13) and Formula (14) which were used upon estimating the Rayleigh frequency shift amount $\Delta vr$ from the Brillouin frequency shift amount $\Delta vb$ in step S20 (step S3 in the first embodiment) and determines the scanning range Sa in FIG. 16A showing the relation of the relative position of the waveform of the reference Rayleigh spectrum and the waveform of the corresponding Rayleigh spectrum (in this embodiment, the shift amount of the waveform of the corresponding Rayleigh spectrum in the frequency axis direction relative to the waveform of the reference Rayleigh spectrum) and the cross-correlation coefficient, and obtains the Rayleigh frequency shift amount $\Delta vr$ in the scanning range Sa1 (refer to FIG. 16B) based on the foregoing scanning range Sa.

$$\Delta vb = B11 \times \Delta\epsilon + B12 \times \Delta T \quad (13)$$

$$\Delta vr = R11 \times \Delta\epsilon + R12 \times \Delta T \quad (14)$$

Specifically, the strain and temperature detector 14 assumes that all changes are based on the influence of temperature in Formula (13) and Formula (14). Consequently, the following is obtained.

$$\Delta vr = (R11/B11)\Delta vb \quad (17)$$

Subsequently, the strain and temperature detector 14 assumes that all change are based on the influence of strain. Consequently, the following is obtained.

$$\Delta vr = (R12/B12)\Delta vb \quad (18)$$

The strain and temperature detector 14 substitutes, in obtained Formula (17), the value of the Brillouin frequency shift amount $\Delta vb$ measured in step S19 and the specific values of B11, R11 (for example, in the first embodiment, $B11 \approx 0.05 \times 10^{-3}$ GHz/$\mu\epsilon$, $R11 \approx -0.15$ GHz/$\mu\epsilon$) and derives the lower limit value of the scanning range Sa (solid line on the left side in FIG. 16A), and substitutes, in obtained Formula (18), the value of the Brillouin frequency shift amount $\Delta vb$ and the specific values of B12, R12 (for example, in the first embodiment, $B12 \approx 1.07 \times 10^{-3}$ GHz/° C., $R12 \approx -1.25$ GHz/° C.) and drives the upper limit value of the scanning range Sa (solid line on the right side in FIG. 16A). After determining the upper limit value and the lower limit value of the scanning range Sa as described above, the strain and temperature detector 14 adds a predetermined measurement margin (dotted line in FIG. 16A) in consideration of errors. The strain and temperature detector 14 obtains the value of the relative position (shift amount) with the greatest cross-correlation coefficient in the range of the scanning range Sa1 including the predetermined measurement margin, and derives the value of this relative position as the Rayleigh frequency shift amount $\Delta vr$.

Note that the strain and temperature detector 14 is not limited to the method of using the threshold th, or the method of using the value of the previously obtained Brillouin frequency shift amount $\Delta vb$ and Formula (13) and Formula (14), and may be configured to derive the Rayleigh frequency shift amount $\Delta vr$ from data (reference Rayleigh spectrum and corresponding Rayleigh spectrum) containing much noise by using other methods or sequentially using both the foregoing method and another method.

When the Rayleigh frequency shift amounts $\Delta vr$ are respectively derived (measured) in step S24 as described above, finally, in step S25, the strain and temperature detector 14 detects the strain and temperature at the respective portions of the detection optical fiber 15 in the longitudinal direction from the Brillouin frequency shift amount $\Delta vb$ and the Rayleigh frequency shift amount $\Delta vr$ obtained based on the foregoing processing.

Based on the foregoing configuration, with the distributed optical fiber sensor FS of this embodiment, even if the detection optical fiber 15 is long or the temperature change or strain change is great and the shifting between the actual measured position and the intended measuring position is consequently great in the measurement state, by deriving the correction amount concerning the foregoing shifting from the Brillouin backscattered light and using the correction amount, the Brillouin frequency shift amount and the Rayleigh frequency shift amount can be detected accurately. Moreover, in particular, as a result of using this correction amount, the detection (Rayleigh measurement) of the Rayleigh frequency shift amount can be performed reliably. This is because, since the Rayleigh spectrum depends strongly on the width of the main pulsed light, the correlation of the reference state and the measurement state in the Rayleigh measurement cannot be obtained if the position is not corrected (correction of the actual measured position and the intended measuring position corresponding thereto) with an accuracy of the width (10 cm in this embodiment) level of the main pulsed light.

Figure 17C:
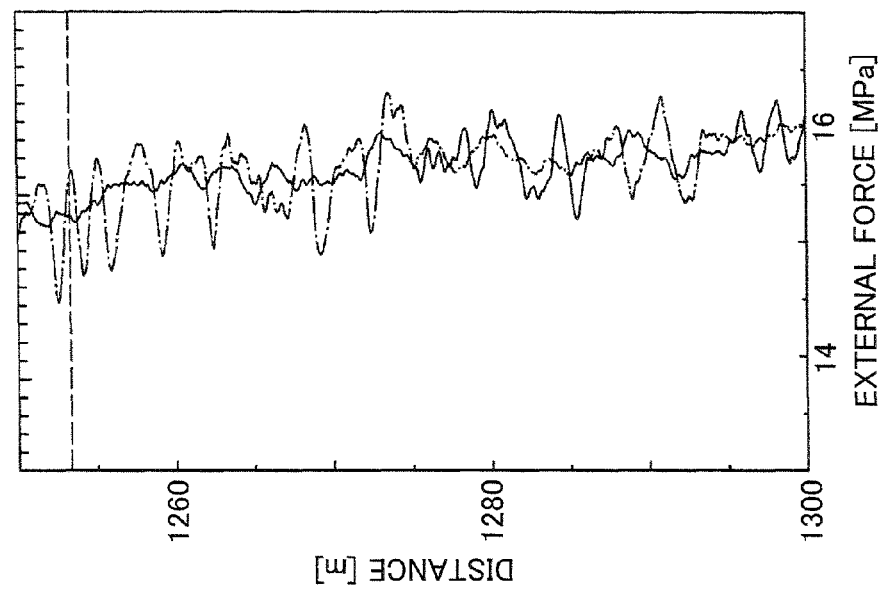
FIGS. 17A, 17B and 17C are diagrams explaining the effect of correction based on the correction amount.
Figure 17A:
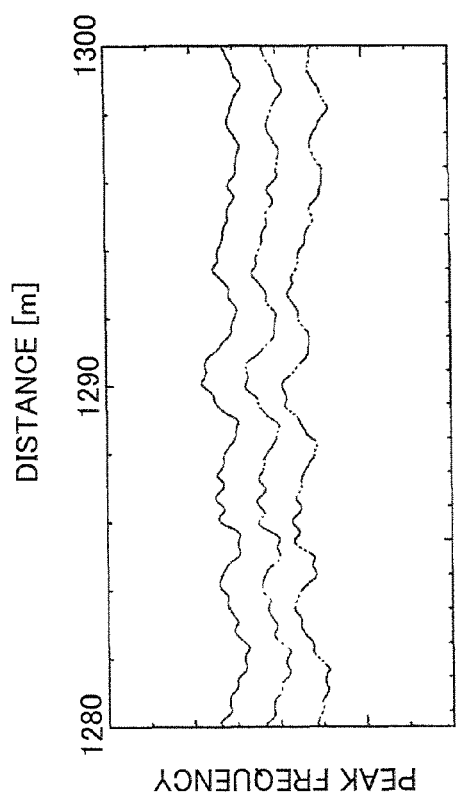
Figure 17B:
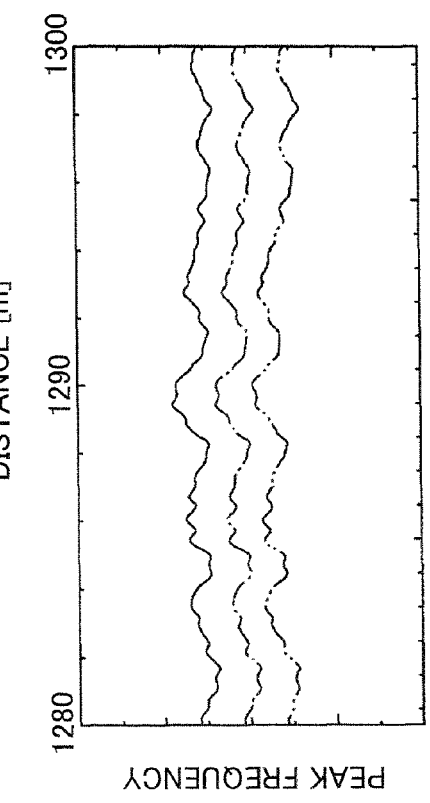

For example, if the detection optical fiber 15 is in three different states, the results shown in FIG. 17A were obtained upon measuring the respective peak frequencies of the Brillouin spectrum. Based on these results, if the Brillouin frequency shift amount $\Delta vb$ and the Rayleigh frequency shift amount $\Delta vr$ are measured and the external force applied from the object to be measured to the detection optical fiber 15 is obtained without performing any correction with the correction amount as with the foregoing configuration, the results shown with the dashed line of FIG. 17C were obtained. Meanwhile, the results shown in FIG. 17B were obtained by correcting the results obtained as shown in FIG. 17A by obtaining the correction amount for correcting the shifting between the actual measured position and the intended measuring position associated with the expansion and contraction of the detection optical fiber 15 as with the foregoing configuration. The results shown with the solid line of FIG. 17C were obtained by using the foregoing results to measure the Brillouin frequency shift amount Δvb and the Rayleigh frequency shift amount Δvr and obtaining the external force applied from the object to be measured to the detection optical fiber 15. As evident from FIG. 17C, as a result of correcting the shifting between the actual measured position and the intended measuring position associated with the expansion and contraction of the detection optical fiber 15, noise caused by the expansion and contraction decreased and results with low deflection were obtained.

Note that the distributed optical fiber sensor FS with the configuration shown in FIG. 1 can also configure the BOTDR with a part of its constituent elements.

Figure 18:
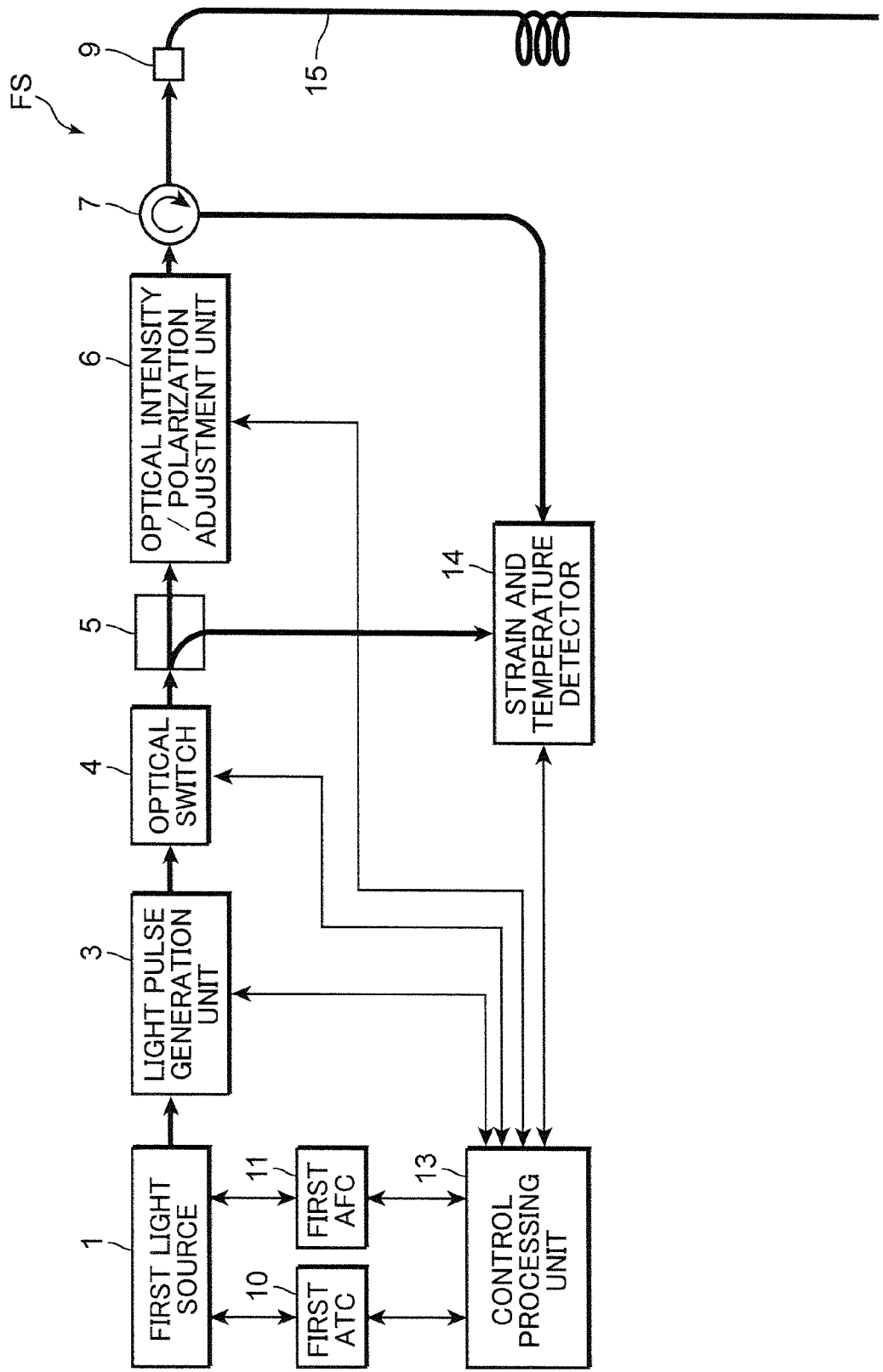
FIG. 18 is a block diagram showing the configuration of the distributed optical fiber sensor when the distributed optical fiber sensor shown in FIG. 1 is configured as a BOTDR.

FIG. 18 is a block diagram showing the configuration of the distributed optical fiber sensor when the distributed optical fiber sensor shown in FIG. 1 is configured as a BOTDR. Note that, in FIG. 18, only the blocks that are required for configuring the BOTDR are shown, and the illustration of certain blocks has been omitted.

In FIG. 18, the distributed optical fiber sensor FS of the BOTDR is configured by including a first light source 1, a light pulse generation unit 3, an optical switch 4, an optical coupler 5, an optical intensity/polarization adjustment unit 6, an optical circulator 7, an optical connector 9, a first ATC 10, a first AFC 11, a control processing unit 13, a strain and temperature detector 14, and a detection optical fiber 15. Note that, in FIG. 18, since the optical coupler 2 interposed between the first light source 1 and the light pulse generation unit 3 and the optical coupler 8 interposed between the optical circulator 7 and the optical connector 9 do not substantially function when the distributed optical fiber sensor FS shown in FIG. 1 is configured as a BOTDR, the illustration thereof is omitted, and the 1×2 optical switch 29 not shown connects the optical circulator 7 and the strain and temperature detector 14.

In the case of a BOTDR, the strain and temperature detector 14 controls the respective components of the distributed optical fiber sensor FS by inputting and outputting signals to and from the control processing unit 13, obtains the respective Brillouin gain spectrums of the respective area portions of the detection optical fiber 15 in the longitudinal direction of the detection optical fiber 15 by detecting the light pertaining to the natural Brillouin scattering phenomenon that was received in a predetermined sampling interval, and obtains the respective Brillouin frequency shift amounts of the respective area portions based on the obtained Brillouin gain spectrums of the respective area portions.

The respective incident lights that entered from the input terminal of the strain and temperature detector 14 are converted into an electric signal by the light-receiving element which performs photoelectric conversion according to the amount of received light, this electric signal is converted into a digital electric signal by the A/D converter, and used for obtaining the Brillouin gain spectrum. Here, an optical band pass filter (hereinafter referred to as the "optical BPF") is used, and this optical BPF is an optical component of a predetermined narrow transmission frequency band; specifically, it is an optical component for transmitting light of a predetermined narrow frequency band and blocking light of a band excluding the foregoing predetermined frequency band, and, for example, the following narrow line width optical band pass filter is used.

FIG. 19 is a diagram explaining the narrow line width optical band pass filter. FIG. 19A is a block diagram showing the configuration of the narrow line width optical band pass filter, and FIG. 19B to FIG. 19D are diagrams explaining the operation of the narrow line width optical band pass filter.

The incident light that entered the input terminal of the strain and temperature detector 14 from the optical circulator 7 is filtered, for example, with the optical BPF shown in FIG. 19, and the light pertaining to the natural Brillouin scattering phenomenon is thereby extracted. Moreover, the incident light is converted into an electric signal by the light-receiving element, filtered by the matched filter, converted into a digital electric signal by the A/D converter, and used for obtaining the Brillouin gain spectrum. Moreover, as needed, the electric signal is amplified by an amplification circuit prior to being digitally converted.

Figure 19A:
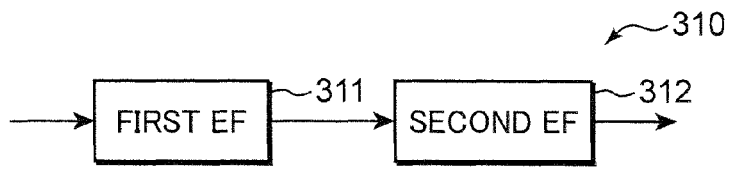
FIGS. 19A, 19B, 19C and 19D are diagrams explaining the narrow line width optical band pass filter.
Figure 19B:
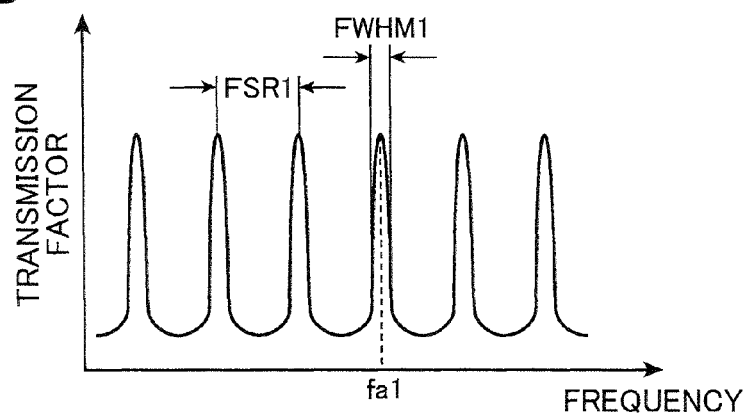

The optical BPF 310 is configured by including, for example, as shown in FIG. 19A, a first Fabry-perotetalon Filter (hereinafter referred to as the "EF") 311, and a second EF 312 that is optically coupled to the first EF 311. With the first EF 311, as shown in FIG. 19B, its half-value full-width FWHM 1 is set to have a frequency width corresponding to a predetermined transmission frequency band in the optical BPF 310, and one center frequency fa1 of its transmission frequency band is set to coincide with the center frequency fa of the transmission frequency band in the optical BPF 310.

Figure 19C:
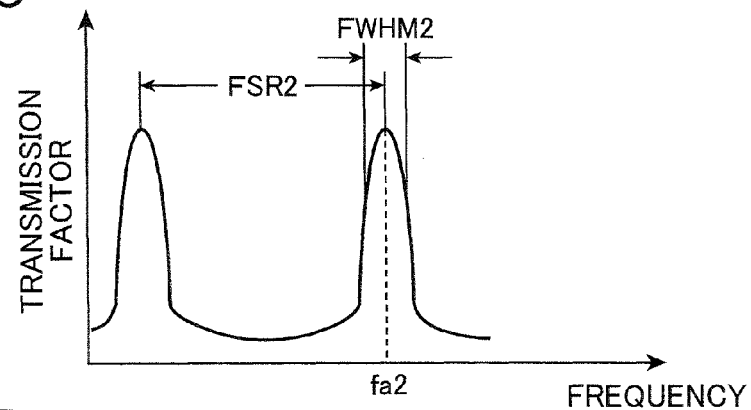

With the second EF 312, as shown in FIG. 19C, its FSR (Free Spectral Range) 2 is set to be wider than the frequency interval between the frequency of the light pulse (sub light pulse and main light pulse) and the frequency of the natural Brillouin backscattered light, its half-value full-width FWHM 2 is set to be greater than the half-value full-width FWHM 1 of the first EF 311 so that its transmission frequency band will include the transmission frequency band of the first EF 311, and one center frequency fa2 of its transmission frequency band is set to coincide with the center frequency fa of the transmission frequency band in the optical BPF 310.

Figure 19D:
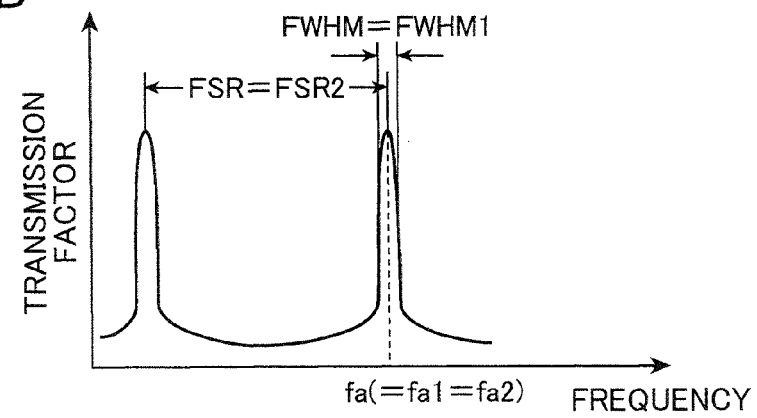

With the optical BPF 310 configured as described above, the light of the frequency corresponding to a predetermined transmission frequency band is transmitted through the first EF 311. Specifically, the light of the frequency corresponding to the half-value full-width FWHM 1 is transmitted for each FSR 1 of the first EF 311. Subsequently, among the lights that were transmitted through the first EF 311, only the light of the frequency corresponding to the transmission frequency band of the center frequency fa1 of the first EF 311 is transmitted through the second EF 312. Thus, the transmission frequency characteristics of the narrow band optical BPF 310 with the foregoing configuration become the characterized obtained by synthesizing the transmission frequency characteristics of the first EF 311 shown in FIG. 19B and the transmission frequency characteristics of the second EF 312 shown in FIG. 19C, and, as shown in FIG. 19D, the center frequency fa of the transmission frequency band thereof becomes the frequency fa1 (=fa2), the half-value full-width FWHM thereof becomes the half-value full-width FWHM 1 of the first EF 311, and the FSR thereof becomes the FSR 2 of the second EF 312. Note that the first EF 311 and the second EF 312 may also be optically coupled in reverse.

Moreover, in the case of a BOTDR, the control processing unit 13 controls the first light source 1, the first ATC 10, the first AFC 11, the light pulse generation unit 3, the optical switch 4 and the optical intensity/polarization adjustment unit 6 by inputting and outputting signals to and from the strain and temperature detector 14 so that the distribution of the strain and temperature of the detection optical fiber 15 in the longitudinal direction of the detection optical fiber 15 can be measured with high spatial resolution and to a greater distance.

With the distributed optical fiber sensor FS of the BOTDR configured as described above, the sub light pulse and the main light pulse generated by the first light source 1 and the light pulse generation unit 3 enter from one end of the detection optical fiber 15 via the optical switch 4, the optical coupler 5, the optical intensity/polarization adjustment unit 6, the optical circulator 7 and the optical connector 9. The spread spectrum system is used for the main light pulse. The light (natural Brillouin backscattered light) that was subject to the action of the natural Brillouin scattering phenomenon in the detection optical fiber 15 is output from one end of the detection optical fiber 15, and received by the strain and temperature detector 14. Subsequently, the Brillouin gain spectrum time domain reflection analysis ($B^{Gain}$-OTDR) is performed by the strain and temperature detector 14, and the Brillouin frequency shift amount is thereby detected. Note that the light pertaining to the natural Brillouin scattering phenomenon is the natural Brillouin backscattered light.

Even with the distributed optical fiber sensor FS of the BOTDR configured as described above, since the spatial resolution and the measurable distance can be independently set by configuring the light pulse from a main light pulse using the spread spectrum system, and a sub light pulse, the measurable distance can be extended even farther and measured while enabling the measurement of the strain and temperature with high spatial resolution.

Figure 20A:
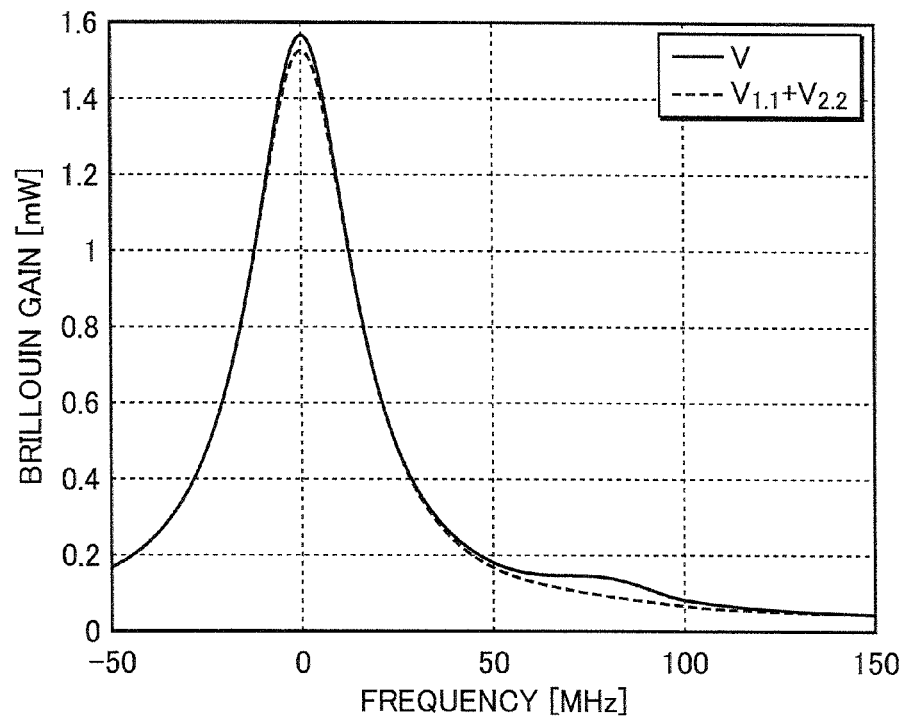
FIGS. 20A and 20B are diagrams explaining the method of obtaining the Brillouin frequency shift by subtracting the constituent elements from the overall spectrum.
Figure 20B:
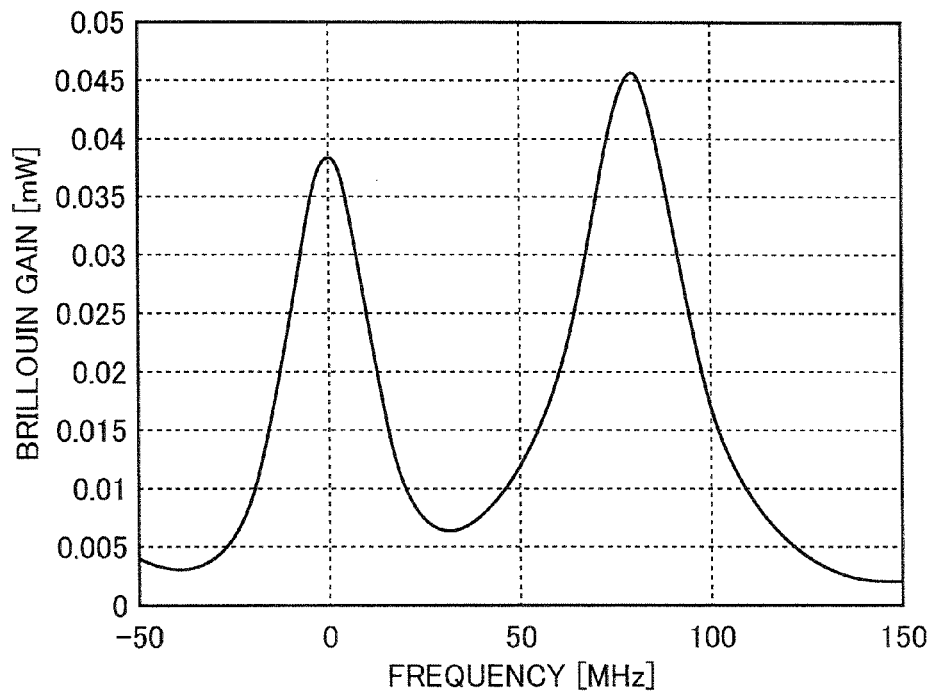

FIG. 20 is a diagram explaining the method of obtaining the Brillouin frequency shift by subtracting the constituent elements from the overall spectrum. In FIG. 20, the horizontal axis is the frequency represented in MHz units, and the vertical axis is the Brillouin gain represented in mW units. FIG. 20A shows the first to third Brillouin spectrums, and FIG. 20B shows the results upon subtracting the second and third Brillouin spectrums from the overall spectrum. The solid line of FIG. 20A shows the first Brillouin spectrum as the overall Brillouin spectrum, and the broken line shows the sum of the second Brillouin spectrum and the third Brillouin spectrum as the constituent elements thereof.

Note that, in the distributed optical fiber sensor FS of the BOTDA according to this embodiment, foremost, the sub light pulse and the main light pulse as the pump light and the continuous light as the probe light are caused to enter the detection optical fiber 15 based on the control of the control processing unit 13, and the strain and temperature detector 14 obtains the first Brillouin spectrum based on the light pertaining to the first stimulated Brillouin scattering phenomenon that is output from the detection optical fiber 15 in the foregoing case. Subsequently, the main light pulse as the pump light and the continuous light as the probe light are caused to enter the detection optical fiber 15 based on the control of the control processing unit 13, and the strain and temperature detector 14 obtains the second Brillouin spectrum based on the light pertaining to the second stimulated Brillouin scattering phenomenon that is output from the detection optical fiber 15 in the foregoing case. Subsequently, the strain and temperature detector 14 may obtain the difference between the first Brillouin spectrum and the second Brillouin spectrum, and measure the stain and temperature generated in the detection optical fiber 15 based on the obtained difference.

Otherwise, the sub light pulse as the pump light and the continuous light as the probe light are caused to enter the detection optical fiber 15 based on the control of the control processing unit 13, and the strain and temperature detector 14 obtains the third Brillouin spectrum based on the light pertaining to the third stimulated Brillouin scattering phenomenon that is output from the detection optical fiber 15 in the foregoing case. Subsequently, the strain and temperature detector 14 may obtain the difference between the first Brillouin spectrum and the third Brillouin spectrum, and measure the strain and temperature generated in the detection optical fiber 15 based on the obtained difference.

As a result of adopting the foregoing configuration, unneeded components of the Brillouin spectrum can be suppressed upon obtaining the Brillouin frequency shift amount in the BOTDA, and the Brillouin frequency shift amount can be obtained more easily with high precision. Consequently, the strain and temperature generated in the detection optical fiber can be obtained more easily with high precision.

Otherwise, for example, in FIG. 20, foremost, the first Brillouin spectrum (solid line of FIG. 20A) is obtained by causing the distributed optical fiber sensor FS to operate as described above. Subsequently, the second and third Brillouin spectrums are respectively obtained by causing the distributed optical fiber sensor FS to operate as described above. Subsequently, the strain and temperature detector 14 obtains the difference (FIG. 20B) between the first Brillouin spectrum (solid line of FIG. 20A) and the sum of the second Brillouin spectrum and the third Brillouin spectrum (broken line of FIG. 20A). Subsequently, the strain and temperature detector 14 may measure the strain and temperature generated in the detection optical fiber 15 based on the obtained difference.

As a result of adopting the foregoing configuration, unneeded components of the Brillouin spectrum can be suppressed upon obtaining the Brillouin frequency shift amount in the BOTDA, and the Brillouin frequency shift amount can be obtained more easily with high precision. Consequently, the strain and temperature generated in the detection optical fiber can be obtained even more easily with even higher precision.

Moreover, in the distributed optical fiber sensor FS of the BOTDR according to this embodiment, foremost, the sub light pulse and the main light pulse are caused to enter the detection optical fiber 15 based on the control of the control processing unit 13, and the strain and temperature detector 14 obtain the first Brillouin gain spectrum based on the light pertaining to the first natural Brillouin scattering phenomenon that is output from the detection optical fiber 15 in the foregoing case. Subsequently, the main light pulse is caused to enter the detection optical fiber 15 based on the control of the control processing unit 13, and the strain and temperature detector 14 obtains the second Brillouin gain spectrum based on the light pertaining to the second natural Brillouin scattering phenomenon that is output from the detection optical fiber 15 in the foregoing case. Subsequently, the strain and temperature detector 14 may obtain the difference between the first Brillouin gain spectrum and the second Brillouin gain spectrum, and measure the strain and temperature generated in the detection optical fiber 15 based on the obtained difference.

Otherwise, the sub light pulse is caused to enter the detection optical fiber 15 based on the control of the control processing unit 13, and the strain and temperature detector 14 obtains the third Brillouin gain spectrum based on the light pertaining to the third natural Brillouin scattering phenomenon that is output from the detection optical fiber 15 in the foregoing case. Subsequently, the strain and temperature detector 14 may obtain the difference between the first Brillouin gain spectrum and the third Brillouin gain spectrum, and measure the strain and temperature generated in the detection optical fiber 15 based on the obtained difference.

As a result of adopting the foregoing configuration, unneeded components of the Brillouin gain spectrum can be suppressed upon obtaining the Brillouin frequency shift amount in the BOTDR, and the Brillouin frequency shift amount can be obtained more easily with high precision.

Consequently, the strain and temperature generated in the detection optical fiber can be obtained more easily with high precision.

Otherwise, upon obtaining the second and third Brillouin gain spectrums, the strain and temperature detector 14 obtain the difference between the first Brillouin gain spectrum, and the sum of the second Brillouin gain spectrum and the third Brillouin gain spectrum, and measure the strain and temperature generated in the detection optical fiber 15 based on the obtained difference.

As a result of adopting the foregoing configuration, unneeded components of the Brillouin gain spectrum can be suppressed upon obtaining the Brillouin frequency shift amount in the BOTDR, and the Brillouin frequency shift amount can be obtained more easily with high precision. Consequently, the strain and temperature generated in the detection optical fiber can be obtained even more easily with even higher precision.

The experimental results in the distributed optical fiber sensor FS using the light pulse configured from the foregoing non-modulated sub light pulse and the main light pulse using the spread spectrum system are now explained. These experimental result were obtained, for example, by obtaining the first Brillouin spectrum and the sum of the second Brillouin spectrum and the third Brillouin spectrum in the BOTDA, and measuring the Brillouin frequency shift amount caused by the strain generated in the detection optical fiber based on the obtained difference.

Figure 21A:
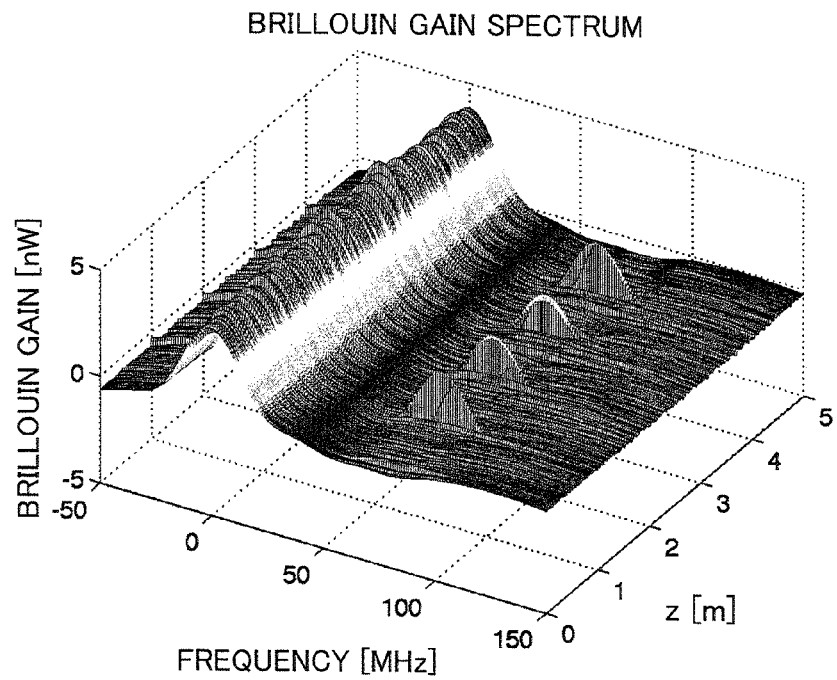
FIGS. 21A and 21B are diagrams showing the experimental result of the distributed optical fiber sensor in the case of using the pump light having the configuration shown in FIG. 6A.
Figure 21B:
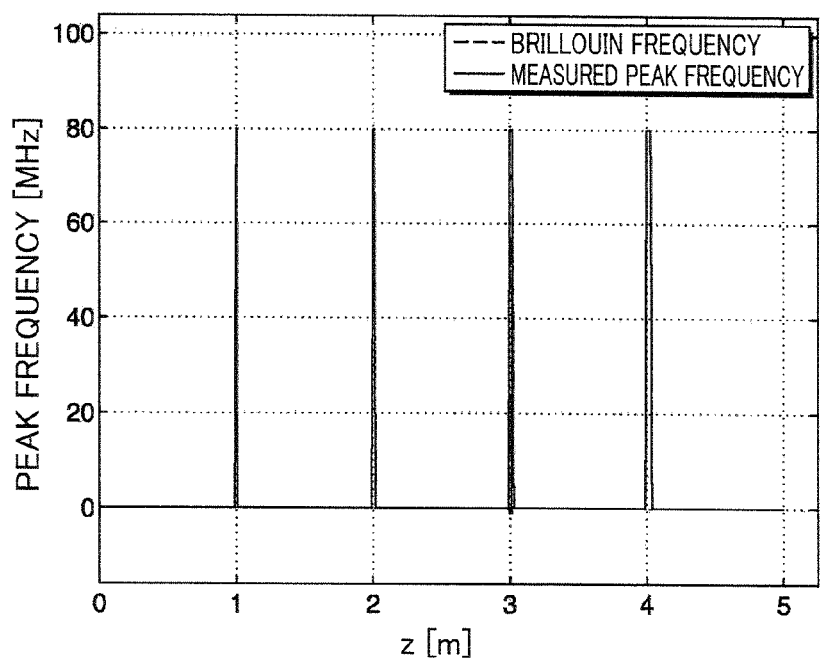

FIG. 21 is a diagram showing the experimental result of the distributed optical fiber sensor in the case of using the pump light having the configuration shown in FIG. 6A. FIG. 21A shows the Brillouin gain spectrum, and FIG. 21B shows the Brillouin frequency shift. The x axis of FIG. 21A is the frequency (MHz), the y axis is the Brillouin gain (nW), and the z axis is the distance (m) of the detection optical fiber 15 in the longitudinal direction. The horizontal axis of FIG. 21B is the distance (m) of the detection optical fiber 15 in the longitudinal direction, and the vertical axis is the peak frequency (MHz). The solid line shows the measured peak frequency and the broken line shows the Brillouin frequency shift.

In this experiment, the pump light is configured, as shown in FIG. 6(A), from a sub light pulse with a pulse width of 30 ns and a main light pulse with a pulse width of 12.7 ns which is successively subsequent to the sub light pulse, and the main light pulse is divided into 127 cells with a cell width of 0.1 ns, and the respective cells are modulated (encoded) with the M sequence binary code and then subject to spectral spread encoding.

In the detection optical fiber 15, as shown in Table 1, a strain of 80 MHz (=approximately 1600με) based on the Brillouin frequency shift conversion is provided in advance to the respective zones of a first zone from z=100 cm to z=101 cm, a second zone from z=200 cm to z=202 cm, a third zone from z=300 cm to z=303 cm, and a fourth zone from z=400 cm to z=404 cm.

TABLE 1

|  | Width | | | | | | | | |
| --- | --- | --- | --- | --- | --- | --- | --- | --- | --- |
|  | 100 | 1 | 99 | 2 | 98 | 3 | 97 | 4 | 96 |
| Frequency shift [MHz] | 0 | 80 | 0 | 80 | 0 | 80 | 0 | 80 | 0 |

(1600 με)

When pump light which partially uses the spread spectrum system is caused to enter the foregoing detection optical fiber 15 and measured, the Brillouin gain spectrum shown in FIG. 21A is obtained, and, consequently, the Brillouin frequency shift shown in FIG. 21B is obtained. As shown in FIG. 21, the Brillouin frequency shift amount based on the strain of a size that is provided in advance is measured at the respective strain positions shown in Table 1, and it can be understood that the strain is obtained with high precision and with high spatial resolution.

As described above, the strain can be obtained with high precision and with high spatial resolution even when using the spread spectrum system in the main light pulse. In addition, as described above, as a result of configuring the pump light from a main light pulse using the spread spectrum system and a sub light pulse, the spatial resolution and the measurable distance can be set independently. Thus, the measurable distance can be extended even farther and measured while enabling the measurement of the strain with high spatial resolution.

Note that, although the foregoing embodiments used the pump light (sub light pulse and main light pulse) of the mode shown in FIG. 6, the configuration is not limited thereto, and, for example, the pump light (sub light pulse and main light pulse) of the mode shown in FIG. 22 may also be sued.

Figure 22A:
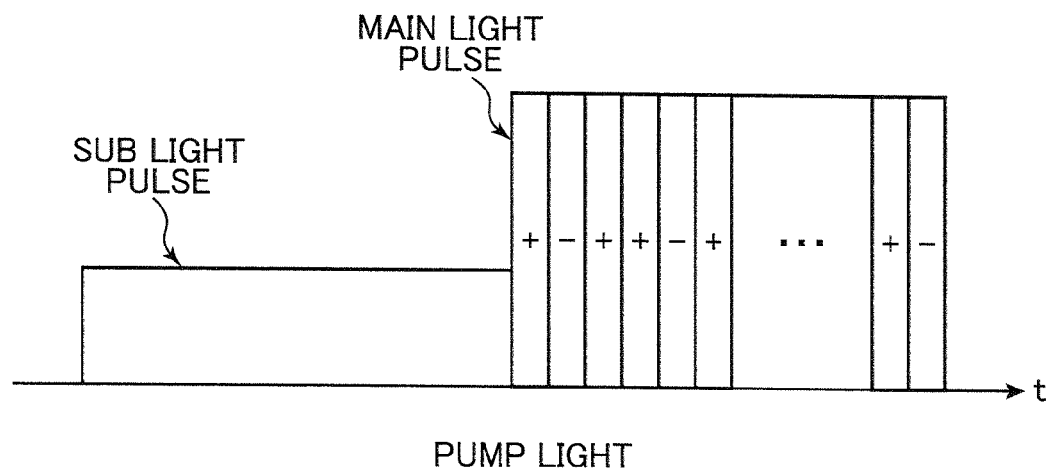
FIGS. 22A and 22B are diagrams explaining another configuration of the pump light (sub light pulse and main light pulse).
Figure 22B:
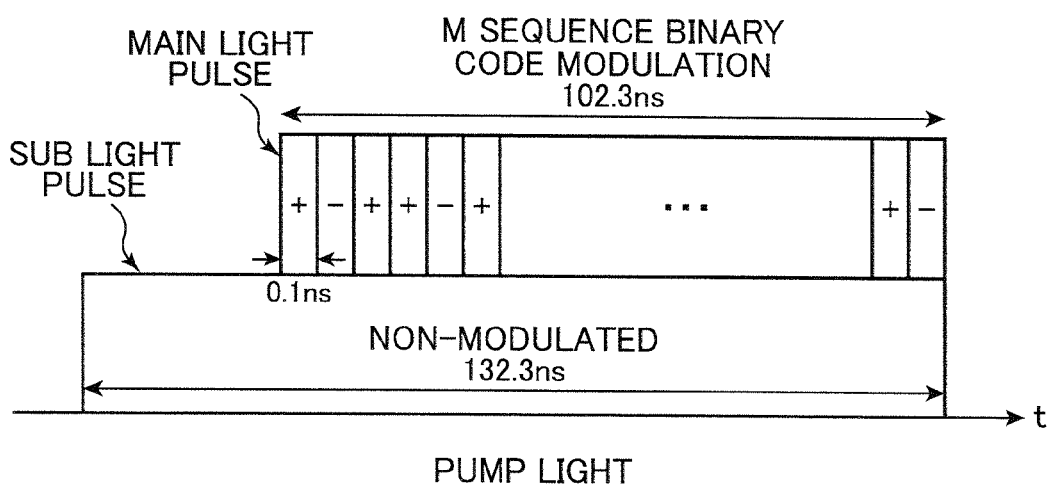

FIG. 22 is a diagram explaining another configuration of the pump light (sub light pulse and main light pulse), wherein FIG. 22A shows the first configuration as another configuration of the pump light, and FIG. 22B shows the second configuration as another configuration of the pump light.

With the pump light shown in FIG. 6A, the optical intensity of the sub light pulse was the same level as the optical intensity of the main light pulse, and, for example, as shown in FIG. 22A, the pump light may be such that the optical intensity of the sub light pulse is smaller than the optical intensity of the main light pulse. Since the sub light pulse plays the role of causing the acoustic phonon to rise temporally before the main light pulse as described above, a large optical intensity as with the main light pulse is not required, and may be smaller than the optical intensity of the main light pulse.

Moreover, the respective pump lights shown in FIG. 6A and FIG. 22A are configured so that the sub light pulse temporally precedes the main light pulse without overlapping with the main light pulse. However, for example, as shown in FIG. 22B, the pump light may also have a portion where the main light pulse and the sub light pulse temporally overlap. With a pump light having this kind of configuration, from the perspective of causing the acoustic phonon to rise based on the sub light pulse by temporally preceding the main light pulse, preferably, the portion of the sub light pulse that is not overlapping with the main light pulse temporally precedes the main light pulse, and, more preferably, the portion of the sub light pulse that is not overlapping with the main light pulse is greater than the time that it takes for the acoustic phonon to completely rise; for example, approximately 30 ns or more.

The experimental results in cases of using, in the distributed optical fiber sensor FS, the pump light configured from the main light pulse using the spread spectrum system, and the sub light pulse with a portion overlapping with the main light pulse are now explained. As with the experimental results shown in FIG. 21, these experimental results were obtained, for example, by obtaining the difference between the first Brillouin spectrum and the sum of the second Brillouin spectrum and the third Brillouin spectrum in the BOTDA, and measuring the Brillouin frequency shift amount caused by the strain generated in the detection optical fiber based on the obtained difference.

Figure 23A:
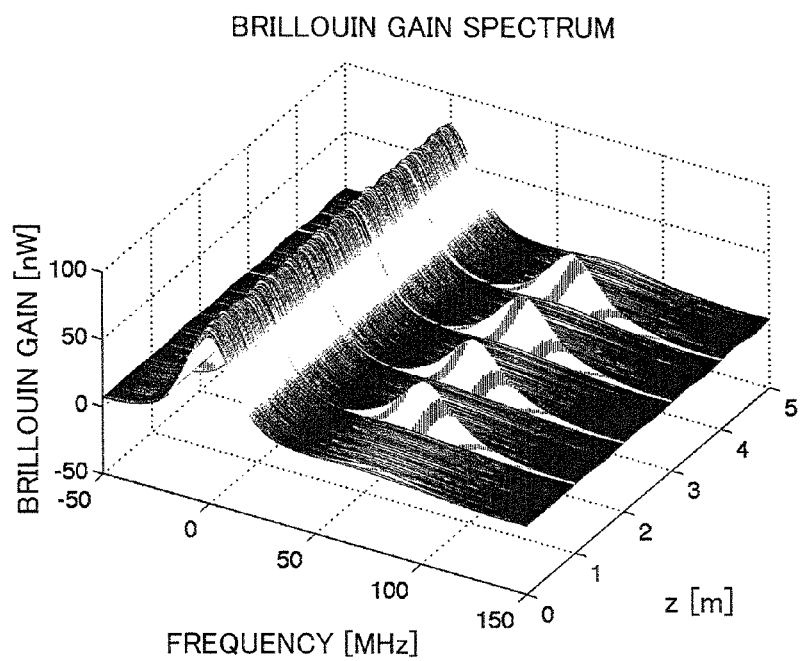
FIGS. 23A and 23B are diagrams showing the experimental result of the distributed optical fiber sensor in the case of using the pump light having the configuration shown in FIG. 22B.
Figure 23B:
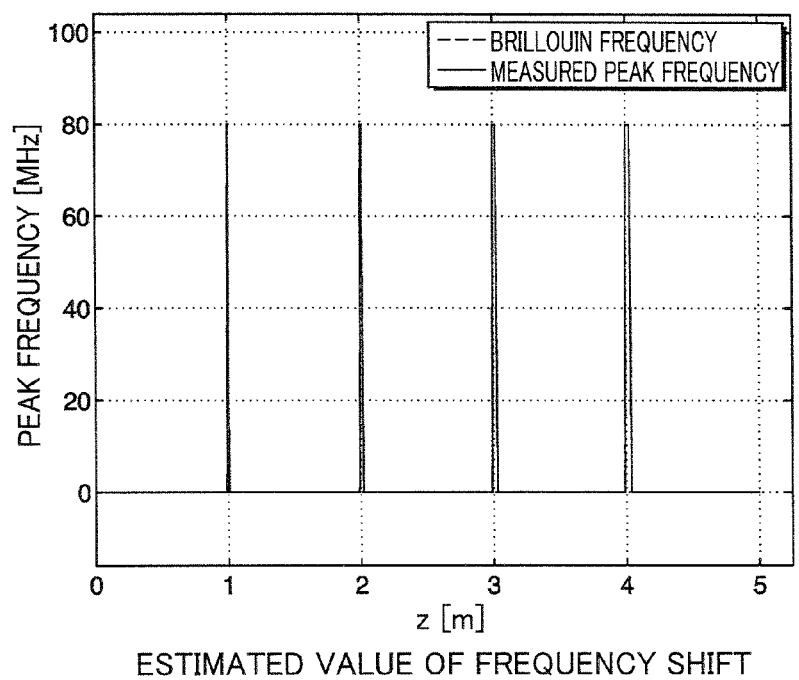

FIG. 23 is a diagram showing the experimental result of the distributed optical fiber sensor in the case of using the pump light having the configuration shown in FIG. 22B. FIG. 23A shows the Brillouin gain spectrum, and FIG. 23B shows the Brillouin frequency shift. The respective axes in FIG. 23A and FIG. 21B are the same as those in FIG. 21A and FIG. 21B.

In this experiment, the pump light is configured, as shown in FIG. 22B, from a sub light pulse with a pulse width of 132.3 ns and a main light pulse with a pulse width of 102.3 ns which overlaps with the sub light pulse by being temporally delayed by 30 ns relative to the sub light pulse, and the main light pulse is divided into 1023 cells with a cell width of 0.1 ns, and the respective cells are modulated (encoded) with the M sequence binary code and then subject to spectral spread encoding.

In the detection optical fiber 15, in the same manner described above and as shown in Table 1, a strain of 80 MHz (=approximately 1600με) based on the Brillouin frequency shift conversion is provided in advance to the respective zones of the first to fourth zones.

When pump light which configured as shown in FIG. 22B is caused to enter the foregoing detection optical fiber 15 and measured, the Brillouin gain spectrum shown in FIG. 23A is obtained, and, consequently, the Brillouin frequency shift shown in FIG. 23B is obtained. As shown in FIG. 23, the Brillouin frequency shift amount based on the strain of a size that is provided in advance is measured at the respective strain positions shown in Table 1, and it can be understood that the strain is obtained with high precision and with high spatial resolution.

As described above, the strain can be obtained with high precision and with high spatial resolution even when there is an overlapping portion of the sub light pulse and the main light pulse. In addition, as described above, as a result of configuring the pump light from a main light pulse using the spread spectrum system and a sub light pulse, the spatial resolution and the measurable distance can be set independently. Thus, the measurable distance can be extended even farther and measured while enabling the measurement of the strain with high spatial resolution.

Another mode of the pump light (sub light pulse and main light pulse) that is used in the distributed optical fiber sensor FS of this embodiment is now explained.

Figure 24A:
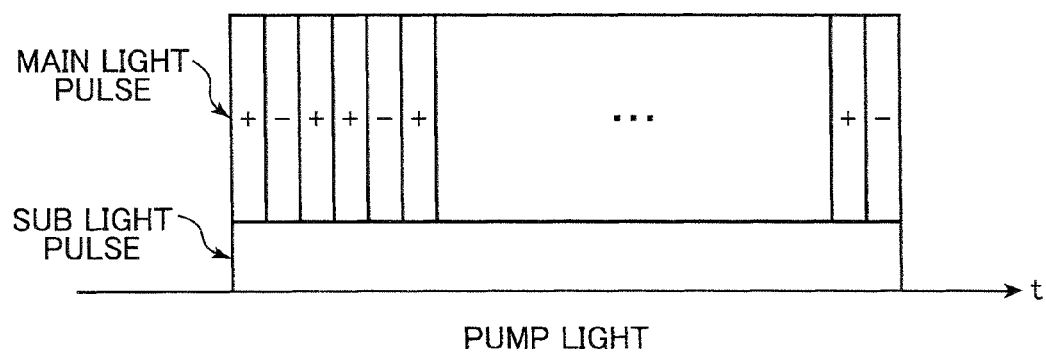
FIGS. 24A and 24B are diagrams explaining yet another configuration of the pump light (sub light pulse and main light pulse) and the matched filter.
Figure 24B:
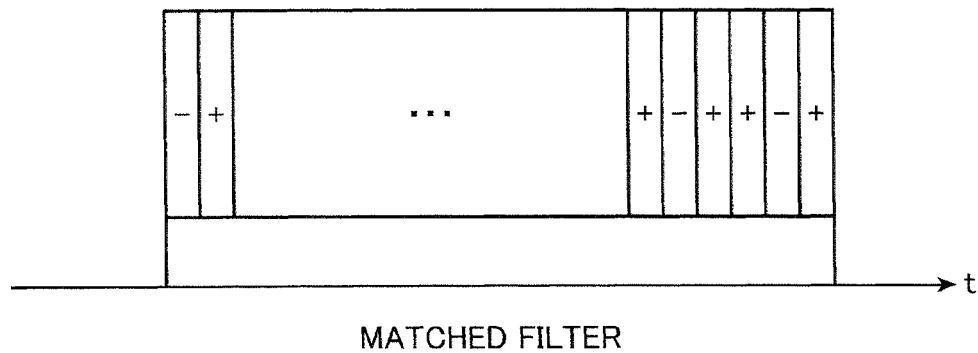
Figure 25:
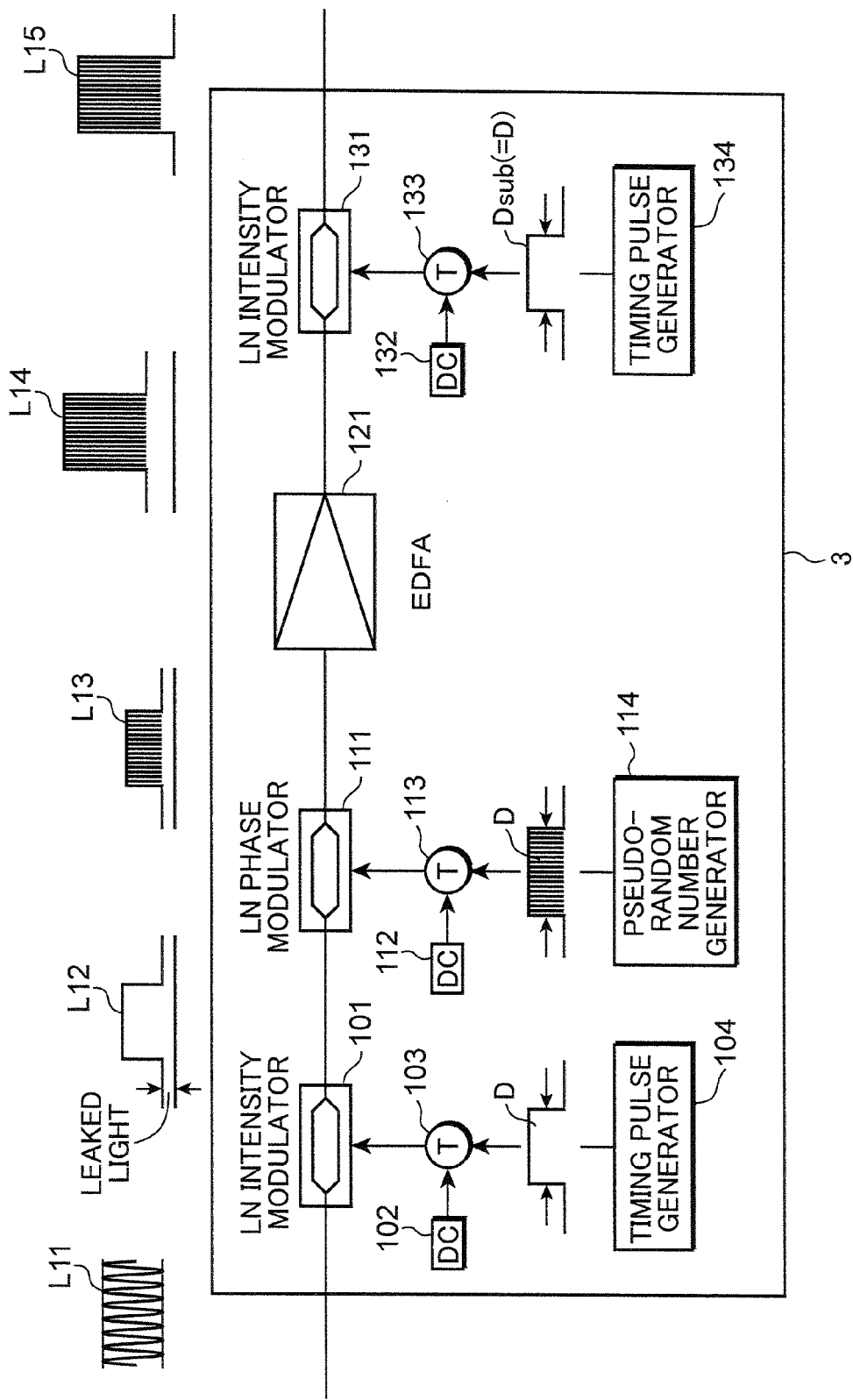
FIG. 25 is a diagram explaining the configuration and operation of the light pulse generation unit for generating the pump light having the configuration shown in FIG. 24A.

FIG. 24 is a diagram explaining yet another configuration of the pump light (sub light pulse and main light pulse) and the matched filter, wherein FIG. 24A shows the configuration of the pump light, and FIG. 24B shows the matched filter. FIG. 25 is a diagram explaining the configuration and operation of the light pulse generation unit for generating the pump light having the configuration shown in FIG. 24A.

The pump light configured as shown in FIG. 22B was configured from a sub light pulse with a portion which overlaps with the main light pulse while having a portion which temporally precedes the main light pulse, and a main light pulse. However, as shown in FIG. 24A, the pump light may also be configured from a sub light pulse which temporally and completely overlaps with the main light pulse without having a portion which temporally precedes the main light pulse, and a main light pulse. Specifically, the rise timing and fall timing of the sub light pulse respectively coincide with the rise timing and fall timing of the main light pulse.

This kind of pump light configured as shown in FIG. 24A can be generated, for example, from the light pulse generation unit 3 configured as shown in FIG. 25. With the light pulse generation unit 3 configured as shown in FIG. 25, its configuration coincides with the configuration of the light pulse generation unit 3 and the optical switch 4 shown in FIG. 5, and its operation differs from the operation of the light pulse generation unit 3 shown in FIG. 5. Thus, the explanation of such configuration is omitted, and only its operation is explained.

Foremost, in order to generate the pump light configured as shown in FIG. 24A, the LN intensity modulator 101 is turned ON so that a predetermined level of light (leaked light) is leaked (output) in order to generate a sub light pulse.

The continuous light L11 (=L1) output from the first light source 1 enters the LN intensity modulator 101 of the light pulse generation unit 3 via the optical coupler 2. When the continuous light L11 is entered, the LN intensity modulator 101 outputs the leaked light.

In the light pulse generation unit 3, at the generation timing of the pump light, the operation timing pulse of the pulse width D corresponding to the pulse width D of the main light pulse is output from the timing pulse generator 104 to the multiplier 103, multiplied with the DC voltage input from the DC power source 102, and the DC voltage of the pulse width D is applied to the signal electrode of the LN intensity modulator 101. Consequently, the continuous light L11 is output as the light pulse L12 in which the light pulse of the pulse width D is superposed on the leaked light based on the LN intensity modulator 101.

Subsequently, in the light pulse generation unit 3, at the generation timing of the main light pulse, a pseudo-random number is sequentially output from the pseudo-random number generator 114 to the multiplier 113 at the temporal timing of the cell width during the duration D corresponding to the pulse width D of the main light pulse, multiplied with the DC voltage input from the DC power source 112, and the DC voltage that was modulated with the M sequence binary code is sequentially applied to the signal electrode of the LN phase modulator 111 at the temporal timing of the cell width during the duration D from the generation timing of the main light pulse. Consequently, the light pulse L12 is output as the light pulse L13 in which the portion (corresponds to the main light pulse) modulated with the M sequence binary code is superposed on the leaked light based on the LN phase modulator 111.

Subsequently, in the EDFA 121, the light pulse L13 is amplified until it becomes a predetermined optical intensity and output as the light pulse L14.

In addition, in the light pulse generation unit 3, according to the generation timing of the pump light, the operation timing pulse of the pulse width $D_{sub}$ (=D) corresponding to the pulse width $D_{sub}$ (=pulse width D of the main light pulse) of the sub light pulse is output from the timing pulse generator 134 to the multiplier 133, multiplied with the DC voltage input from the DC power source 132, and the DC voltage of the pulse width $D_{sub}$ (=D) is applied to the signal electrode of the LN intensity modulator 131. The light pulse L14 is thereby output as the pump light L15 configured from a non-modulated sub light pulse having the pulse width $D_{sub}$ (=D) and the main light pulse encoded with the spread spectrum system and having the pulse width D (=$D_{sub}$) and in which the main light pulse is temporally and completely overlapped on the sub light pulse after noise such as amplified spontaneous emission associated with the light pulse L14 at the EDFA 121 is removed with the LN intensity modulator 131 and the light (leaked light amplified by the EDFA 121) caused by the leaked light before and after the light pulse L14 is removed.

The light pulse (sub light pulse and main light pulse) configured as shown in FIG. 6A, FIG. 22(A), FIG. 22(B) and FIG. 24(A) can also be used in the distributed optical fiber sensor of the BOTDR as with the distributed optical fiber sensor of the BOTDA. Note that, with the BOTDR, since the acoustic phonon that is excited by the thermal noise is used as described above, the sub light pulse does not necessarily have to temporally precede the main light pulse. Needless to say, the sub light pulse may also temporally precede the main light pulse.

Moreover, as the pump light (sub light pulse and main light pulse), in addition to the stepwise pulse described in Brochure of International Publication No. 2006/001071, the following pulse may also be used.

Figure 26:
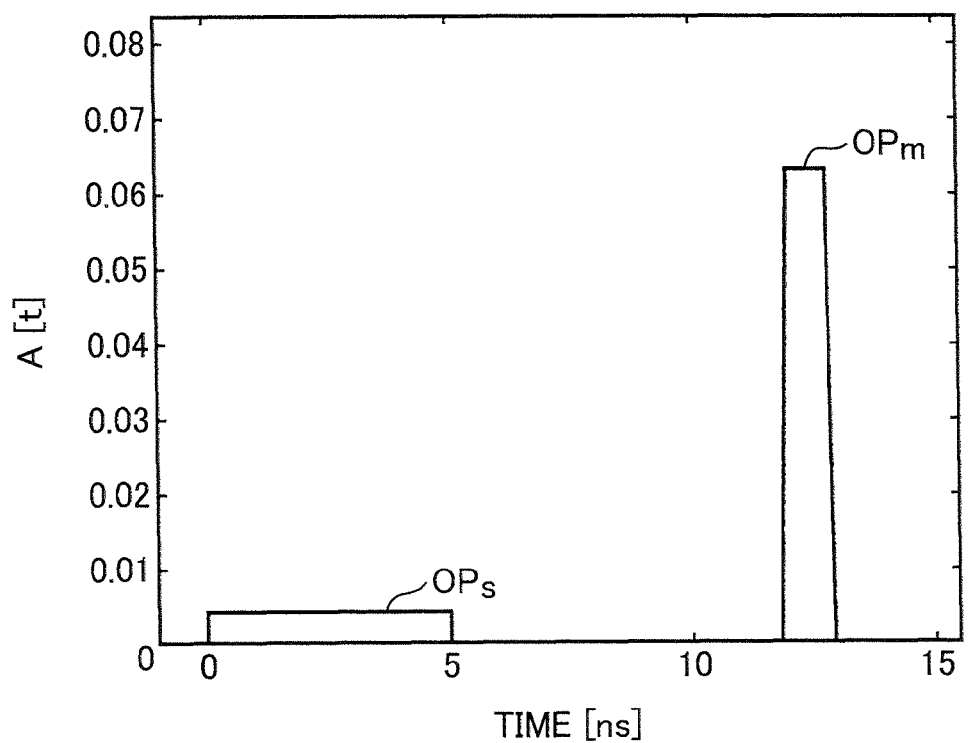
FIG. 26 is a diagram showing the waveform of the sub light pulse and the main light pulse of another example.

FIG. 26 is a diagram showing the waveform of the sub light pulse and the main light pulse of another example. The horizontal axis of the respective drawings below is the time represented in ns units, and the vertical axis is the optical intensity. In the example shown in FIG. 26, the main light pulse OPm is a rectangular shape of the first predetermined optical intensity P1 in the first predetermined pulse width D1 (optical intensity P is constant as the first predetermined optical intensity P1 between the first predetermined pulse widths D1), and the sub light pulse OPs is a rectangular shape of the second predetermined optical intensity P2 in the second predetermined pulse width D2 (optical intensity P is constant as the second predetermined optical intensity P2 between the second predetermined pulse widths D2). In addition, a predetermined time is opened between the sub light pulse OPs and the main light pulse OPm. Thus, the second predetermined pulse width D2 of the sub light pulse OPs is of a duration that is shorter than the time from the rise of the sub light pulse OPs to the rise of the main light pulse OPm.

For example, the main light pulse OPm has a pulse width D1 of 1 ns and an optical intensity P1 of 0.062, the sub light pulse OPs has a pulse width D2 of 5 ns and an optical intensity P2 of 0.005, and a time of 7 ns is opened between the sub light pulse OPs and the main light pulse OPm (from the fall of the sub light pulse OPs to the rise of the main light pulse OPm).

Figure 27:
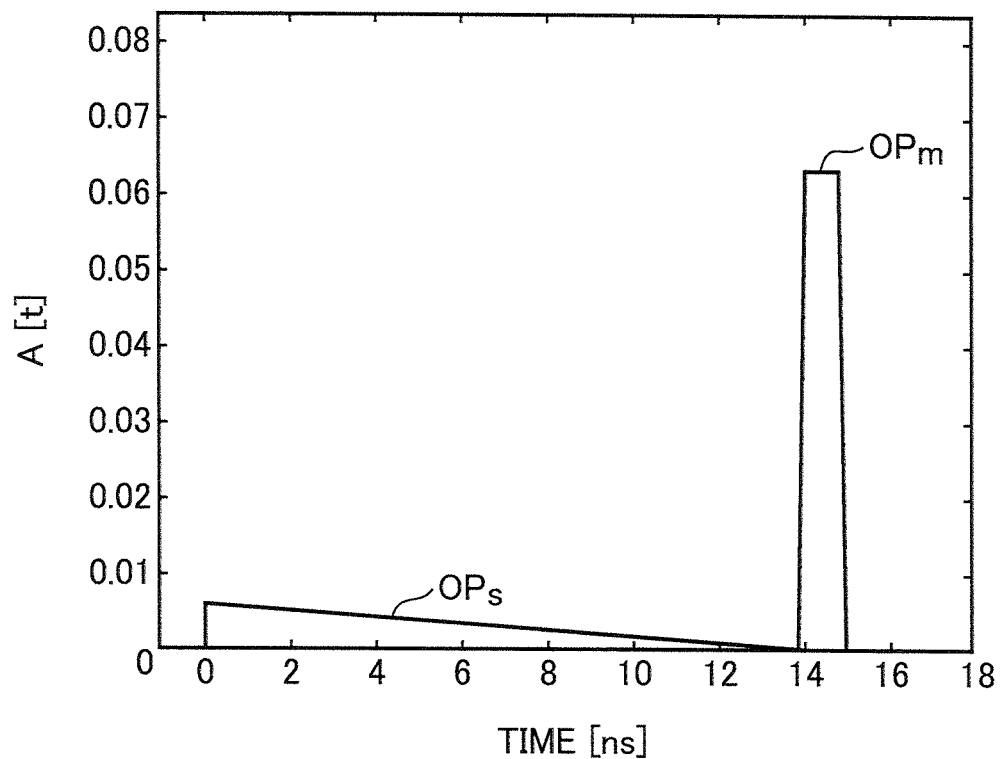
FIG. 27 is a diagram showing the waveform of the sub light pulse and the main light pulse of another example.

FIG. 27 is a diagram showing the waveform of the sub light pulse and the main light pulse of another example. In the example shown in FIG. 27, the main light pulse OPm is a rectangular shape of the first predetermined optical intensity P1 in the first predetermined pulse width D1, the sub light pulse OPs is a right triangle shape which rises at the second predetermined optical intensity (maximum optical intensity) P2 in the second predetermined pulse width D2 and in which the optical intensity P gradually decreases according to the lapse of time, and the main light pulse OPm rises approximately immediately after the completion of the sub light pulse OPs. For example, the main light pulse OPm has a pulse width D1 of 1 ns and an optical intensity P1 of 0.062, and the sub light pulse OPs has a pulse width D2 of 13 ns and a rise optical intensity P2 of 0.005.

Figure 28A:
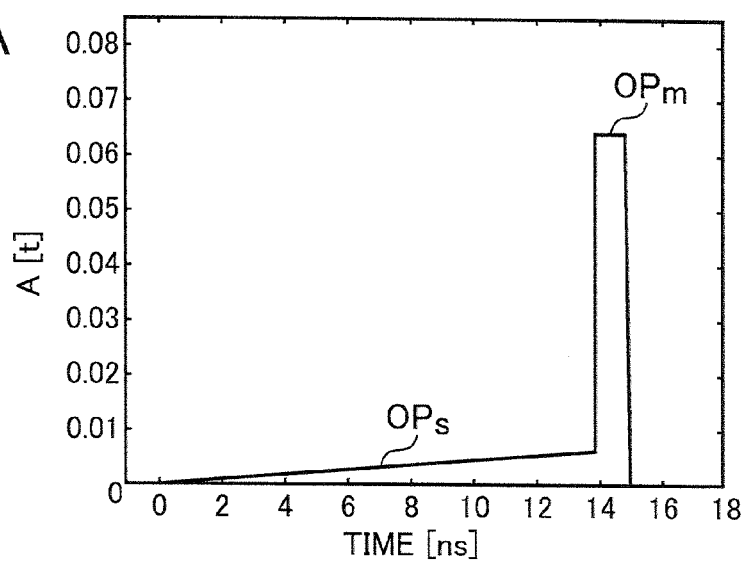
FIGS. 28A, 28B and 28C are diagrams showing the waveform of the sub light pulse and the main light pulse of another example.

FIG. 28 is a diagram showing the waveform of the sub light pulse and the main light pulse of another example. In the example shown in FIG. 28(A), the main light pulse OPm is a rectangular shape of the first predetermined optical intensity P1 in the first predetermined pulse width D1, the sub light pulse OPs is a right triangle shape in which the optical intensity P gradually increases according to the lapse of time up to the second predetermined optical intensity (maximum optical intensity) P2 in the second predetermined pulse width D2, and the first light pulse OPm rises approximately immediately after the completion of the second light pulse OPs. For example, the main light pulse OPm has a pulse width D1 of 1 ns and an optical intensity P1 of 0.062, and the sub light pulse OPs has a pulse width D2 of 13 ns and a fall optical intensity P2 of 0.005.

Figure 28B:
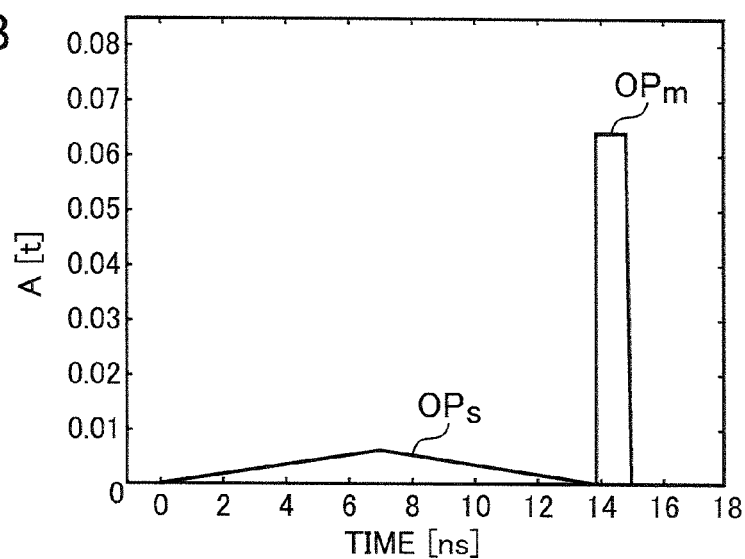

In the example shown in FIG. 28B, the main light pulse OPm is a rectangular shape of the first predetermined optical intensity P1 in the first predetermined pulse width D1, the sub light pulse OPs is an isosceles triangle shape in which the optical intensity P gradually increases up to the second predetermined optical intensity (maximum optical intensity) P2 according to the lapse of time in the second predetermined pulse width D2 and thereafter gradually decreases according to the lapse of time, and the main light pulse OPm rises approximately immediately after the completion of the sub light pulse OPs. For example, the main light pulse OPm has a pulse width D1 of 1 ns and an optical intensity P1 of 0.062, and the sub light pulse OPs has a pulse width D2 of 13 ns and a maximum optical intensity P2 at the center of the pulse of 0.005.

Figure 28C:
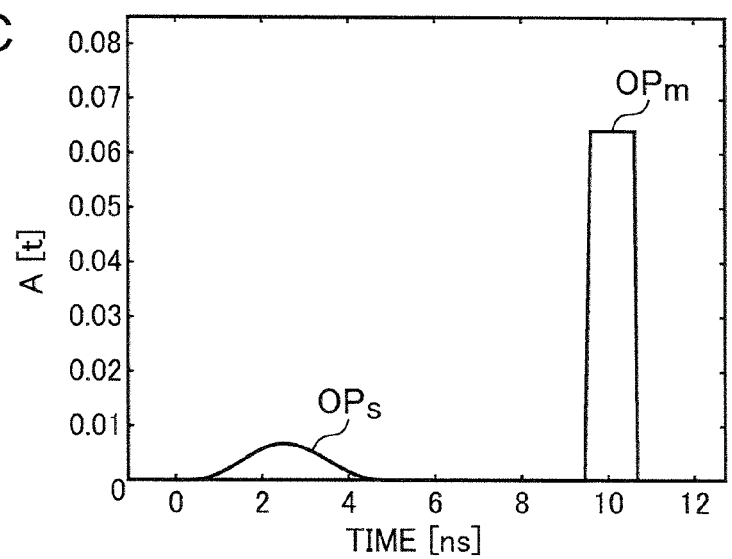

As shown in FIG. 28(C), the main light pulse OPm is a rectangular shape of the first predetermined optical intensity P1 in the first predetermined pulse width D1, the sub light pulse OPs is a Gaussian curve shape in which the optical intensity P gradually increases up to the second predetermined optical intensity (maximum optical intensity) P2 according to the lapse of time in the second predetermined pulse width D2 and thereafter gradually decreases according to the lapse of time. In addition, a predetermined time is opened between the sub light pulse OPs and the main light pulse OPm. Thus, the second predetermined pulse width D2 of the sub light pulse OPs is a duration that is shorter than the time from the rise of the sub light pulse OPs to the rise of the main light pulse OPm. For example, the main light pulse OPm has a pulse width D1 of 1 ns and an optical intensity P1 of 0.062, the sub light pulse OPs has a pulse width D2 of 5 ns and a maximum optical intensity P2 of 0.005, and a time of 4.5 ns is opened between the sub light pulse OPs and the main light pulse OPm (from the fall of the sub light pulse OPs to the rise of the main light pulse OPm).

Figure 29:
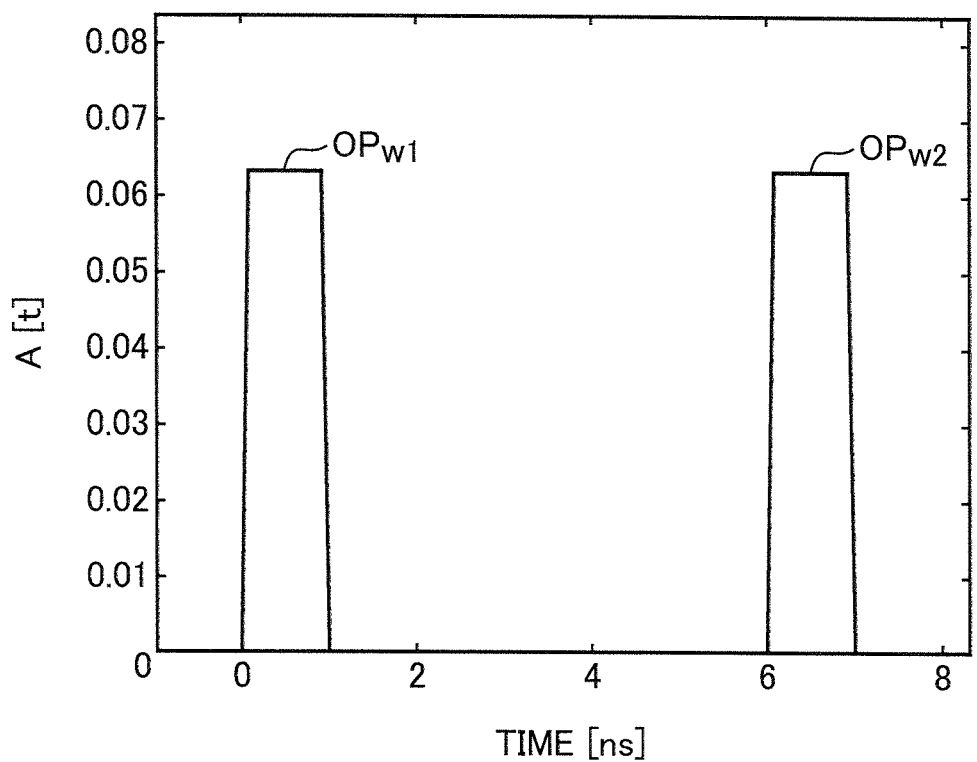
FIG. 29 is a diagram showing the waveform of the sub light pulse and the main light pulse of another example.

FIG. 29 is a diagram showing the waveform of the sub light pulse and the main light pulse of another example. In the example shown in FIG. 29, the pulse width and optical intensity of the first and second light pulses OPw1, OPw2 are the same, and a predetermined is opened between the first light pulse OPw1 and the second light pulse OPw2. For example, the first and second light pulses OPw1, OPw2 have a pulse width of 1 ns, and optical intensity of 0.062, and a predetermined time of 5 ns.

Note that, with the distributed optical fiber sensor FS of the BOTDA in the foregoing embodiments, although the Brillouin spectrum was measured by fixing the frequency of the pump light (sub light pulse and main light pulse) and sweeping the frequency of the probe light (continuous light) in a predetermined frequency range, the Brillouin spectrum may also be measured by fixing the frequency of the probe light and sweeping the frequency of the pump light in a predetermined frequency range.

Moreover, in the foregoing embodiments, the distributed optical fiber sensor was configured so that the distributed optical fiber sensor for the Brillouin optical time domain analysis (BOTDA), the distributed optical fiber sensor for the Brillouin spectrum time domain reflection analysis (BOTDR), and the coherent optical time domain reflectometer (COTDR) using the Rayleigh scattering phenomenon can be executed integrally. However, a distributed optical fiber sensor capable of performing the Brillouin optical time domain analysis, a distributed optical fiber sensor capable of performing the Brillouin spectrum time domain reflection analysis, and a distributed optical fiber sensor using the Rayleigh scattering phenomenon may be respectively configured separately, or partially shared.

Moreover, with the distributed optical fiber sensor of this embodiment, the cell width can be set to an arbitrary width (seconds). In the foregoing experiment, the cell width was set to 0.1 ns (nanoseconds), but if can also be set even shorter to, for example, a picosecond order or the like. Accordingly, the distributed optical fiber sensor FS of this embodiment is able to realize ultrahigh resolution of a millimeter order, and can be applied to the measurement of the strain of the optical component; for example, the strain of the optical waveguide.

The present invention has been appropriately and sufficiently explained above based on the embodiments with reference the appended drawings in order to express the present invention, but it should be recognized that a person skilled in the art can easily modify and/or improve the foregoing embodiments. Accordingly, so as long as the mode of modification or improvement by a person skilled in the art is of a level that does not deviate from the scope of claims provided below, such mode of modification or improvement should be interpreted as being covered by the scope of claims of the present invention.

The present invention explained above can be summarized as follows.

Specifically, the distributed optical fiber sensor according to the present invention is a distributed optical fiber sensor which uses an optical fiber as a sensor, comprising a Brillouin measuring unit for measuring a Brillouin frequency shift amount caused by a strain and a temperature generated in the optical fiber by using a Brillouin scattering phenomenon, a Rayleigh measuring unit for measuring a Rayleigh frequency shift amount caused by the strain and temperature generated in the optical fiber by using a Rayleigh scattering phenomenon, and a calculation unit for calculating the strain and temperature generated in the optical fiber based on the Brillouin frequency shift amount measured by the Brillouin measuring unit and the Rayleigh frequency shift amount measured by the Rayleigh measuring unit.

According to this distributed optical fiber sensor, since the Brillouin frequency shift amount caused by the strain and temperature generated in the optical fiber is measured by using the Brillouin scattering phenomenon, and the Rayleigh frequency shift amount caused by the strain and temperature generated in the optical fiber is measured by using the Rayleigh scattering phenomenon, the strain and temperature generated in the optical fiber can be simultaneously and independently calculated by using two frequency shift amounts, and the strain and temperature of the object to be measured appended with an optical fiber can be measured simultaneously and independently with high spatial resolution.

Moreover, the Rayleigh measuring unit of this invention can also measure the Rayleigh frequency shift amount by determining a frequency sweep range of pulsed light for measuring Rayleigh backscattered light based on the Brillouin frequency shift amount measured by the Brillouin measuring unit, and measuring the Rayleigh backscattered light by sweeping the pulsed light in the determined sweep range.

In the foregoing case, since the frequency sweep range of the pulsed light for measuring the Rayleigh backscattered light is determined from the measured Brillouin frequency shift amount, and the Rayleigh backscattered light is measured by sweeping the pulsed light in the determined sweep range, it is possible to sweep the pulsed light in a necessary and sufficient narrow sweep range and measure, in a short time, the Rayleigh frequency shift amount with extremely high sensitivity in comparison to the sensitivity of the Brillouin frequency shift amount.

Moreover, the Rayleigh measuring unit of this invention can also set, as a first frequency, a first Rayleigh frequency shift amount calculated based on a variation in temperature when the entire Brillouin frequency shift amount measured by the Brillouin measuring unit is deemed a shift amount caused by the temperature, and set, as a second frequency, a second Rayleigh frequency shift amount calculated based on a variation in strain when the entire Brillouin frequency shift amount measured by the Brillouin measuring unit is deemed a shift amount caused by the strain, and determine the sweep range based on the first frequency and the second frequency.

In the foregoing case, since the frequency sweep range of the pulsed light for measuring the Rayleigh backscattered light can be determined easily and in a short time from the measured Brillouin frequency shift amount, it is possible to measure, in a short time, the Rayleigh frequency shift amount with extremely high sensitivity in comparison to the sensitivity of the Brillouin frequency shift amount.

Moreover, the Rayleigh measuring unit of this invention can also measure the Rayleigh frequency shift amount from a cross-correlation coefficient of a Rayleigh scattering spectrum from the optical fiber in a predetermined reference state and a Rayleigh scattering spectrum from the optical fiber in a measurement state of the strain and temperature generated in the optical fiber in the reference state, and from a threshold based on a probability concerning reliability of the cross-correlation coefficient.

In the foregoing case, as a result of using the threshold based on the probability concerning the reliability of the cross-correlation coefficient, even if the strain and temperature are generated unevenly in the optical fiber and a plurality of peaks of the cross-correlation coefficient consequently appear, it is possible to select the correct peak of the cross-correlation coefficient by comparing the plurality of peaks and the threshold.

Moreover, the Rayleigh measuring unit can also measure the Rayleigh frequency shift amount from a cross-correlation coefficient of a square root of a Rayleigh scattering spectrum from the optical fiber in a predetermined reference state and a square root of a Rayleigh scattering spectrum from the optical fiber in a measurement state of the strain and temperature generated in the optical fiber in the reference state, and from a threshold based on a probability concerning reliability of the cross-correlation coefficient.

By using the square root of the spectrum rather than the spectrum itself, the level of cross-correlation coefficients in cases where they are mutually uncorrelated can be reduced, and, therefore, it is possible to reliably select the correct peak from the plurality of peaks of the cross-correlation coefficient.

Moreover, one of the Brillouin measuring unit and the Rayleigh measuring unit of this invention can also derive a correction amount concerning an actual measured position which is determined based on a travel time of light propagating in the optical fiber and an intended measuring position on the optical fiber which shifts from the actual measured position pursuant to expansion and contraction of the optical fiber, and use the correction amount to measure one of either the Brillouin frequency shift amount or the Rayleigh frequency shift amount, and the other measuring unit can also use the correction amount derived by the one measuring unit to measure the other of either the Brillouin frequency shift amount or the Rayleigh frequency shift amount.

In the foregoing case, even if there is a great shift between the position (actual measured position) in the optical fiber subject to the Brillouin backscattered light (or Rayleigh backscattered light) to be actually measured and the position (intended measuring position) in the optical fiber for which the measured value of the Brillouin backscattered light (or Rayleigh backscattered light) should be obtained for the derivation of the Brillouin frequency shift amount (or Rayleigh frequency shift amount), the correction amount concerning this shift can be derived from the Brillouin backscattered light (or Rayleigh backscattered light), and this correction amount can be used for accurately deriving the Brillouin frequency shift amount and the Rayleigh frequency shift amount.

Moreover, the Brillouin measuring unit of this invention can also derive the correction amount using Brillouin backscattered light from the optical fiber in a predetermined reference state and Brillouin backscattered light from the optical fiber in a measurement state of the strain and temperature generated in the optical fiber in the reference state.

In the foregoing case, the peak frequency can be derived easy and with high precision from the distribution (measured value) of the optical intensity of the Brillouin backscattered light measured from the optical fiber in the measurement state, and the distribution (measured value) of the optical intensity of the Brillouin backscattered light Brillouin backscattered light measured from the optical fiber in the reference state, and the correction amount can therefore be derived easily and with high precision based on the peak frequency in the respective measurement states.

Moreover, the Brillouin measuring unit of this invention can also include a storage unit for storing a reference measured value obtained from the Brillouin backscattered light from the optical fiber in the reference state, and a correction amount derivation unit for deriving the correction amount based on the reference measured value stored in the storage unit and a measured value obtained from the Brillouin backscattered light from the optical fiber in the measurement state.

In the foregoing case, the correction amount can be derived with even higher precision since it is possible to store the reference measured value that was measured after appending the optical fiber to the object to be measured, and, consequently, the strain and temperature of the object to be measured to which the optical fiber is appended can be measured accurately.

Moreover, the actual measured position can be set in plurality at intervals along a longitudinal direction of the optical fiber, the storage unit can store a plurality of reference measured values obtained from the Brillouin backscattered light from the respective actual measured positions of the optical fiber in the reference state, and the correction amount derivation unit can set a reference area in a part in the longitudinal direction of the optical fiber in the reference state, and derive the correction amount based on the reference measured values of the actual measured positions in the reference area stored in the storage unit, and measured values obtained from the Brillouin backscattered light from the respective actual measured positions in the optical fiber in the measurement state.

In the foregoing case, as a result of setting a reference area at a part in the longitudinal direction of the optical fiber in the reference state and deriving the correction amount based on the measured value obtained from the actual measured position included in the reference area, and the measured value obtained from the optical fiber in the measurement state, the correction amount can be derived reliably and in a short time in comparison to the case of deriving the correction amount based on all measured values obtained from the optical fiber in the reference state and all measured values obtained from the optical fiber in the measurement state.

Moreover, as a result of sequentially shifting the reference area along the longitudinal direction of the optical fiber, the correction amount relative to all actual measured positions of the optical fiber can also be derived reliably regardless of the length of the optical fiber.

Moreover, the Brillouin measuring unit of this invention can further include an interpolation unit for interpolating, based on the measured values obtained from the Brillouin backscattered light from the respective actual measured positions of the optical fiber in the measurement state, the measured values of the actual measured positions which are mutually adjacent in the longitudinal direction so that the plurality of measured values become successive in the longitudinal direction of the optical fiber, an estimation unit for respectively deriving the intended measuring positions corresponding to the plurality of actual measured positions from the respective actual measured positions included in the reference area based on the correction amount derived by the correction amount derivation unit, and estimating an estimated measured value obtained from the Brillouin backscattered light from the respective intended measuring positions based on the intended measuring positions and the values interpolated by the interpolation unit, and a shift amount derivation unit for deriving the Brillouin frequency shift amount based on the estimated measured value estimated by the estimation unit, and the measured value obtained from the Brillouin backscattered light from the actual measured position of the optical fiber in the reference state corresponding to an intended measuring position at which the estimated measured value has been estimated.

In the foregoing case, as a result of the plurality of measured values that can be obtained only discretely in the longitudinal direction of the optical fiber being interpolate, the measured value obtained from the Brillouin backscattered light from the intended measuring position corresponding to the actual measured position can be estimated easily.

Moreover, the distributed optical fiber sensor of this invention can further comprise polarization control unit for randomly changing a polarization plane of light, and the Brillouin measuring unit and the Rayleigh measuring unit can share the polarization control unit for measuring stimulated Brillouin scattered light and Rayleigh backscattered light.

In the foregoing case, since the polarization control unit is shared in the measurement of the stimulated Brillouin scattered light and the Rayleigh backscattered light, it is possible to simplify the configuration of the distributed optical fiber sensor and reduce the device cost.

Moreover, the Brillouin measuring unit of this invention can include a light pulse light source for generating a main light pulse using a spread spectrum system, and a non-modulated sub light pulse, a continuous light light source for generating continuous light, a detection optical fiber into which the sub light pulse and the main light pulse enter such that the main light pulse does not enter temporally before the sub light pulse, into which the continuous light enters, and in which a stimulated Brillouin scattering phenomenon occurs between the sub light pulse and the main light pulse, and the continuous light, a matched filter that is applied to the spread spectrum system and detects light pertaining to the stimulated Brillouin scattering phenomenon by filtering the light emitted from the detection optical fiber, and a Brillouin measuring unit for obtaining a Brillouin gain spectrum or a Brillouin loss spectrum based on the light pertaining to the stimulated Brillouin scattering phenomenon detected by the matched filter, and measuring the Brillouin frequency shift amount based on the obtained Brillouin gain spectrum or Brillouin loss spectrum.

In the foregoing case, the distributed optical fiber sensor can be caused to function as a BOTDA, and, while enabling the measurement of the strain and temperature with high spatial resolution, the measurable distance can be extended to enable measurement to a farther distance.

Moreover, the Brillouin measuring unit of this invention can include a light pulse light source for generating a main light pulse using a spread spectrum system, and a non-modulated sub light pulse, a detection optical fiber into which the sub light pulse and the main light pulse enter, and in which a natural Brillouin scattering phenomenon occurs due to a sound wave caused by thermal noise in the sub light pulse and the main light pulse, a matched filter that is applied to the spread spectrum system and detects light pertaining to the natural Brillouin scattering phenomenon by filtering the light emitted from the detection optical fiber, and a Brillouin measuring unit for obtaining a Brillouin gain spectrum based on the light pertaining to the natural Brillouin scattering phenomenon detected by the matched filter, and measuring the Brillouin frequency shift amount based on the obtained Brillouin gain spectrum.

In the foregoing case, the distributed optical fiber sensor can be caused to function as a BOTDR, and, while enabling the measurement of the strain and temperature with high spatial resolution, the measurable distance can be extended to enable measurement to a farther distance.

As described above, the distributed optical fiber sensor according to the present invention is useful as a distributed optical fiber sensor for measuring the strain and temperature of a test object, and suitable for measuring the strain and temperature of the test object simultaneously and independently with high spatial resolution.

The invention claimed is:

1. A distributed optical fiber sensor which uses an optical fiber as a sensor, comprising:
a light source for generating a light that enters the optical fiber;
a Brillouin measuring unit for measuring a Brillouin frequency shift amount caused by a strain and a temperature generated in the optical fiber by using a Brillouin scattering phenomenon based on light that exits the optical fiber;
a Rayleigh measuring unit for measuring a Rayleigh frequency shift amount caused by the strain and temperature generated in the optical fiber by using a Rayleigh scattering phenomenon based on light that exits the optical fiber; and
a calculation unit for calculating the strain and temperature generated in the optical fiber based on the Brillouin frequency shift amount measured by the Brillouin measuring unit, estimating the Rayleigh frequency shift amount based on the measured Brillouin frequency shift amount and calculating the Rayleigh frequency shift amount measured by the Rayleigh measuring unit.

2. The distributed optical fiber sensor according to claim 1, wherein the Rayleigh measuring unit measures the Rayleigh frequency shift amount by determining a frequency sweep range of pulsed light for measuring Rayleigh backscattered light based on the Brillouin frequency shift amount measured by the Brillouin measuring unit, and measuring the Rayleigh backscattered light by sweeping the pulsed light in the determined sweep range.

3. The distributed optical fiber sensor according to claim 2, wherein the Rayleigh measuring unit sets, as a first frequency, a first Rayleigh frequency shift amount calculated based on a variation in temperature when the entire Brillouin frequency shift amount measured by the Brillouin measuring unit is deemed a shift amount caused by the temperature, and sets, as a second frequency, a second Rayleigh frequency shift amount calculated based on a variation in strain when the entire Brillouin frequency shift amount measured by the Brillouin measuring unit is deemed a shift amount caused by the strain, and determines the sweep range based on the first frequency and the second frequency.

4. The distributed optical fiber sensor according to claim 1, wherein the Rayleigh measuring unit measures the Rayleigh frequency shift amount from a cross-correlation coefficient of a Rayleigh scattering spectrum from the optical fiber in a predetermined reference state and a Rayleigh scattering spectrum from the optical fiber in a measurement state of the strain and temperature generated in the optical fiber in the reference state, and from a threshold based on a probability concerning reliability of the cross-correlation coefficient.

5. The distributed optical fiber sensor according to claim 1, wherein the Rayleigh measuring unit measures the Rayleigh frequency shift amount from a cross-correlation coefficient of a square root of a Rayleigh scattering spectrum from the optical fiber in a predetermined reference state and a square root of a Rayleigh scattering spectrum from the optical fiber in a measurement state of the strain and temperature generated in the optical fiber in the reference state, and from a threshold based on a probability concerning reliability of the cross-correlation coefficient.

6. The distributed optical fiber sensor according to claim 1, wherein one of the Brillouin measuring unit and the Rayleigh measuring unit derives a correction amount concerning an actual measured position which is determined based on a travel time of light propagating in the optical fiber and an intended measuring position on the optical fiber which shifts from the actual measured position pursuant to expansion and contraction of the optical fiber, and uses the correction amount to measure one of either the Brillouin frequency shift amount or the Rayleigh frequency shift amount, and
the other measuring unit uses the correction amount derived by the one measuring unit to measure the other of either the Brillouin frequency shift amount or the Rayleigh frequency shift amount.

7. The distributed optical fiber sensor according to claim 6, wherein the Brillouin measuring unit derives the correction amount using Brillouin backscattered light from the optical fiber in a predetermined reference state and Brillouin backscattered light from the optical fiber in a measurement state of the strain and temperature generated in the optical fiber in the reference state.

8. The distributed optical fiber sensor according to claim 7, wherein the Brillouin measuring unit includes:
a storage unit for storing a reference measured value obtained from the Brillouin backscattered light from the optical fiber in the reference state; and
a correction amount derivation unit for deriving the correction amount based on the reference measured value stored in the storage unit and a measured value obtained from the Brillouin backscattered light from the optical fiber in the measurement state.

9. The distributed optical fiber sensor according to claim 8, wherein the actual measured position is set in plurality at intervals along a longitudinal direction of the optical fiber,
the storage unit stores a plurality of reference measured values obtained from the Brillouin backscattered light from the respective actual measured positions of the optical fiber in the reference state, and
the correction amount derivation unit sets a reference area in a part in the longitudinal direction of the optical fiber in the reference state, and derives the correction amount based on the reference measured values of the actual measured positions in the reference area stored in the storage unit, and measured values obtained from the Brillouin backscattered light from the respective actual measured positions in the optical fiber in the measurement state.

10. The distributed optical fiber sensor according to claim 9,
wherein the Brillouin measuring unit further includes:
an interpolation unit for interpolating, based on the measured values obtained from the Brillouin backscattered light from the respective actual measured positions of the optical fiber in the measurement state, the measured values of the actual measured positions which are mutually adjacent in the longitudinal direction so that the plurality of measured values become successive in the longitudinal direction of the optical fiber;
an estimation unit for respectively deriving the intended measuring positions corresponding to the plurality of actual measured positions from the respective actual measured positions included in the reference area based on the correction amount derived by the correction amount derivation unit, and estimating an estimated measured value obtained from the Brillouin backscattered light from the respective intended measuring positions based on the intended measuring positions and values interpolated by the interpolation unit; and
a shift amount derivation unit for deriving the Brillouin frequency shift amount based on the estimated measured value estimated by the estimation unit, and the measured value obtained from the Brillouin backscattered light from the actual measured position of the optical fiber in the reference state corresponding to an intended measuring position at which the estimated measured value has been estimated.

11. The distributed optical fiber sensor according to claim 1, further comprising:
polarization control unit for randomly changing a polarization plane of light,
wherein the Brillouin measuring unit and the Rayleigh measuring unit share the polarization control unit for measuring stimulated Brillouin scattered light and Rayleigh backscattered light.

12. The distributed optical fiber sensor according to claim 1,
wherein the Brillouin measuring unit includes:
a light pulse light source for generating a main light pulse using a spread spectrum system, and a non-modulated sub light pulse;
a continuous light source for generating continuous light;
a detection optical fiber into which the sub light pulse and the main light pulse enter such that the main light pulse does not enter temporally before the sub light pulse, into which the continuous light enters, and in which a stimulated Brillouin scattering phenomenon occurs between the sub light pulse and the main light pulse, and the continuous light;
a matched filter that is applied to the spread spectrum system and detects light pertaining to the stimulated Brillouin scattering phenomenon by filtering the light emitted from the detection optical fiber; and
a Brillouin measuring unit for obtaining a Brillouin gain spectrum or a Brillouin loss spectrum based on the light pertaining to the stimulated Brillouin scattering phenomenon detected by the matched filter, and measuring the Brillouin frequency shift amount based on the obtained Brillouin gain spectrum or Brillouin loss spectrum.

13. The distributed optical fiber sensor according to claim 1,
wherein the Brillouin measuring unit includes:
a light pulse light source for generating a main light pulse using a spread spectrum system, and a non-modulated sub light pulse;
a detection optical fiber into which the sub light pulse and the main light pulse enter, and in which a natural Brillouin scattering phenomenon occurs due to a sound wave caused by thermal noise in the sub light pulse and the main light pulse;
a matched filter that is applied to the spread spectrum system and detects light pertaining to the natural Brillouin scattering phenomenon by filtering the light emitted from the detection optical fiber; and
a Brillouin measuring unit for obtaining a Brillouin gain spectrum based on the light pertaining to the natural Brillouin scattering phenomenon detected by the matched filter, and measuring the Brillouin frequency shift amount based on the obtained Brillouin gain spectrum.

* * * * *